US012686724B2

(12) United States Patent
Cha

(10) Patent No.: US 12,686,724 B2
(45) Date of Patent: Jul. 21, 2026

(54) MONOCLONAL ANTIBODIES AND ANTIGEN BINDING FRAGMENTS THEREOF FOR SUPPRESSING CD73 IMMUNE CHECKPOINT AND USES THEREOF

(71) Applicant: APRILBIO CO., LTD., Chuncheon-si (KR)

(72) Inventor: Sang Hoon Cha, Chuncheon-si (KR)

(73) Assignee: Aprilbio Co., Ltd, Chuncheon-si (KR)

( * ) Notice: Subject to any disclaimer, the term of this patent is extended or adjusted under 35 U.S.C. 154(b) by 710 days.

(21) Appl. No.: 17/917,513

(22) PCT Filed: Apr. 9, 2021

(86) PCT No.: PCT/IB2021/052934
§ 371 (c)(1),
(2) Date: Oct. 6, 2022

(87) PCT Pub. No.: WO2021/205383
PCT Pub. Date: Oct. 14, 2021

(65) Prior Publication Data
US 2023/0174665 A1 Jun. 8, 2023

(30) Foreign Application Priority Data

Apr. 9, 2020 (KR) ........................ 10-2020-0043607
Nov. 2, 2020 (KR) ........................ 10-2020-0144595

(51) Int. Cl.
| | |
|---|---|
| *C07K 16/28* | (2006.01) |
| *A61K 39/00* | (2006.01) |
| *A61K 39/395* | (2006.01) |
| *A61K 45/06* | (2006.01) |
| *A61P 35/00* | (2006.01) |
| *A61P 35/04* | (2006.01) |

(52) U.S. Cl.
CPC .... *C07K 16/2896* (2013.01); *A61K 39/39558* (2013.01); *A61K 45/06* (2013.01); *A61P 35/00* (2018.01); *A61P 35/04* (2018.01); *A61K 2039/505* (2013.01); *C07K 2317/21* (2013.01); *C07K 2317/565* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 6,610,515 B1 | 8/2003 | Yamamoto et al. | |
| 7,439,336 B2 | 10/2008 | Kornmann et al. | |
| 7,691,611 B2 | 4/2010 | Weber et al. | |
| 7,820,800 B2 | 10/2010 | Rossi et al. | |
| 7,943,746 B2 | 5/2011 | Kornmann et al. | |
| 8,128,920 B2 | 3/2012 | Sagot et al. | |
| 8,217,152 B2 | 7/2012 | Le Strat et al. | |

| | | | |
|---|---|---|---|
| 8,846,042 B2 | 9/2014 | Zhou | |
| 8,921,528 B2 | 12/2014 | Holt et al. | |
| 9,566,313 B2 | 2/2017 | Chvatchko et al. | |
| 9,592,267 B2 | 3/2017 | Chvatchko et al. | |
| 9,879,077 B2 | 1/2018 | Cha | |
| 10,618,953 B2 | 4/2020 | Cha | |
| 10,858,426 B2 | 12/2020 | Pfeifer et al. | |
| 10,882,905 B2 | 1/2021 | Del Val et al. | |
| 11,773,176 B2 | 10/2023 | Cha | |
| 2004/0229338 A1 | 11/2004 | King | |
| 2006/0269515 A1 | 11/2006 | Denis-Mize et al. | |
| 2007/0059301 A1 | 3/2007 | Humphreys et al. | |
| 2009/0111745 A1 | 4/2009 | Tomlinson | |
| 2010/0227818 A1 | 9/2010 | Bock et al. | |
| 2011/0177065 A1 | 7/2011 | Rubinstein et al. | |
| 2012/0321626 A1 | 12/2012 | Zhou | |
| 2013/0316354 A1 | 11/2013 | Bazan | |
| 2014/0044675 A1 | 2/2014 | Hosse et al. | |
| 2016/0215048 A1 | 7/2016 | Pfeifer et al. | |
| 2016/0304574 A1 | 10/2016 | Sharma et al. | |
| 2016/0376350 A1 | 12/2016 | Cha | |
| 2017/0355756 A1 | 12/2017 | Julien et al. | |
| 2019/0031766 A1 | 1/2019 | Prinz et al. | |
| 2020/0040052 A1 | 2/2020 | Winston et al. | |
| 2022/0242963 A1* | 8/2022 | Griffin ................... A61P 35/00 |
| 2023/0220093 A1 | 7/2023 | Cha | |

FOREIGN PATENT DOCUMENTS

| | | |
|---|---|---|
| CN | 101280019 A | 10/2008 |
| CN | 107082815 A | 8/2017 |
| EP | 1033373 A1 | 9/2000 |

(Continued)

OTHER PUBLICATIONS

Allard et al., Int. J. Cancer, 134, 1466-1473, Publication Date: Aug. 26, 2013 (Year: 2013).*
Ni et al., The Protein Journal, 43, pp. 683-696, Jul. 2024 (Year: 2024).*
International Search Report mailed Jul. 8, 2021, in International Application No. PCT/IB2021/052934.
Written Opinion mailed Jul. 8, 2021, in International Application No. PCT/IB2021/052934.
Extended ESR issued in the EP Application No. 21783964.6, mailed on Sep. 25, 2024.
Miller et al., (2022) Journal of Immunotherapy of cancer, vol. 10, No. 12, Dec. 1, 2022, p. e005802, "Anti-CD73 antibody activates human B cells, enhances humoral responses and induces redistribution of B cells in patients with cancer".

(Continued)

*Primary Examiner* — Peter J Reddig
*Assistant Examiner* — Cheng Lu
(74) *Attorney, Agent, or Firm* — Potomac Law Group, PLLC; Judith U. Kim

(57) ABSTRACT

Provided are monoclonal antibodies and antigen binding fragments thereof for suppressing a CD73 immune checkpoint, and uses thereof, wherein the antibodies or antigen binding fragments thereof can bind to CD73, reduce enzymatic activity of CD73 protein, and inhibit cancer metastasis or cancer growth, thus enabling uses thereof as therapeutic agents for cancer.

10 Claims, 18 Drawing Sheets

Specification includes a Sequence Listing.

(56)                 References Cited

FOREIGN PATENT DOCUMENTS

| | | | |
|---|---|---|---|
| EP | 3297672 | A1 | 3/2018 |
| EP | 3569618 | A1 | 11/2019 |
| JP | H04502164 | A | 4/1992 |
| JP | H11196881 | A | 7/1999 |
| JP | 2007535472 | A | 12/2007 |
| JP | 2008500830 | A | 1/2008 |
| JP | 2018501197 | A | 1/2018 |
| KR | 20070041781 | A | 4/2007 |
| KR | 20070073886 | A | 7/2007 |
| KR | 20110008086 | A | 1/2011 |
| KR | 20120133403 | A | 12/2012 |
| KR | 1020150118565 | A | 10/2015 |
| KR | 1020190080992 | A | 7/2019 |
| WO | 1987000532 | A1 | 7/1986 |
| WO | 9105798 | A1 | 5/1991 |
| WO | 1999009063 | A1 | 2/1999 |
| WO | 9920652 | A1 | 4/1999 |
| WO | 0187330 | A2 | 11/2001 |
| WO | 2004101617 | A1 | 11/2004 |
| WO | 2005049649 | A1 | 6/2005 |
| WO | 2005097998 | A2 | 10/2005 |
| WO | 2005118642 | A2 | 12/2005 |
| WO | 2006131550 | A1 | 12/2006 |
| WO | 2008068048 | A2 | 6/2008 |
| WO | 2010063818 | A2 | 6/2010 |
| WO | 2010110838 | A2 | 9/2010 |
| WO | 2011015649 | A1 | 2/2011 |
| WO | 2012158818 | A2 | 11/2012 |
| WO | 2013056068 | A1 | 4/2013 |
| WO | 2015030539 | A1 | 3/2015 |
| WO | 2015032932 | A1 | 3/2015 |
| WO | 2016075099 | A1 | 5/2016 |
| WO | 2016081748 | A2 | 5/2016 |
| WO | 2016126702 | A1 | 8/2016 |
| WO | 2016135239 | A1 | 9/2016 |
| WO | 2016187594 | A1 | 11/2016 |
| WO | 2017100670 | A1 | 6/2017 |
| WO | 2017102830 | A1 | 6/2017 |
| WO | 2017152085 | A1 | 9/2017 |
| WO | 2017157305 | A1 | 9/2017 |
| WO | 2018137598 | A1 | 8/2018 |
| WO | 2018215535 | A1 | 11/2018 |
| WO | 2018233895 | A1 | 12/2018 |
| WO | 2018237157 | A1 | 12/2018 |
| WO | 2019200256 | A1 | 10/2019 |
| WO | 2019224025 | A2 | 11/2019 |
| WO | 2021149015 | A1 | 7/2021 |
| WO | 2021205383 | A1 | 10/2021 |
| WO | 2021205401 | A1 | 10/2021 |
| WO | 2022070112 | A1 | 4/2022 |
| WO | 2022087149 | A1 | 4/2022 |
| WO | 2022087149 | A2 | 4/2022 |
| WO | 2024075050 | A1 | 4/2024 |
| WO | 2024084432 | A1 | 4/2024 |
| WO | 2025114319 | A1 | 6/2025 |
| WO | 2025253161 | A1 | 12/2025 |

OTHER PUBLICATIONS

Partial ESR issued in the EP Application No. 21783964.6, mailed on Jun. 17, 2024.

Wurm et al. (2021) Molecular Cancer Therapeutics, vol. 20, No. 11, pp. 2250-2261 "A Novel Antagonistic CD73 Antibody for Inhibition of the Immunosuppressive Adenosine Pathway".

Yarilin A.A., Fundamentals of Immunology: Textbook.—M.: Medicine, 608 p.; p. 171 second paragraph, pp. 172-173 (1999). Relevance in English provided in English translation of 3rd Office Action issued in RU Application No. 2022119090, mailed on Mar. 14, 2025, submitted herewith.

Allard, B. et al., "Targeting CD73 Enhances the Antitumor Activity of Anti-PD-1 and Anti-CTLA-4 mAbs," Intl. J. Cancer 134:1466-1473 (2013).

Chen, X. et al., "Fusion protein linkers: Property, design and functionality," Advanced Drug Delivery Rev. 65:1357-1369 (2013).

Edwards, B.M. et al., "The Remarkable Flexibility of the Human Antibody Repertoire; Isolation of Over One Thousand Different Antibodies to a Single Protein, BLyS," J. Mol. Biol. 334:103-118 (2003).

Goel, M. et al., "Plasticity within the Antigen-Combining Site May Manifest as Molecular Mimicry in the Humoral Immune Response," J. Immunol. 173:7358-7367 (2004).

Janeway, Jr., C. A. et al., "Structure of the Antibody Molecule and Immunoglobulin Genes," Immuno Biology, The Immune System in Health and Disease, 3rd ed., Current Biology Ltd. and Garland Publishing, Inc., pp. 3:1-3:11 (1997).

Kanyavuz, A. et al., "Breaking the law: unconventional strategies for antibody diversification," Nat. Rev. Immunol. 19:355-368 (Jun. 2019).

Lescar, J. et al., "Crystal Structure of a Cross-reaction Complex between Fab F9.13.7 and Guinea Fowl Lysozyme," J. Biol. Chem. 270:18067-18076 (1995).

Lloyd, C. et al., "Modelling the human immune response: performance of a I011 human antibody repertoire against a broad panel of therapeutically relevant antigens," Protein Engin., Design & Selection 22:159-168 (pub'd online Oct. 2008).

Rudikoff, S., "Single amino acid substitution altering antigen-binding specificity," Proc. Natl. Acad. Sci. USA 79:1979-1983 (1982).

Winkler, K. et al., "Changing the Antigen Binding Specificity by Single Point Mutations of an Anti-p24 (HIV-1) Antibody," J. Immunol. 165(8): 4505-4514 (2000).

Brennan et al., "Safety testing of monoclonal antibodies in in-human primates: Case studies highlighting their impact on human risk assessment," MABS, 2018, vol. 10, No. 1, I-17.

Chen et al., Enhancement and destruction of antibody function by somatic mutation: unequal occurrence is controlled by V gene combinatorial associations. EMBO J. Jun. 15, 1995; 14(12):2784-94. (Year: 1995).

Cho et al., "Structural basis of serum albumin recognition by SL335, an antibody Fab extending the serum half-life of protein therapeutics," BBRC 526:941-946, Elsevier (Mar. 2020).

Dave, E. et al. "Fab-dsFv: A bispecific antibody format with extended serum half-life through albumin binding," MABS vol. 8, No. 7, pp. 1319-1335 ((2016).

European Extended Search Report issued in the EP Patent Application No. 21874697.2, mailed on Sep. 24, 2024.

European Search Report in European Patent Application No. 14839630.2. dated Feb. 27, 2017.

European Search Report issued in the EP Patent Application No. 21784423.2, mailed on May 13, 2024.

European Search Report, supplemental, issued in the EP Application No. 21744981.8, mailed on Feb. 23, 2024.

Feldon, S.E. et al., "Autologous T-Lymphocytes Stimulate Proliferation of Orbial Fibroblasts Derived from Patients with Graves' Ophthalmopathy," Investigative Opthalmology & Visual Sci. 46:3913 (Nov. 1, 2005).

Finkelstein A.V., Ptitsyn O.B. Physica belka: Kurs lektsiy s tsvetnymi ystereoscopitcheskimi illustratciyami i zadachami: uchebnoe posobie/ A.V. Finkelstein, O.B. Ptitsyn.—4th ed., ed. And add.—M. : KDU, 2012.—524 p.: table, ill. [32] col. ill.; see p. 23. Relevance in English provided in English translation of 2nd Office Action issued in RU Application No. 2022119090/10, mailed Oct. 15, 2024, submitted herewith.

Holt et al. "Anti-Serum Albumin Domain Antibodies for Extending the Half-Lives of Short Lived Drugs." Protein Engineering, Design and Selection. 21(2008):283-288.

Hong et al., "Recombinant Fc-IL-18BPc Isoform Inhibits IL-18-Induced Cytokine Production," Hybridoma, 2012, vol. 31, pp. 99-104, Mary Ann Liebert, Larchmont, New York.

Hust, M. et al., "Single chain Fab (scFab) fragment," BMC Biotechnology, 7(14):1-15 (2007), BioMed Central.

International Preliminary Report on Patentability and Written Opinion issued in the International Application No. PCT/IB2023/059986, mailed on Apr. 17, 2025.

International Preliminary Report on Patentability and Written Opinion issued in the international application No. PCT/IB2023/060573, mailed on May 1, 2025.

(56)         References Cited

OTHER PUBLICATIONS

International Search Report and the Written Opinion of the International Searching Authority, or the Declaration in International Application No. PCT/IB2021/050519 mailed Apr. 23, 2021.
International Search Report and Written Opinion in International Application No. PCT/IB2021/052934, mailed Jul. 8, 2021.
International Search Report and Written Opinion in International Application No. PCT/IB2021/052969, mailed Jul. 16, 2021.
International Search Report and Written Opinion in International Application No. PCT/IB2021/058964 dated Dec. 28, 2021.
International Search Report and Written Opinion issued in International Application No. PCT/IB2023/059986, mailed on Jan. 11, 2024.
International Search Report and Written Opinion issued in the International Application No. PCT/IB2024/055506, mailed on Feb. 25, 2025.
International Search Report in International Patent Application No. PCT/ KR2014/008106, dated Dec. 2, 2014.
International Search Report issued in the international application No. PCT/IB2023/060573, mailed on Feb. 2, 2024.
International Search Report of the International Search Authority issued in the International Application No. PCT/EP2024/083686, mailed on Mar. 14, 2025.
International Written Opinion in International Patent Application No. PCT/KR2014/008106, dated Dec. 2, 2014.
Jazayeri et al., "Half-Life Extension by Fusion to the Fe Region." Therapeutic Proteins. 157(2012):157-188.
Ji et al., "Intact bioactivities and improved pharmacokinetic of the SL335-IFN-β-1a fusion protein that created by genetic fusion of SL335, a human anti-serum albumin fab, and human interferon-β", Immunology Letters, 2019, vol. 207, pp. 46-55, Elsevier, Amsterdam, The Netherlands.
Jiang, Y. et al. "Effect of a structurally modified human granulocyte colony stimulating factor, G-CSFa, on leukopenia in mice and monkeys" Journal of Hematology & Oncology, Biomed Central Ltd. London UK, vol. 4, No. 1, Jun. 13, 2011 p. 28, XP02114359.
JP Office action issued in the JP Application No. 2016-538860, mailed on Mar. 21, 2017.
Jung, S. et al., "LAPS-FSH: a new and effective long-acting follicle-stimulating hormone analogue for the treatment of infertility," Reproduction, Fertility and Development 26:1142-1153 (2014).
Kahaly, G.J. et al., "A Novel Anti-CD40 Monoclonal Antibody, Iscalimab, for Control of Graves Hyperthyroidism—A Proof-of-Concept Trial," J. Clin. Endocrin. Metab. 105:696-704 (Sep. 12, 2019).
Kanai et al., IgG1 heavy chain, partial [felis catus]—Protein—NCBI. 2020. 10. 14., GenBank: BAA32230.1, https://www.ncbi.nlm.nih.gov/protein/BAA32230.1?report=genbank&log$=protalign&blast_rank=1&RID=SD57Z4HK01R.
Kang et al., "Isolation of Human Anti-serum albumin Fab Antibodies with an Extended Serum-half Life," Immunology Letters 169:33-34 (Nov. 11, 2025).

Kang, H. et al., "Optimal expression of a Fab-effector fusion protein in Escherichia coli by removing the cysteine residues responsible for an interchain disulfide bond of a Fab molecule," Immunology Letters, 184:34-42 (2017), Elsevier B.V.
Koenig et al., "Mutational landscape of antibody variable domains reveals a switch modulating the interdomain conformational dynamics and antigen binding," PNAS 114 (4) E486-E495, Jan. 24, 2017.
Kussie et al., A single engineered amino acid substitution changes antibody fine specificity, J. Immuno. 152: 146-52 (1994).
Lee, S., "Effect of long-acting recombinant human follicle stimulating hormone (SAFA-FSH) on spermatogenesis," Master's Thesis, The Graduate School of Yonsei University, pp. 1-40, abstract and p. 13 (Dec. 2021).
Lu et al., Ig kappa chain [Felis catus]—Protein—NCBI, 2020. 10. 14., GenBank: ATI97435.1, https://www.ncbi.nlm.nih.gov/protein/ATI97435.1?report=genbank&log$=protalign&blast_rank=1&RID=SD5885Y501R.
Naik, V.M. et al., "Immunopathogenesis of Thyroid Eye Disease: Emerging Paradigms," Survey of Ophthalmology, Survey of Ophthalmology Inc. 55:215-226 (May 1, 2010).
Nicholson et al., "The enhanced immunopharmacology of VIB4920, a novel Tn3 fusion protein and CD40L antagonist, and assessment of its safety profile in cynomolgus monkeys," British Journal of Pharmacology 177:1061-1076, Sep. 2019.
Nico Mertens (2011) Bispecific Antibodies, pp. 135-149"Tribodies: Fab-scFv Fusion Proteins as a Platform to Create Multifunctional Pharmaceuticals".
Novick et al.; (1999) "Interleukin-18 Binding Protein, A Novel Modulator of the Th1 Cytokine Response" Immun. 10:127-136.
Qi, Y. et al., "The role of osteopontin in the induction of the CD40 ligand in Graves' disease," Clin. Endocrin. 80:128-134, Blackwell Scientific Publications (Jun. 3, 2013).
Second Office Action issued in the RU Application No. 2022119090/10(040313), mailed on Oct. 15, 2024.
Sexton, L. et al., "Resistive-Pulse Studies of Proteins and Protein/Antibody Complexes Using a Conical Nanotube Sensor," Journal of the American Chemical Society 129:13144-13152 (2007).
Smith et al., "Prolonged in Vivo Residence Times of Antibody Fragments Associated with Albumin," Bioconjugate Chem 12: 750-756, Apr. 12, 2001.
Smith, D. et al, "Relevance of Half-Life in Drug Design Miniperspective," J. Med. Chem. 61, 4273-4282 (10 pages), 2018.
Sogaard, M. et al., "Treatment with Tumor-Reactive Fab-IL-2 and Fab-Staphylococcal Enterotoxin A Fusion Proteins Leads to Sustained T Cell Activation, and Long-Term Survival of Mice with Established Tumors," International Journal of Oncology, 15:873-882 (Published online Nov. 1999), Active Biotech Research AB, Lund, SE.
Tang, A. et al., "Blockade of cD40-CD40 ligand pathway induces tolerance in muringe contact hypersensitivity," Eur. J. Immunol. 27:3143-3150 (Jan. 1, 1997).
Third Office Action issued in the RU Application No. 2022119090/10(040313), mailed on Mar. 14, 2025.

* cited by examiner

SEQUENCE LISTING

```
<160> NUMBER OF SEQ ID NOS: 115

<210> SEQ ID NO 1
<211> LENGTH: 5
<212> TYPE: PRT
<213> ORGANISM: Artificial Sequence
<220> FEATURE:
<223> OTHER INFORMATION: CDRH1 of L4-66

<400> SEQUENCE: 1

Asp Tyr Ala Met His
1               5

<210> SEQ ID NO 2
<211> LENGTH: 17
<212> TYPE: PRT
<213> ORGANISM: Artificial Sequence
<220> FEATURE:
<223> OTHER INFORMATION: CDRH2 of L4-66

<400> SEQUENCE: 2

Gly Ile Ser Asp Gly Gly Ser Ala Thr Thr Tyr Ala Asp Ser Val Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: CDRH3 of L4-66

<400> SEQUENCE: 3

Ala Gly Ser Ser Trp Tyr Phe Gly Ala Phe Asp Ile
1               5                   10

<210> SEQ ID NO 4
<211> LENGTH: 5
<212> TYPE: PRT
<213> ORGANISM: Artificial Sequence
<220> FEATURE:
<223> OTHER INFORMATION: CDRH1 of L6-1

<400> SEQUENCE: 4

Thr His Gly Met His
1               5

<210> SEQ ID NO 5
<211> LENGTH: 17
<212> TYPE: PRT
<213> ORGANISM: Artificial Sequence
<220> FEATURE:
```

```
<223> OTHER INFORMATION: CDRH2 of L6-1

<400> SEQUENCE: 5

Ala Ile Ser Tyr Asp Gly Ser Asn Gln Tyr Tyr Gly Glu Ser Val Lys
1               5                   10                  15

Gly

<210> SEQ ID NO 6
<211> LENGTH: 14
<212> TYPE: PRT
<213> ORGANISM: Artificial Sequence
<220> FEATURE:
<223> OTHER INFORMATION: CDRH3 of L6-1

<400> SEQUENCE: 6

Asp Val Asp Trp Gly Leu Pro Tyr Tyr Phe Gly Met Asp Val
1               5                   10

<210> SEQ ID NO 7
<211> LENGTH: 5
<212> TYPE: PRT
<213> ORGANISM: Artificial Sequence
<220> FEATURE:
<223> OTHER INFORMATION: CDRH1 of L2-3

<400> SEQUENCE: 7

Asp Thr Tyr Met His
1               5

<210> SEQ ID NO 8
<211> LENGTH: 17
<212> TYPE: PRT
<213> ORGANISM: Artificial Sequence
<220> FEATURE:
<223> OTHER INFORMATION: CDRH2 of L2-3

<400> SEQUENCE: 8

Arg Ile Asp Pro Ala Asn Gly Asn Ser Lys Tyr Val Pro Lys Phe Gln
1               5                   10                  15

Gly

<210> SEQ ID NO 9
<211> LENGTH: 19
<212> TYPE: PRT
<213> ORGANISM: Artificial Sequence
<220> FEATURE:
<223> OTHER INFORMATION: CDRH3 of L2-3

<400> SEQUENCE: 9

Gln Pro Val Val Val Leu Ala Ala Asn Val Tyr Tyr Arg Tyr Tyr Gly
1               5                   10                  15

Met Asp Val

<210> SEQ ID NO 10
<211> LENGTH: 8
<212> TYPE: PRT
<213> ORGANISM: Artificial Sequence
<220> FEATURE:
<223> OTHER INFORMATION: CDRH1 of L4-4, L4-5

<400> SEQUENCE: 10

Ser Trp Leu Gly Glu Phe Pro Tyr
1               5
```

<210> SEQ ID NO 11
<211> LENGTH: 17
<212> TYPE: PRT
<213> ORGANISM: Artificial Sequence
<220> FEATURE:
<223> OTHER INFORMATION: CDRH2 of L4-4, L4-5

<400> SEQUENCE: 11

Val Ile Ser Tyr Asp Gly Ser Asn Lys Tyr Tyr Ala Asp Ser Val Lys
1               5                   10                  15

Gly

<210> SEQ ID NO 12
<211> LENGTH: 8
<212> TYPE: PRT
<213> ORGANISM: Artificial Sequence
<220> FEATURE:
<223> OTHER INFORMATION: CDRH3 of L4-4

<400> SEQUENCE: 12

Ser Trp Leu Gly Glu Phe Pro Tyr
1               5

<210> SEQ ID NO 13
<211> LENGTH: 11
<212> TYPE: PRT
<213> ORGANISM: Artificial Sequence
<220> FEATURE:
<223> OTHER INFORMATION: CDRH3 of L4-5

<400> SEQUENCE: 13

Asp Pro Gly Ile Ala Ala Ala Gly Phe Asp Tyr
1               5                   10

<210> SEQ ID NO 14
<211> LENGTH: 5
<212> TYPE: PRT
<213> ORGANISM: Artificial Sequence
<220> FEATURE:
<223> OTHER INFORMATION: CDRH1 of L4-46

<400> SEQUENCE: 14

Ser Ser Ala Ile His
1               5

<210> SEQ ID NO 15
<211> LENGTH: 17
<212> TYPE: PRT
<213> ORGANISM: Artificial Sequence
<220> FEATURE:
<223> OTHER INFORMATION: CDRH2 of L4-46

<400> SEQUENCE: 15

Val Ile Ser Tyr Asp Gly Asn Gly Lys Tyr Tyr Gly Asp Ser Val Lys
1               5                   10                  15

Gly

<210> SEQ ID NO 16
<211> LENGTH: 11
<212> TYPE: PRT
<213> ORGANISM: Artificial Sequence
<220> FEATURE:
<223> OTHER INFORMATION: CDRH3 of L4-46

<400> SEQUENCE: 16

Ile Arg Gly Tyr Gly Leu Val Asp Met Asp Val

-continued

```
1                    5                    10
```

```
<210> SEQ ID NO 17
<211> LENGTH: 5
<212> TYPE: PRT
<213> ORGANISM: Artificial Sequence
<220> FEATURE:
<223> OTHER INFORMATION: CDRH1 of L8-24

<400> SEQUENCE: 17

Asn Tyr Gly Ile Thr
1               5

<210> SEQ ID NO 18
<211> LENGTH: 17
<212> TYPE: PRT
<213> ORGANISM: Artificial Sequence
<220> FEATURE:
<223> OTHER INFORMATION: CDRH2 of L8-24

<400> SEQUENCE: 18

Trp Ile Ser Thr Tyr Asn Gly Asn Thr Asn Tyr Ala Gln Lys Phe Gln
1               5                   10                  15

Asp

<210> SEQ ID NO 19
<211> LENGTH: 6
<212> TYPE: PRT
<213> ORGANISM: Artificial Sequence
<220> FEATURE:
<223> OTHER INFORMATION: CDRH3 of L8-2

<400> SEQUENCE: 19

Gly Trp Gly Phe Ala His
1               5

<210> SEQ ID NO 20
<211> LENGTH: 11
<212> TYPE: PRT
<213> ORGANISM: Artificial Sequence
<220> FEATURE:
<223> OTHER INFORMATION: CDRL1 of L4-4, L4-5, L4-46, L4-66

<400> SEQUENCE: 20

Arg Ala Ser Gln Asn Ile Gly Ser Trp Leu Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: CDRL2 of L4-4, L4-5, L4-46, L4-66

<400> SEQUENCE: 21

Arg Ala Ser Asn Leu Arg Ser
1               5

<210> SEQ ID NO 22
<211> LENGTH: 9
<212> TYPE: PRT
<213> ORGANISM: Artificial Sequence
<220> FEATURE:
<223> OTHER INFORMATION: CDRL3 of L4-4, L4-5, L4-46, L4-46

<400> SEQUENCE: 22
```

```
Gln Gln Ala Thr Ile Phe Pro Leu Thr
1               5

<210> SEQ ID NO 23
<211> LENGTH: 11
<212> TYPE: PRT
<213> ORGANISM: Artificial Sequence
<220> FEATURE:
<223> OTHER INFORMATION: CDRL1 of L6-1

<400> SEQUENCE: 23

Arg Ala Ser Gln Ser Ile Ser Ser Tyr Leu Asn
1               5                   10

<210> SEQ ID NO 24
<211> LENGTH: 7
<212> TYPE: PRT
<213> ORGANISM: Artificial Sequence
<220> FEATURE:
<223> OTHER INFORMATION: CDRL2 of L6-1

<400> SEQUENCE: 24

Ala Ala Ser Ser Leu Gln Ser
1               5

<210> SEQ ID NO 25
<211> LENGTH: 10
<212> TYPE: PRT
<213> ORGANISM: Artificial Sequence
<220> FEATURE:
<223> OTHER INFORMATION: Artificial Sequence

<400> SEQUENCE: 25

Gln Gln Ser Tyr Ser Thr Pro Pro Tyr Thr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: CDRL1 of L2-3

<400> SEQUENCE: 26

Arg Ala Ser Gln Ser Ile Ser Arg Tyr Leu Asn
1               5                   10

<210> SEQ ID NO 27
<211> LENGTH: 7
<212> TYPE: PRT
<213> ORGANISM: Artificial Sequence
<220> FEATURE:
<223> OTHER INFORMATION: CDRL2 of L2-3

<400> SEQUENCE: 27

Gly Ala Ser Arg Leu Glu Ser
1               5

<210> SEQ ID NO 28
<211> LENGTH: 9
<212> TYPE: PRT
<213> ORGANISM: Artificial Sequence
<220> FEATURE:
<223> OTHER INFORMATION: CDRL3 of L2-3

<400> SEQUENCE: 28

Gln Gln Ser Asp Ser Val Pro Val Thr
```

1               5

<210> SEQ ID NO 29
<211> LENGTH: 11
<212> TYPE: PRT
<213> ORGANISM: Artificial Sequence
<220> FEATURE:
<223> OTHER INFORMATION: CDRL1 of L8-2

<400> SEQUENCE: 29

Gln Ala Ser Asp Lys Ile Asn Asn Tyr Leu Asn
1               5                   10

<210> SEQ ID NO 30
<211> LENGTH: 7
<212> TYPE: PRT
<213> ORGANISM: Artificial Sequence
<220> FEATURE:
<223> OTHER INFORMATION: CDRL2 of L8-24

<400> SEQUENCE: 30

Asp Ala Ser Asn Leu Gln Thr
1               5

<210> SEQ ID NO 31
<211> LENGTH: 10
<212> TYPE: PRT
<213> ORGANISM: Artificial Sequence
<220> FEATURE:
<223> OTHER INFORMATION: CDRL3 of L8-24

<400> SEQUENCE: 31

Gln Gln Tyr Asn Ser Tyr Pro Tyr Ala Thr
1               5                   10

<210> SEQ ID NO 32
<211> LENGTH: 121
<212> TYPE: PRT
<213> ORGANISM: Artificial Sequence
<220> FEATURE:
<223> OTHER INFORMATION: VH of L4-66

<400> SEQUENCE: 32

Gln Val Gln Leu Val Gln Ser Gly Gly Gly Leu Val Gln Pro Gly Arg
1               5                   10                  15

Tyr Leu Arg Leu Ser Cys Val Ala Ser Gly Phe Asn Phe Asp Asp Tyr
                20                  25                  30

Ala Met His Trp Val Arg Gln Ala Pro Gly Lys Ala Leu Glu Trp Val
            35                  40                  45

Ser Gly Ile Ser Asp Gly Gly Ser Ala Thr Thr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Leu Asn Ser Leu Thr Ala Glu Asp Thr Ala Val Tyr Tyr Cys
                85                  90                  95

Ala Arg Ala Gly Ser Ser Trp Tyr Phe Gly Ala Phe Asp Ile Trp Gly
            100                 105                 110

Gln Gly Thr Leu Val Thr Val Ser Ser
        115                 120

<210> SEQ ID NO 33
<211> LENGTH: 123
<212> TYPE: PRT

-continued

```
<213> ORGANISM: Artificial Sequence
<220> FEATURE:
<223> OTHER INFORMATION: VH of L6-1

<400> SEQUENCE: 33

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Asn Thr His
            20                  25                  30

Gly Met His Trp Val Arg Gln Ala Pro Gly Lys Gly Leu Glu Trp Val
        35                  40                  45

Ala Ala Ile Ser Tyr Asp Gly Ser Asn Gln Tyr Tyr Gly Glu Ser Val
    50                  55                  60

Lys Gly Arg Phe Thr Ile Ser Arg Asp Asn Ser Arg Asp Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Val Asp Trp Gly Leu Pro Tyr Tyr Phe Gly Met Asp Val
            100                 105                 110

Trp Gly Gln Gly Thr Leu Val Thr Val Ser Ser
        115                 120

<210> SEQ ID NO 34
<211> LENGTH: 128
<212> TYPE: PRT
<213> ORGANISM: Artificial Sequence
<220> FEATURE:
<223> OTHER INFORMATION: VH of L2-3

<400> SEQUENCE: 34

Glu Val Gln Leu Val Gln Ser Gly Ala Glu Leu Val Glu Pro Gly Ala
1               5                   10                  15

Ser Val Lys Leu Ser Cys Thr Ala Ser Gly Phe Asn Ile Lys Asp Thr
            20                  25                  30

Tyr Met His Trp Ala Lys Gln Arg Pro Glu Gln Gly Leu Glu Trp Ile
        35                  40                  45

Gly Arg Ile Asp Pro Ala Asn Gly Asn Ser Lys Tyr Val Pro Lys Phe
    50                  55                  60

Gln Gly Lys Ala Thr Ile Thr Ala Asn Thr Ser Ser Asn Thr Ala Tyr
65                  70                  75                  80

Leu Gln Leu Thr Ser Leu Thr Ser Glu Asp Thr Ala Val Tyr Tyr Cys
                85                  90                  95

Ala Arg Gln Pro Val Val Val Leu Ala Ala Asn Val Tyr Tyr Arg Tyr
            100                 105                 110

Tyr Gly Met Asp Val Trp Gly Gln Gly Thr Leu Val Thr Val Ser Ser
        115                 120                 125

<210> SEQ ID NO 35
<211> LENGTH: 117
<212> TYPE: PRT
<213> ORGANISM: Artificial Sequence
<220> FEATURE:
<223> OTHER INFORMATION: VH of L4-4

<400> SEQUENCE: 35

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

-continued

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Leu Gly Glu Phe Pro Tyr Trp Gly Gln Gly Thr Met
            100                 105                 110

Val Thr Val Ser Ser
        115

<210> SEQ ID NO 36
<211> LENGTH: 120
<212> TYPE: PRT
<213> ORGANISM: Artificial Sequence
<220> FEATURE:
<223> OTHER INFORMATION: VH of L4-5

<400> SEQUENCE: 36

Gln Val Gln Leu Leu Gln Ser Gly Gly Gly Val Val Gln Pro Gly Arg
1                   5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ile Ala Ala Ala Gly Phe Asp Tyr Trp Gly Gln
            100                 105                 110

Gly Thr Met Val Thr Val Ser Ser
        115                 120

<210> SEQ ID NO 37
<211> LENGTH: 120
<212> TYPE: PRT
<213> ORGANISM: Artificial Sequence
<220> FEATURE:
<223> OTHER INFORMATION: VH of L4-46

<400> SEQUENCE: 37

Gln Val Gln Leu Val Gln Ser Gly Gly Gly Val Val Gln Pro Gly Arg
1                   5                   10                  15

Ser Leu Arg Leu Ser Cys Ala Ala Ser Gly Phe Arg Phe Ser Ser Ser
            20                  25                  30

Ala Ile His Trp Val Arg Gln Ala Pro Gly Lys Gly Leu Glu Trp Val
        35                  40                  45

Ala Val Ile Ser Tyr Asp Gly Asn Gly Lys Tyr Tyr Gly Asp Ser Val
    50                  55                  60

Lys Gly Arg Phe Ala Ile Ser Arg Asp Asn Ser Lys Ser Thr Val Tyr
65                  70                  75                  80

Leu Glu Met Asn Ser Leu Arg Asn Glu Asp Thr Ala Val Tyr Tyr Cys

-continued

```
                85                  90                  95
Ala Met Ile Arg Gly Tyr Gly Leu Val Asp Met Asp Val Trp Gly Gln
               100                 105                 110

Gly Thr Leu Val Thr Val Ser Ser
        115                 120

<210> SEQ ID NO 38
<211> LENGTH: 115
<212> TYPE: PRT
<213> ORGANISM: Artificial Sequence
<220> FEATURE:
<223> OTHER INFORMATION: VH of L8-24

<400> SEQUENCE: 38

Gln Val Gln Leu Leu Gln Ser Gly Ala Glu Val Lys Lys Pro Gly Ala
1               5                   10                  15

Ser Val Lys Val Ser Cys Glu Ala Ser Gly Tyr Thr Phe Thr Asn Tyr
               20                  25                  30

Gly Ile Thr Trp Val Arg Gln Ala Pro Gly Gln Gly Leu Glu Trp Met
        35                  40                  45

Gly Trp Ile Ser Thr Tyr Asn Gly Asn Thr Asn Tyr Ala Gln Lys Phe
    50                  55                  60

Gln Asp Arg Val Thr Met Thr Thr Asp Thr Ser Thr Ser Thr Ala Tyr
65                  70                  75                  80

Met Glu Val Arg Asn Leu Lys Ser Asp Asp Thr Ala Val Tyr Tyr Cys
                85                  90                  95

Ala Arg Gly Trp Gly Phe Ala His Trp Gly Gln Gly Thr Leu Val Thr
               100                 105                 110

Val Ser Ser
        115

<210> SEQ ID NO 39
<211> LENGTH: 107
<212> TYPE: PRT
<213> ORGANISM: Artificial Sequence
<220> FEATURE:
<223> OTHER INFORMATION: VL of L4-66,  L4-4, L4-5, L4-46

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Ser Trp
               20                  25                  30

Leu Ala Trp Tyr Gln Gln Lys Pro Gly Asn Ala Pro Lys Leu Leu Ile
        35                  40                  45

Tyr Arg Ala Ser Asn Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Thr Ile Phe Pro Leu
                85                  90                  95

Thr Phe Gly Gln Gly Thr Lys Leu Glu Ile Lys
               100                 105

<210> SEQ ID NO 40
<211> LENGTH: 108
<212> TYPE: PRT
<213> ORGANISM: Artificial Sequence
<220> FEATURE:
```

```
<223> OTHER INFORMATION: VL of L6-1

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Tyr Thr Phe Gly Gln Gly Thr Lys Leu Glu Ile Lys
            100                 105

<210> SEQ ID NO 41
<211> LENGTH: 107
<212> TYPE: PRT
<213> ORGANISM: Artificial Sequence
<220> FEATURE:
<223> OTHER INFORMATION: VL of L2-3

<400> SEQUENCE: 41

Asp Ile Gln Thr Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Gly Ala Ser Arg Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Val Pro Val
                85                  90                  95

Thr Phe Gly Gln Gly Thr Arg Leu Glu Ile Lys
            100                 105

<210> SEQ ID NO 42
<211> LENGTH: 108
<212> TYPE: PRT
<213> ORGANISM: Artificial Sequence
<220> FEATURE:
<223> OTHER INFORMATION: VL of L8-24

<400> SEQUENCE: 42

Glu Ile Val Leu Thr Gln Ser Pro Ser Ser Leu Ser Ala Ser Val Gly
1               5                   10                  15

Asp Arg Val Thr Ile Ser Cys Gln Ala Ser Asp Lys Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
```

-continued

```
                 65                    70                    75                    80
```

```
Glu Asp Ile Ala Thr Tyr Tyr Cys Gln Gln Tyr Asn Ser Tyr Pro Tyr
                 85                    90                    95
```

```
Ala Thr Phe Gly Gln Gly Thr Lys Val Asp Ile Lys
             100                   105
```

```
<210> SEQ ID NO 43
<211> LENGTH: 363
<212> TYPE: DNA
<213> ORGANISM: Artificial Sequence
<220> FEATURE:
<223> OTHER INFORMATION: VH of L4-66

<400> SEQUENCE: 43
caggtgcagc tggtgcagtc cggaggaggc ctggtgcagc caggaagata tttgcggctg      60
tcctgcgtgg cctccggctt caacttcgac gactacgcca tgcactgggt gaggcaggct     120
cccggaaagg ccctggagtg ggtgtccgga atcagcgatg cggcagcgc caccacctac      180 gctgactctg tgaagggcag gtttaccatc tccaggata acgctaagaa tacccttat      240 ctgcagctga atagcctgac cgctgaggac accgccgtgt attattgcgc cagggccggc     300
agcagctggt attttggcgc cttcgatatt tggggccagg gcaccctggt gaccgtgtct     360
agc                                                                   363
```

```
<210> SEQ ID NO 44
<211> LENGTH: 321
<212> TYPE: DNA
<213> ORGANISM: Artificial Sequence
<220> FEATURE:
<223> OTHER INFORMATION: VL of L4-66

<400> SEQUENCE: 44
gatattcaga tgacccagag cccagcagc ctgagcgcta gcgtgggcga cagggtgacc       60
atcacctgta gggctagcca gaacatcggc agctggctgg cctggtacca gcagaagcct     120
ggcaacgctc ctaagctgct gatctacagg gctagcaatc tgcggagcgg cgtgcccagc     180
aggtttagcg gctccggctc cggcaccgac ttcaccctga ccatcagctc cctgcagccc     240
gaggattttg ccacctattt ttgccagcag gccaccatct ttcctctgac cttcggccag     300
ggcaccaagc tggagatcaa g                                                321
```

```
<210> SEQ ID NO 45
<211> LENGTH: 369
<212> TYPE: DNA
<213> ORGANISM: Artificial Sequence
<220> FEATURE:
<223> OTHER INFORMATION: VH of L6-1

<400> SEQUENCE: 45
caggtgcagc tggtgcagtc cggcggcgga gtggtgcagc ctggaagatc cctgaggctg       60
agctgcgccg ccagcggatt cactttcaat acccacggca tgcactgggt gaggcaggcc     120
cctggcaagg gcctggagtg ggtggctgct atctcctacg acggcagcaa tcagtactac     180
ggcgagagcg tgaagggccg gttcaccatc agccgggaca cagccggga caccctgtat      240 ctgcagatga acagcctgag ggccgaggac accgccgtgt attactgcgc tagggatgtg     300
gactggggcc tgccctatta cttcggcatg gacgtgtggg gccagggcac cctggtgacc     360
gtgagctcc                                                             369
```

<210> SEQ ID NO 46
<211> LENGTH: 324
<212> TYPE: DNA
<213> ORGANISM: Artificial Sequence
<220> FEATURE:
<223> OTHER INFORMATION: VL of L6-1

<400> SEQUENCE: 46
gacatccaga tgacccagtc cccctcctcc ctgagcgcta gcgtgggcga tagggtgacc        60
atcacctgta gggcttccca gtccatctcc tcctacctga attggtatca gcagaagccc       120
ggcaaggccc ctaagctgct gatctacgct gcctccagcc tgcagagcgg cgtgccatcc       180
aggtttagcg gcagcggcag cggaaccgat ttcaccctga ccatcagctc cctgcagccc       240
gaggactttg ctacctatta ctgccagcag tcctactcca ccccccctta tacctttggc       300
cagggcacca agctggagat caag                                             324

<210> SEQ ID NO 47
<211> LENGTH: 37
<212> TYPE: DNA
<213> ORGANISM: Artificial Sequence
<220> FEATURE:
<223> OTHER INFORMATION: Light chain of Human IgG1

<400> SEQUENCE: 47
gatcaacaag cttgccacca tggagaccca cagccag                                37

<210> SEQ ID NO 48
<211> LENGTH: 24
<212> TYPE: DNA
<213> ORGANISM: Artificial Sequence
<220> FEATURE:
<223> OTHER INFORMATION: Light chain of Human IgG1

<400> SEQUENCE: 48
cccctccacc ccgctcagcc acag                                             24

<210> SEQ ID NO 49
<211> LENGTH: 54
<212> TYPE: DNA
<213> ORGANISM: Artificial Sequence
<220> FEATURE:
<223> OTHER INFORMATION: Light chain of Human IgG1

<400> SEQUENCE: 49
ctgagcgggg tggaggggga catccagatg acccagtctc catcttccct gtct            54

<210> SEQ ID NO 50
<211> LENGTH: 43
<212> TYPE: DNA
<213> ORGANISM: Artificial Sequence
<220> FEATURE:
<223> OTHER INFORMATION: Light chain of Human IgG1

<400> SEQUENCE: 50
ccaccgtacg tttgatttcc agcttggtcc cttggccgaa ggt                        43

<210> SEQ ID NO 51
<211> LENGTH: 37
<212> TYPE: DNA
<213> ORGANISM: Artificial Sequence
<220> FEATURE:
<223> OTHER INFORMATION: Heavy chain of Human IgG1

<400> SEQUENCE: 51

-continued gatcaacgaa ttcgccacca tggagtggtc ctgggtc                          37

<210> SEQ ID NO 52
<211> LENGTH: 27
<212> TYPE: DNA
<213> ORGANISM: Artificial Sequence
<220> FEATURE:
<223> OTHER INFORMATION: Heavy chain of Human IgG1

<400> SEQUENCE: 52
ggaaagcact ccggtggtca cgctgag                                     27

<210> SEQ ID NO 53
<211> LENGTH: 46
<212> TYPE: DNA
<213> ORGANISM: Artificial Sequence
<220> FEATURE:
<223> OTHER INFORMATION: Heavy chain of Human IgG1

<400> SEQUENCE: 53
gcgtgaccac cggagtgctt tcccaggtgc agctggtgca gtctgg                46

<210> SEQ ID NO 54
<211> LENGTH: 48
<212> TYPE: DNA
<213> ORGANISM: Artificial Sequence
<220> FEATURE:
<223> OTHER INFORMATION: Heavy chain of Human IgG1

<400> SEQUENCE: 54
cagtgggccc ttggtggagg ctgaggagac ggtgaccagg gtgccttg             48

<210> SEQ ID NO 55
<211> LENGTH: 22
<212> TYPE: DNA
<213> ORGANISM: Artificial Sequence
<220> FEATURE:
<223> OTHER INFORMATION: Heavy chain of Human IgG1 (APBA2-01)

<400> SEQUENCE: 55
gctagacacg gtcaccaggg tg                                          22

<210> SEQ ID NO 56
<211> LENGTH: 52
<212> TYPE: DNA
<213> ORGANISM: Artificial Sequence
<220> FEATURE:
<223> OTHER INFORMATION: Heavy chain of Human IgG1 (APBA2-01)

<400> SEQUENCE: 56
caccctggtg accgtgtcta gcgcatcaac aaaaggtcct tcagttttcc cc          52

<210> SEQ ID NO 57
<211> LENGTH: 44
<212> TYPE: DNA
<213> ORGANISM: Artificial Sequence
<220> FEATURE:
<223> OTHER INFORMATION: Heavy chain of Human IgG1 (APBA2-01)

<400> SEQUENCE: 57
aggaagacgc ttttagaggc ggccgctcac tttcctggtg aaag                  44

<210> SEQ ID NO 58
<211> LENGTH: 44
<212> TYPE: DNA
<213> ORGANISM: Artificial Sequence
<220> FEATURE:
<223> OTHER INFORMATION: Light chain of Human IgG1 (APBA2-02)

<400> SEQUENCE: 58
ctaggagcgg ccacggtccg cttgatctcc agcttggtgc cctg                          44

<210> SEQ ID NO 59
<211> LENGTH: 20
<212> TYPE: DNA
<213> ORGANISM: Artificial Sequence
<220> FEATURE:
<223> OTHER INFORMATION: Light chain of Human IgG1 (APBA2-02)

<400> SEQUENCE: 59
cggaccgtgg ccgctcctag                                                     20

<210> SEQ ID NO 60
<211> LENGTH: 34
<212> TYPE: DNA
<213> ORGANISM: Artificial Sequence
<220> FEATURE:
<223> OTHER INFORMATION: Light chain of Human IgG1 (APBA2-02)

<400> SEQUENCE: 60
ccactctaga gaagacgctt ttagatcaac actc                                     34

<210> SEQ ID NO 61
<211> LENGTH: 27
<212> TYPE: DNA
<213> ORGANISM: Artificial Sequence
<220> FEATURE:
<223> OTHER INFORMATION: Heavy chain of Human IgG1 (APBA2-02)

<400> SEQUENCE: 61
ggagctcacg gtcaccaggg tgccctg                                             27

<210> SEQ ID NO 62
<211> LENGTH: 45
<212> TYPE: DNA
<213> ORGANISM: Artificial Sequence
<220> FEATURE:
<223> OTHER INFORMATION: Heavy chain of Human IgG1 (APBA2-02)

<400> SEQUENCE: 62
gtgaccgtga gctccgcatc aacaaaaggt ccttcagttt ccccc                         45

<210> SEQ ID NO 63
<211> LENGTH: 52
<212> TYPE: DNA
<213> ORGANISM: Artificial Sequence
<220> FEATURE:
<223> OTHER INFORMATION: Heavy chain of Mouse IgG1 (APBA2-01)

<400> SEQUENCE: 63
caccctggtg accgtgtcta gcgctaagac tacccacca tcagtctatc cc                  52

<210> SEQ ID NO 64
<211> LENGTH: 30
<212> TYPE: DNA
<213> ORGANISM: Artificial Sequence
<220> FEATURE:
<223> OTHER INFORMATION: Heavy chain of Mouse IgG1 (APBA2-01)

<400> SEQUENCE: 64
atcggcggcc gcgaagacgc ttttagatca                                          30

-continued

```
<210> SEQ ID NO 65
<211> LENGTH: 52
<212> TYPE: DNA
<213> ORGANISM: Artificial Sequence
<220> FEATURE:
<223> OTHER INFORMATION: Heavy chain of Mouse IgG2a (APBA2-01)

<400> SEQUENCE: 65
caccctggtg accgtgtcta gcgctaaaac taccgcacct agcgtgtatc ct          52

<210> SEQ ID NO 66
<211> LENGTH: 5
<212> TYPE: PRT
<213> ORGANISM: Artificial Sequence
<220> FEATURE:
<223> OTHER INFORMATION: CDRH1 of 59H VH3-9

<400> SEQUENCE: 66

Asp Tyr Ala Met His
1               5

<210> SEQ ID NO 67
<211> LENGTH: 17
<212> TYPE: PRT
<213> ORGANISM: Artificial Sequence
<220> FEATURE:
<223> OTHER INFORMATION: CDRH2 of 59H VH3-9

<400> SEQUENCE: 67

Gly Ile Ser Trp Asn Ser Gly Ser Ile Gly Tyr Ala Asp Ser Val Lys
1               5                   10                  15

Gly

<210> SEQ ID NO 68
<211> LENGTH: 13
<212> TYPE: PRT
<213> ORGANISM: Artificial Sequence
<220> FEATURE:
<223> OTHER INFORMATION: CDRH3 of 59H VH3-9

<400> SEQUENCE: 68

Ala Arg Gly Tyr Ser Tyr Gly Glu Gly Ala Phe Asp Ile
1               5                   10

<210> SEQ ID NO 69
<211> LENGTH: 5
<212> TYPE: PRT
<213> ORGANISM: Artificial Sequence
<220> FEATURE:
<223> OTHER INFORMATION: CDRH1 of 60H VH3-9

<400> SEQUENCE: 69

Asp Tyr Ala Met His
1               5

<210> SEQ ID NO 70
<211> LENGTH: 17
<212> TYPE: PRT
<213> ORGANISM: Artificial Sequence
<220> FEATURE:
<223> OTHER INFORMATION: CDRH2 of 60H VH3-9

<400> SEQUENCE: 70

Gly Ile Ser Trp Asn Ser Gly Ser Ile Gly Tyr Ala Asp Ser Val Lys
1               5                   10                  15
```

-continued

```
Gly

<210> SEQ ID NO 71
<211> LENGTH: 13
<212> TYPE: PRT
<213> ORGANISM: Artificial Sequence
<220> FEATURE:
<223> OTHER INFORMATION: CDRH3 of 60H VH3-9

<400> SEQUENCE: 71

Asp Ile Trp Tyr Gly Gly Phe Phe Gly Ala Phe Asp Ile
1               5                   10

<210> SEQ ID NO 72
<211> LENGTH: 5
<212> TYPE: PRT
<213> ORGANISM: Artificial Sequence
<220> FEATURE:
<223> OTHER INFORMATION: CDRH1 of 69H VH3-9

<400> SEQUENCE: 72

Asp Tyr Ala Met His
1               5

<210> SEQ ID NO 73
<211> LENGTH: 17
<212> TYPE: PRT
<213> ORGANISM: Artificial Sequence
<220> FEATURE:
<223> OTHER INFORMATION: CDRH2 of 69H VH3-9

<400> SEQUENCE: 73

Gly Ile Ser Trp Asn Ser Gly Ser Ile Gly Tyr Ala Asp Ser Val Lys
1               5                   10                  15

Gly

<210> SEQ ID NO 74
<211> LENGTH: 11
<212> TYPE: PRT
<213> ORGANISM: Artificial Sequence
<220> FEATURE:
<223> OTHER INFORMATION: CDRH3 of 69H VH3-9

<400> SEQUENCE: 74

Gly Gly Phe Gly Val Val Thr Ala Leu Thr Val
1               5                   10

<210> SEQ ID NO 75
<211> LENGTH: 5
<212> TYPE: PRT
<213> ORGANISM: Artificial Sequence
<220> FEATURE:
<223> OTHER INFORMATION: CDRH1 of 75H VH1-18

<400> SEQUENCE: 75

Ser Tyr Gly Ile Ser
1               5

<210> SEQ ID NO 76
<211> LENGTH: 17
<212> TYPE: PRT
<213> ORGANISM: Artificial Sequence
<220> FEATURE:
<223> OTHER INFORMATION: CDRH2 of 75H VH1-18

<400> SEQUENCE: 76
```

Trp Ile Ser Ala Tyr Asn Gly Asn Thr Asn Tyr Ala Gln Lys Leu Gln
1               5                   10                  15

Gly

<210> SEQ ID NO 77
<211> LENGTH: 7
<212> TYPE: PRT
<213> ORGANISM: Artificial Sequence
<220> FEATURE:
<223> OTHER INFORMATION: CDRH3 of 75H VH1-18

<400> SEQUENCE: 77

Gly Thr Tyr Tyr Met Asp Val
1               5

<210> SEQ ID NO 78
<211> LENGTH: 5
<212> TYPE: PRT
<213> ORGANISM: Artificial Sequence
<220> FEATURE:
<223> OTHER INFORMATION: CDRH1 of 290H VH3-30

<400> SEQUENCE: 78

Arg Tyr Gly Met His
1               5

<210> SEQ ID NO 79
<211> LENGTH: 17
<212> TYPE: PRT
<213> ORGANISM: Artificial Sequence
<220> FEATURE:
<223> OTHER INFORMATION: CDRH2 of 290H VH3-30

<400> SEQUENCE: 79

Val Ile Ser Tyr Asp Gly Ser Asn Lys Tyr Tyr Ala Asp Ser Val Lys
1               5                   10                  15

Gly

<210> SEQ ID NO 80
<211> LENGTH: 12
<212> TYPE: PRT
<213> ORGANISM: Artificial Sequence
<220> FEATURE:
<223> OTHER INFORMATION: CDRH3 of 290H VH3-30

<400> SEQUENCE: 80

Gly Asp Ser Ser Gly Phe Leu Asn Ala Phe Asp Ile
1               5                   10

<210> SEQ ID NO 81
<211> LENGTH: 13
<212> TYPE: PRT
<213> ORGANISM: Artificial Sequence
<220> FEATURE:
<223> OTHER INFORMATION: CDRL1 of 59L VL1-44

<400> SEQUENCE: 81

Ser Gly Ser Ser Ser Asn Ile Gly Ser Asp Thr Val Thr
1               5                   10

<210> SEQ ID NO 82
<211> LENGTH: 7
<212> TYPE: PRT
<213> ORGANISM: Artificial Sequence
<220> FEATURE:
<223> OTHER INFORMATION: CDRL2 of 59L VL1-44

```
<400> SEQUENCE: 82

Ser Asn Ser Gln Arg Pro Ser
1               5

<210> SEQ ID NO 83
<211> LENGTH: 11
<212> TYPE: PRT
<213> ORGANISM: Artificial Sequence
<220> FEATURE:
<223> OTHER INFORMATION: CDRL3 of 59L VL1-44e

<400> SEQUENCE: 83

Ala Thr Trp Asp Ala Ser Leu Lys Ala Val Val
1               5                   10

<210> SEQ ID NO 84
<211> LENGTH: 13
<212> TYPE: PRT
<213> ORGANISM: Artificial Sequence
<220> FEATURE:
<223> OTHER INFORMATION: CDRL1 of 60L VL1-47

<400> SEQUENCE: 84

Ser Gly Ser Ser Ser Asn Ile Gly Thr Asn Ser Val Tyr
1               5                   10

<210> SEQ ID NO 85
<211> LENGTH: 7
<212> TYPE: PRT
<213> ORGANISM: Artificial Sequence
<220> FEATURE:
<223> OTHER INFORMATION: CDRL2 of 60L VL1-47

<400> SEQUENCE: 85

Arg Asn Phe Gln Arg Pro Ser
1               5

<210> SEQ ID NO 86
<211> LENGTH: 11
<212> TYPE: PRT
<213> ORGANISM: Artificial Sequence
<220> FEATURE:
<223> OTHER INFORMATION: CDRL3 of 60L VL1-4

<400> SEQUENCE: 86

Ala Gly Trp Asp Asp Ser Val Arg Gly Tyr Val
1               5                   10

<210> SEQ ID NO 87
<211> LENGTH: 11
<212> TYPE: PRT
<213> ORGANISM: Artificial Sequence
<220> FEATURE:
<223> OTHER INFORMATION: CDRL1 of 69L VK1-16

<400> SEQUENCE: 87

Arg Ala Ser Gln Gly Ile Ser Asn Tyr Leu Ala
1               5                   10

<210> SEQ ID NO 88
<211> LENGTH: 7
<212> TYPE: PRT
<213> ORGANISM: Artificial Sequence
<220> FEATURE:
<223> OTHER INFORMATION: CDRL2 of 69L VK1-16
```

```
<400> SEQUENCE: 88

Ala Ala Ser Ser Leu Gln Ser
1               5

<210> SEQ ID NO 89
<211> LENGTH: 9
<212> TYPE: PRT
<213> ORGANISM: Artificial Sequence
<220> FEATURE:
<223> OTHER INFORMATION: CDRL3 of 69L VK1-1

<400> SEQUENCE: 89

Gln Gln Tyr Lys Ser Tyr Pro Leu Thr
1               5

<210> SEQ ID NO 90
<211> LENGTH: 10
<212> TYPE: PRT
<213> ORGANISM: Artificial Sequence
<220> FEATURE:
<223> OTHER INFORMATION: CDRL1 of 75L VK1-12

<400> SEQUENCE: 90

Arg Ala Asn Gln Asp Ile Thr Trp Leu Val
1               5                   10

<210> SEQ ID NO 91
<211> LENGTH: 7
<212> TYPE: PRT
<213> ORGANISM: Artificial Sequence
<220> FEATURE:
<223> OTHER INFORMATION: CDRL2 of 75L VK1-12

<400> SEQUENCE: 91

Gly Ala Ser Ser Ser Gln Gly
1               5

<210> SEQ ID NO 92
<211> LENGTH: 9
<212> TYPE: PRT
<213> ORGANISM: Artificial Sequence
<220> FEATURE:
<223> OTHER INFORMATION: CDRL3 of 75L VK1-12

<400> SEQUENCE: 92

Gln Gln Ala Asp Arg Tyr Pro Leu Thr
1               5

<210> SEQ ID NO 93
<211> LENGTH: 11
<212> TYPE: PRT
<213> ORGANISM: Artificial Sequence
<220> FEATURE:
<223> OTHER INFORMATION: CDRL1 of 290L VK1-33

<400> SEQUENCE: 93

Gln Ala Ser Gln Asp Ile Ser Asn Tyr Leu Asn
1               5                   10

<210> SEQ ID NO 94
<211> LENGTH: 7
<212> TYPE: PRT
<213> ORGANISM: Artificial Sequence
<220> FEATURE:
<223> OTHER INFORMATION: CDRL2 of 290L VK1-33

<400> SEQUENCE: 94
```

```
Asp Ala Ser Asn Leu Glu Thr
1               5

<210> SEQ ID NO 95
<211> LENGTH: 9
<212> TYPE: PRT
<213> ORGANISM: Artificial Sequence
<220> FEATURE:
<223> OTHER INFORMATION: CDRL3 of 290L VK1-33

<400> SEQUENCE: 95

Gln Gln Tyr Asp Asn Leu Pro Leu Thr
1               5

<210> SEQ ID NO 96
<211> LENGTH: 122
<212> TYPE: PRT
<213> ORGANISM: Artificial Sequence
<220> FEATURE:
<223> OTHER INFORMATION: VH of 59H VH3-9

<400> SEQUENCE: 96

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ala Arg Gly Tyr Ser Tyr Gly Glu Gly Ala Phe Asp Ile Trp
            100                 105                 110

Gly Gln Gly Thr Met Val Thr Val Ser Ser
        115                 120

<210> SEQ ID NO 97
<211> LENGTH: 111
<212> TYPE: PRT
<213> ORGANISM: Artificial Sequence
<220> FEATURE:
<223> OTHER INFORMATION: VL of 59L VL1-44

<400> SEQUENCE: 97

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asp
            20                  25                  30

Thr Val Thr Trp Tyr Gln Asn Leu Pro Gly Thr Ala Pro His Val Val
            35                  40                  45

Ile Tyr Ser Asn Ser Gln Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ala Thr Trp Asp Ala Ser Leu
                85                  90                  95
```

```
Lys Ala Val Val Phe Gly Gly Gly Thr Lys Leu Thr Val Leu Gly
        100                 105                 110
```

```
<210> SEQ ID NO 98
<211> LENGTH: 122
<212> TYPE: PRT
<213> ORGANISM: Artificial Sequence
<220> FEATURE:
<223> OTHER INFORMATION: VH of 60H VH3-9
```

```
<400> SEQUENCE: 98
```

```
Gln Leu Gln Leu Val Glu Ser Gly Gly Gly Leu Val Gln Pro Gly Arg
1               5                   10                  15
```

```
Ser Leu Arg Leu Ser Cys Ala Ala Ser Gly Phe Thr Phe Asp Asp Tyr
            20                  25                  30
```

```
Ala Met His Trp Val Arg Gln Ala Pro Gly Lys Gly Leu Glu Trp Val
        35                  40                  45
```

```
Ser Gly Ile Ser Trp Asn Ser Gly Ser Ile Gly Tyr Ala Asp Ser Val
    50                  55                  60
```

```
Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Leu Tyr Tyr Cys
                85                  90                  95
```

```
Ala Lys Asp Ile Trp Tyr Gly Gly Phe Phe Gly Ala Phe Asp Ile Trp
            100                 105                 110
```

```
Gly Gln Gly Thr Met Val Thr Val Ser Ser
        115                 120
```

```
<210> SEQ ID NO 99
<211> LENGTH: 111
<212> TYPE: PRT
<213> ORGANISM: Artificial Sequence
<220> FEATURE:
<223> OTHER INFORMATION: VL of 60L VL1-47
```

```
<400> SEQUENCE: 99
```

```
Gln Ser Val Leu Thr Gln Pro Pro Ser Ala Ser Gly Thr Pro Gly Gln
1               5                   10                  15
```

```
Arg Val Thr Ile Pro Cys Ser Gly Ser Ser Ser Asn Ile Gly Thr Asn
            20                  25                  30
```

```
Ser Val Tyr Trp Tyr Gln Gln Phe Pro Gly Thr Ala Pro Lys Leu Leu
        35                  40                  45
```

```
Ile Tyr Arg Asn Phe Gln Arg Pro Ser Gly Val Pro Asp Arg Phe Ser
        50                  55                  60
```

```
Gly Ser Lys Ser Gly Thr Ser Ala Ser Leu Ala Ile Ala Gly Leu Arg
65                  70                  75                  80
```

```
Ser Glu Asp Glu Ala Asp Tyr Tyr Cys Ala Gly Trp Asp Asp Ser Val
                85                  90                  95
```

```
Arg Gly Tyr Val Phe Gly Thr Gly Thr Lys Leu Thr Val Leu Gly
            100                 105                 110
```

```
<210> SEQ ID NO 100
<211> LENGTH: 120
<212> TYPE: PRT
<213> ORGANISM: Artificial Sequence
<220> FEATURE:
<223> OTHER INFORMATION: VH of 69H VH3-9
```

```
<400> SEQUENCE: 100
```

```
Glu Val Gln Leu Val Glu Thr Gly Gly Gly Leu Val Gln Pro Gly Arg
```

-continued

```
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                    85                  90                  95

Ala Lys Gly Gly Phe Gly Val Val Thr Ala Leu Thr Val Trp Gly Gln
                100                 105                 110

Gly Thr Thr Val Thr Val Ser Ser
            115                 120

<210> SEQ ID NO 101
<211> LENGTH: 108
<212> TYPE: PRT
<213> ORGANISM: Artificial Sequence
<220> FEATURE:
<223> OTHER INFORMATION: VL of 69L VK1-16

<400> SEQUENCE: 101

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
            35                  40                  45

Tyr Ala Ala Ser Ser Leu Gln Ser Gly Val Pro Ser Lys Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Ser Tyr Pro Leu
                    85                  90                  95

Thr Phe Gly Gly Gly Thr Lys Val Asp Ile Lys Arg
                100                 105

<210> SEQ ID NO 102
<211> LENGTH: 116
<212> TYPE: PRT
<213> ORGANISM: Artificial Sequence
<220> FEATURE:
<223> OTHER INFORMATION: VH of 75H VH1-18

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
            50                  55                  60

Gln Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85              90                  95

Ala Arg Gly Thr Tyr Tyr Met Asp Val Trp Gly Lys Gly Thr Thr Val
            100             105                 110

Thr Val Ser Ser
        115

<210> SEQ ID NO 103
<211> LENGTH: 107
<212> TYPE: PRT
<213> ORGANISM: Artificial Sequence
<220> FEATURE:
<223> OTHER INFORMATION: VL of 75L VK1-12

<400> SEQUENCE: 103

Asp Ile Gln Met Thr Gln Ser Pro Ser Ser Val Thr Ala Ser Val Gly
1               5                   10                  15

Asp Arg Val Ser Ile Thr Cys Arg Ala Asn Gln Asp Ile Thr Trp Leu
            20                  25                  30

Val Trp Tyr Gln Gln Lys Pro Gly Lys Ala Pro Lys Phe Leu Met Ser
        35                  40                  45

Gly Ala Ser Ser Ser Gln Gly Gly Ala Pro Ser Arg Phe Ser Val Ser
    50                  55                  60

Glu Ser Gly Thr Asp Phe Thr Leu Thr Ile Ser Ser Leu Gln Pro Glu
65                  70                  75                  80

Asp Phe Ala Thr Tyr Tyr Cys Gln Gln Ala Asp Arg Tyr Pro Leu Thr
                85                  90                  95

Phe Gly Gly Gly Thr Lys Val Glu Ile Lys Arg
            100             105

<210> SEQ ID NO 104
<211> LENGTH: 119
<212> TYPE: PRT
<213> ORGANISM: Artificial Sequence
<220> FEATURE:
<223> OTHER INFORMATION: VH of 290H VH3-3

<400> SEQUENCE: 104

Gln Leu Leu Glu Ser Gly Gly Gly Val Val Gln Pro Gly Arg Ser Leu
1               5                   10                  15

Arg Leu Ser Cys Ala Ala Ser Gly Phe Thr Phe Ser Arg Tyr Gly Met
            20                  25                  30

His Trp Val Arg Gln Ala Pro Gly Lys Gly Leu Glu Trp Val Ala Val
        35                  40                  45

Ile Ser Tyr Asp Gly Ser Asn Lys Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Asp Ser Ser Gly Phe Leu Asn Ala Phe Asp Ile Trp Gly Gln Gly
            100             105                 110

Thr Met Val Thr Val Ser Ser
        115

<210> SEQ ID NO 105
<211> LENGTH: 108
<212> TYPE: PRT
<213> ORGANISM: Artificial Sequence
```

-continued

<220> FEATURE:
<223> OTHER INFORMATION: VL of 290L VK1-33

<400> SEQUENCE: 105

Val Ile Trp Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Asp Ile Lys Arg
            100                 105

<210> SEQ ID NO 106
<211> LENGTH: 366
<212> TYPE: DNA
<213> ORGANISM: Artificial Sequence
<220> FEATURE:
<223> OTHER INFORMATION: VH of 59H VH3-9

<400> SEQUENCE: 106
caggtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag cataggctat     180
gcggactctg tgaagggccg attcaccatc tccagagaca acgccaagaa ctccctgtat     240
ctgcaaatga acagtctgag agctgaggac acggccttgt attactgtgc aaaagcccgt     300
ggatacagct atggcgaggg ggcttttgat atctggggcc aagggacaat ggtcaccgtc     360
tcgagc                                                                366

<210> SEQ ID NO 107
<211> LENGTH: 333
<212> TYPE: DNA
<213> ORGANISM: Artificial Sequence
<220> FEATURE:
<223> OTHER INFORMATION: VL of 59L VL1-44

<400> SEQUENCE: 107
agctatgagc tgactcagcc accctcagcc tctgggaccc ccgggcagag ggtcaccatc      60
tcttgttctg gaagcagctc caacatcgga agtgatactg tgacctggta ccagaacctc     120
ccaggaacgg cccccatgt cgtcatatat agtaatagtc agcggccctc aggggtccct      180
gaccgcttct ctggctccaa gtctggcacc tcagcctccc tggccatcac tggtctccag     240
tctgaggatg aggctgatta ttactgtgca acatgggatg ccagtctgaa ggccgtggtc     300
ttcggcggag ggaccaagct gaccgtccta ggt                                  333

<210> SEQ ID NO 108
<211> LENGTH: 366
<212> TYPE: DNA
<213> ORGANISM: Artificial Sequence
<220> FEATURE:
<223> OTHER INFORMATION: VH of 60H VH3-9

-continued

<400> SEQUENCE: 108

```
cagctgcagc tggtggagtc tggggggaggc ttggtacagc ctggcaggtc cctgagactc      60
tcctgtgcag cctctggatt caccttttgat gattatgcca tgcactgggt ccggcaagct     120
ccagggaagg gcctggagtg ggtctcaggt attagttgga atagtggtag cataggctat     180
gcggactctg tgaagggccg attcaccatc tccagagaca acgccaagaa ctccctgtat     240
ctgcaaatga acagtctgag agctgaggac acggccttgt attactgtgc aaaagatatt     300
tggtatggtg gcttctttgg ggcttttgat atctggggcc aagggacaat ggtcaccgtc     360
tcgagc                                                                366
```

<210> SEQ ID NO 109
<211> LENGTH: 333
<212> TYPE: DNA
<213> ORGANISM: Artificial Sequence
<220> FEATURE:
<223> OTHER INFORMATION: VL of 60L VL1-47

<400> SEQUENCE: 109

```
cagtctgtgc tgactcagcc accctcagcg tctgggaccc ccgggcagag ggtcactatt      60
ccttgttctg gaagcagctc caacatcgga actaattctg tttattggta ccagcaattt     120
ccaggaacgg cccccaagct cctcatctat aggaattttc agcggccctc aggggtccct     180
gaccgatttt ctggctccaa gtctggcacc tccgcctccc tggccatcgc tggactccgg     240
tccgaggatg aggctgatta ttattgtgcg ggatgggatg acagtgtgag gggttatgtc     300
ttcggaactg ggaccaagct gaccgtccta ggt                                  333
```

<210> SEQ ID NO 110
<211> LENGTH: 360
<212> TYPE: DNA
<213> ORGANISM: Artificial Sequence
<220> FEATURE:
<223> OTHER INFORMATION: VH of 69H VH3-9

<400> SEQUENCE: 110

```
gaagtgcagc tggtggagac tggggggaggc ttggtacagc ctggcaggtc cctgagactc      60
tcctgtgcag cctctggatt caccttttgat gattatgcca tgcactgggt ccggcaagct     120
ccagggaagg gcctggagtg ggtctcaggt attagttgga atagtggtag cataggctat     180
gcggactctg tgaagggccg attcaccatc tccagagaca acgccaagaa ctccctgtat     240
ctgcaaatga acagtctgag agctgaggac acggccttgt attactgtgc aaaaggggggc     300 tttggagtgg ttacggccct tacagtctgg ggccaaggga ccacggtcac cgtctcgagc     360
```

<210> SEQ ID NO 111
<211> LENGTH: 324
<212> TYPE: DNA
<213> ORGANISM: Artificial Sequence
<220> FEATURE:
<223> OTHER INFORMATION: VL of 69L VK1-16

<400> SEQUENCE: 111

```
gccatccagt tgacccagtc tccatcctca ctgtctgcat ctgtaggaga cagagtcacc      60
atcacttgtc gggcgagtca gggcattagc aattatttag cctggtttca gcagaaacca     120
gggaaagccc ctaagtccct gatctatgct gcatccagtt tgcaaagtgg ggtcccatca     180
aagttcagcg gcagtggatc tgggacagat ttcactctca ccatcagcag cctgcagcct     240
```

-continued

```
gaagatttg caacttatta ctgccaacag tataaaagtt acccgctcac attcggcgga    300
gggaccaaag tggatatcaa acgt                                          324

<210> SEQ ID NO 112
<211> LENGTH: 348
<212> TYPE: DNA
<213> ORGANISM: Artificial Sequence
<220> FEATURE:
<223> OTHER INFORMATION: VH of 75H VH1-18

<400> SEQUENCE: 112
caggtacagc tggtgcagtc tggagctgag gtgaagaagc ctggggcctc agtgaaggtc    60
tcctgcaagg cttctggtta cacctttacc agctacggta tcagctgggt gcgacaggcc   120
cctggacaag gcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagggacc    300 tactacatg acgtctgggg caaagggacc acggtcaccg tctcgagc                 348

<210> SEQ ID NO 113
<211> LENGTH: 321
<212> TYPE: DNA
<213> ORGANISM: Artificial Sequence
<220> FEATURE:
<223> OTHER INFORMATION: VL of 75L VK1-12

<400> SEQUENCE: 113
gacatccaga tgacccagtc tccatcttcc gtgactgcat ctgtaggaga cagagtcagc    60
atcacttgtc gggcgaatca ggatattact tggttagtct ggtatcagca gaaaccaggg   120 aaagcccta agttcctgat gtctggtgca tccagttcgc aaggtggggc cccatcaagg    180
ttcagcgtca gtgaatctgg gacagacttc actctcacca tcagcagcct gcagccggaa    240
gattttgcaa cttactattg tcaacaggct gacagatatc cgctcacttt cggcggaggg    300
accaaggtgg agatcaaacg t                                             321

<210> SEQ ID NO 114
<211> LENGTH: 363
<212> TYPE: DNA
<213> ORGANISM: Artificial Sequence
<220> FEATURE:
<223> OTHER INFORMATION: VH of 290H VH3-30

<400> SEQUENCE: 114
caggtacagc tgttggagtc tgggggaggc gtggtccagc ctgggaggtc cctgagactc    60
tcctgtgcag cgtctggatt caccttcagt agatatggca tgcactgggt ccgccaggct   120
ccaggcaagg ggctggagtg ggtggcagtt atatcatatg atggaagcaa taaatactac    180
gcagactccg tgaagggccg attcaccatc tccagagaca attccaagaa cacgctgtat    240
ctgcaaatga acagcctgag agctgaggac acggctgtgt attactgtgc gagaggggat    300
agtagtgggt tcttgaatgc ttttgatatc tggggccaag gacaatggt caccgtctcg    360 agc                                                                 363

<210> SEQ ID NO 115
<211> LENGTH: 324
<212> TYPE: DNA
<213> ORGANISM: Artificial Sequence
<220> FEATURE:
<223> OTHER INFORMATION: VL of 290L VK1-33
```

-continued

```
<400> SEQUENCE: 115
gtcatctgga tgacccagtc tccatcctcc ctgtctgcat ctgtaggaga cagagtcacc          60
atcacttgcc aggcgagtca ggacattagc aactatttaa attggtatca gcagaaacca         120
gggaaagccc ctaagctcct gatctacgat gcatccaatt tggaaacagg ggtcccatca         180
aggttcagtg gaagtggatc tgggacagat tttactttca ccatcagcag cctgcagcct         240
gaagatattg caacatatta ctgtcaacag tatgataatc tccccctcac tttcggcgga         300
gggaccaaag tggatatcaa acgt                                               324
```

MONOCLONAL ANTIBODIES AND ANTIGEN BINDING FRAGMENTS THEREOF FOR SUPPRESSING CD73 IMMUNE CHECKPOINT AND USES THEREOF

CROSS-REFERENCE TO RELATED APPLICATIONS

This application claims priority under 35 U.S.C. § 119 to KR Appl. No. 10-2020-0043607 filed Apr. 9, 2020 and KR Appl. No. 10-2020-0144595 filed Nov. 2, 2020, the disclosures of which are incorporated by reference herein in their entirety.

REFERENCE TO SEQUENCE LISTING SUBMITTED ELECTRONICALLY

The content of the electronically submitted sequence listing in ASCII text file (Name: 2662-0003US01_SEQL.ST25; Size: 49,152 bytes; and Date of Creation: Jan. 22, 2026) filed with the application is incorporated herein by reference in its entirety.

FIELD

The present disclosure relates to monoclonal antibodies and antigen binding fragments thereof for suppressing a CD73 immune checkpoint and uses thereof.

BACKGROUND

Traditional cancer treatment methods include radiation therapy, chemotherapy, and anticancer drug treatment, and these methods are able to treat cancer by directly inhibiting growth of cancer. However, cancer cells are resistant to anticancer drugs, and the use of anticancer drugs can also attack cells other than cancer cells, causing side effects. To overcome these problems, immunotherapy has been developed as a new cancer therapy. Immunotherapy does not target cancer cells but targets immune cells, and induces immune cells to attack cancer cells.

Among immunotherapies, immune checkpoint blockades have recently attracted attention. Immune checkpoints are receptors that promote or suppress immune responses. Immune checkpoints are essential for regulating immune responses. Since immune checkpoints also work in cancer, cancer shows immune evasion through the immune checkpoints. Recently, many studies have been reported in which cancer was treated using immune checkpoints. First, antibodies against cytotoxic T-lymphocyte-associated antigen 4 (CTLA-4) and programmed cell death protein 1 (PD-1) immune checkpoints were developed, and showed increased survival rates in patients with melanoma. CTLA-4 and PD-1 immune checkpoint blockades have been used in a variety of cancers and have also shown efficacy in many cancers. However, treatment with CTLA-4 and PD-1 immune checkpoint blockades exhibited no efficacy in some patients. Therefore, many studies have been conducted on new immune checkpoints, and one of the immune evasion mechanisms in cancer is known to be high concentrations of immunosuppressive adenosine.

Meanwhile, "Cluster of Differentiation 73 (CD73)" is an ecto-nucleotidase that catalyzes dephosphorylation of 5'-nucleotides, and plays a role in converting adenosine monophosphate (AMP) to adenosine. CD73 exists in the form of a homodimer on the cell membrane via a GPI anchor, in which the monomer is 65 kDa, and the N-terminal and C-terminal domains are connected through a flexible helical linker. In other words, CD73 is involved in the production of adenosine, is overexpressed in cancer cells, and induces immunosuppression. Accordingly, there is a need for the development of new immune checkpoint blockades focusing on the concentration of immunosuppressive adenosine.

SUMMARY OF THE INVENTION

Disclosed herein are monoclonal antibodies or antigen binding fragments thereof comprising a heavy chain variable region comprising CDRH1 comprising an amino acid sequence of SEQ ID NO:1, 4, 7, 10, 14, or 17, CDRH2 comprising an amino acid sequence of SEQ ID NO:2, 5, 8, 11, 15, or 18, and CDRH3 comprising an amino acid sequence of SEQ ID NO:3, 6, 9, 12, 13, 16, or 19; and a light chain variable region comprising CDRL1 comprising an amino acid sequence of SEQ ID NO:20, 23, 26, or 29, CDRL2 comprising an amino acid sequence of SEQ ID NO:21, 24, 27, or 30, and CDRL3 comprising an amino acid sequence of SEQ ID NO:22, 25, 28, or 31.

In some embodiments, the monoclonal antibody or antigen binding fragment thereof can include a heavy chain variable region comprising CDRH1 comprising an amino acid sequence of SEQ ID NO:1, CDRH2 comprising an amino acid sequence of SEQ ID NO:2, and CDRH3 comprising an amino acid sequence of SEQ ID NO:3; and a light chain variable region comprising CDRL1 comprising an amino acid sequence of SEQ ID NO:20, CDRL2 comprising an amino acid sequence of SEQ ID NO:21, and CDRL3 comprising an amino acid sequence of SEQ ID NO:22; a heavy chain variable region comprising CDRH1 comprising an amino acid sequence of SEQ ID NO:4, CDRH2 comprising an amino acid sequence of SEQ ID NO:5, and CDRH3 comprising an amino acid sequence of SEQ ID NO:6; and a light chain variable region comprising CDRL1 comprising an amino acid sequence of SEQ ID NO:23, CDRL2 comprising an amino acid sequence of SEQ ID NO:24, and CDRL3 comprising an amino acid sequence of SEQ ID NO:25; a heavy chain variable region comprising CDRH1 comprising an amino acid sequence of SEQ ID NO:7, CDRH2 comprising an amino acid sequence of SEQ ID NO:8, and CDRH3 comprising an amino acid sequence of SEQ ID NO:9; and a light chain variable region comprising CDRL1 comprising an amino acid sequence of SEQ ID NO:26, CDRL2 comprising an amino acid sequence of SEQ ID NO:27, and CDRL3 comprising an amino acid sequence of SEQ ID NO:28; a heavy chain variable region comprising CDRH1 comprising an amino acid sequence of SEQ ID NO:10, CDRH2 comprising an amino acid sequence of SEQ ID NO:11, and CDRH3 comprising an amino acid sequence of SEQ ID NO:12 or 13; and a light chain variable region comprising CDRL1 comprising an amino acid sequence of SEQ ID NO:20, CDRL2 comprising an amino acid sequence of SEQ ID NO:21, and CDRL3 comprising an amino acid sequence of SEQ ID NO:22; a heavy chain variable region comprising CDRH1 comprising an amino acid sequence of SEQ ID NO:14, CDRH2 comprising an amino acid sequence of SEQ ID NO:15, and CDRH3 comprising an amino acid sequence of SEQ ID NO:16; and a light chain variable region comprising CDRL1 comprising an amino acid sequence of SEQ ID NO:20, CDRL2 comprising an amino acid sequence of SEQ ID NO:21, and CDRL3 comprising an amino acid sequence of SEQ ID NO:22; or a heavy chain variable region comprising CDRH1 comprising an amino acid sequence of SEQ ID NO:17, CDRH2 comprising an amino acid sequence of SEQ ID NO:18, and CDRH3 comprising an amino acid sequence of SEQ ID NO:19; and a light chain variable region comprising CDRL1 comprising an amino acid sequence of SEQ ID NO:29, CDRL2 comprising an amino acid sequence of SEQ ID NO:30, and CDRL3 comprising an amino acid sequence of SEQ ID NO:31.

In some embodiments, the antibodies or the antigen binding fragments thereof can comprise a heavy chain variable region comprising an amino acid sequence having at least 80%, at least 85%, at least 90%, at least 93%, at least 95%, at least 96%, at least 97%, at least 98%, at least 99%, or 100% identity to SEQ ID NO:32, 33, 34, 35, 36, 37, or 38; and a light chain variable region comprising an amino acid sequence having at least 80%, at least 85%, at least 90%, at least 93%, at least 95%, at least 96%, at least 97%, at least 98%, at least 99%, or 100% identity SEQ ID NO:39, 40, 41, or 42. In some embodiments, the antibodies or antigen binding fragments thereof can comprise a heavy chain variable region comprising an amino acid sequence of SEQ ID NO:32, 33, 34, 35, 36, 37, or 38; and a light chain variable region comprising an amino acid sequence of SEQ ID NO:39, 40, 41, or 42.

Also provided are monoclonal antibodies or antigen binding fragments thereof comprising a heavy chain variable region comprising CDRH1 comprising an amino acid sequence of SEQ ID NO:66, 69, 72, 75, or 78, CDRH2 comprising an amino acid sequence of SEQ ID NO:67, 70, 73, 76, or 79, and CDRH3 comprising an amino acid sequence of SEQ ID NO:68, 71, 74, 77, or 80; and a light chain variable region comprising CDRL1 comprising an amino acid sequence of SEQ ID NO:81, 84, 87, 90, or 93, CDRL2 comprising an amino acid sequence of SEQ ID NO:82, 85, 88, 91 or 94, and CDRL3 comprising an amino acid sequence of SEQ ID NO:83, 86, 89, 90, or 95.

In some embodiments, the antibody or antigen binding fragment thereof can include a heavy chain variable region comprising CDRH1 comprising an amino acid sequence of SEQ ID NO:66, CDRH2 comprising an amino acid sequence of SEQ ID NO:67, and CDRH3 comprising an amino acid sequence of SEQ ID NO:68; and a light chain variable region comprising CDRL1 comprising an amino acid sequence of SEQ ID NO:81, CDRL2 comprising an amino acid sequence of SEQ ID NO:82, and CDRL3 comprising an amino acid sequence of SEQ ID NO:83; a heavy chain variable region comprising CDRH1 comprising an amino acid sequence of SEQ ID NO:69, CDRH2 comprising an amino acid sequence of SEQ ID NO:70, and CDRH3 comprising an amino acid sequence of SEQ ID NO:71; and a light chain variable region comprising CDRL1 comprising an amino acid sequence of SEQ ID NO:84, CDRL2 comprising an amino acid sequence of SEQ ID NO:85, and CDRL3 comprising an amino acid sequence of SEQ ID NO:86; a heavy chain variable region comprising CDRH1 comprising an amino acid sequence of SEQ ID NO:72, CDRH2 comprising an amino acid sequence of SEQ ID NO:73, and CDRH3 comprising an amino acid sequence of SEQ ID NO:74; and a light chain variable region comprising CDRL1 comprising an amino acid sequence of SEQ ID NO:87, CDRL2 comprising an amino acid sequence of SEQ ID NO:88, and CDRL3 comprising an amino acid sequence of SEQ ID NO:89; a heavy chain variable region comprising CDRH1 comprising an amino acid sequence of SEQ ID NO:75, CDRH2 comprising an amino acid sequence of SEQ ID NO:76, and CDRH3 comprising an amino acid sequence of SEQ ID NO:77; and a light chain variable region comprising CDRL1 comprising an amino acid sequence of SEQ ID NO:90, CDRL2 comprising an amino acid sequence of SEQ ID NO:91, and CDRL3 comprising an amino acid sequence of SEQ ID NO:92; or a heavy chain variable region comprising CDRH1 comprising an amino acid sequence of SEQ ID NO:78, CDRH2 comprising an amino acid sequence of SEQ ID NO:79, and CDRH3 comprising an amino acid sequence of SEQ ID NO:80; and a light chain variable region comprising CDRL1 comprising an amino acid sequence of SEQ ID NO:93, CDRL2 comprising an amino acid sequence of SEQ ID NO:94, and CDRL3 comprising an amino acid sequence of SEQ ID NO:95.

Other aspects provide nucleic acids encoding the antibodies or antigen binding fragments thereof, expression vectors comprising the nucleic acids, and cells transformed with the expression vectors.

Provided herein are nucleic acids encoding the heavy chain variable region comprising an amino acid sequence having at least 80%, at least 85%, at least 90%, at least 93%, at least 95%, at least 96%, at least 97%, at least 98%, at least 99%, or 100% identity to SEQ ID NO:32, 33, 344, 35, 36, 37, or 38 and nucleic acids encoding the light chain variable region comprising an amino acid sequence having at least 80%, at least 85%, at least 90%, at least 93%, at least 95%, at least 96%, at least 97%, at least 98%, at least 99%, or 100% identity to SEQ ID NO:39, 40, 41, or 42. Also provided herein are nucleic acids encoding the heavy chain variable region of SEQ ID NO:32, 33, 344, 35, 36, 37, or 38 and nucleic acids encoding the light chain variable region of SEQ ID NO:39, 40, 41, or 42.

Provided are nucleic acids encoding the heavy chain variable region of SEQ ID NO:32 and nucleic acids encoding the light chain variable region of SEQ ID NO:39, or nucleic acids encoding the heavy chain variable region of SEQ ID NO:33 and nucleic acids encoding the light chain variable region of SEQ ID NO:40. For example, the nucleic acid encoding the heavy chain variable region of SEQ ID NO:32 can be represented by SEQ ID NO:43, and the nucleic acid encoding the light chain variable region of SEQ ID NO:39 can be represented by SEQ ID NO:44. In some embodiments, provided are nucleic acids encoding the heavy chain variable region of SEQ ID NO:32 or SEQ ID NO:33, and nucleic acids encoding the light chain variable region of SEQ ID NO:39 or SEQ ID NO:40. Further, the nucleic acid encoding the heavy chain variable region of SEQ ID NO:33 can be represented by SEQ ID NO:45, and the nucleic acid encoding the light chain variable region of SEQ ID NO:40 can be represented by SEQ ID NO:46.

Further, provided are nucleic acids encoding the heavy chain variable region comprising an amino acid sequence having at least 80%, at least 85%, at least 90%, at least 93%, at least 95%, at least 96%, at least 97%, at least 98%, at least 99%, or 100% identity to SEQ ID NO:96, 98, 100, 102, or 104 and nucleic acids encoding the light chain variable region comprising an amino acid sequence having at least 80%, at least 85%, at least 90%, at least 93%, at least 95%, at least 96%, at least 97%, at least 98%, at least 99%, or 100% identity to SEQ ID NO:97, 99, 101, 103, or 105. Further, provided are nucleic acids encoding the heavy chain variable region of SEQ ID NO:96, 98, 100, 102, or 104 and nucleic acids encoding the light chain variable region of SEQ ID NO:97, 99, 101, 103, or 105.

Provided are nucleic acids encoding the heavy chain variable region of SEQ ID NO:96 and nucleic acids encoding the light chain variable region of SEQ ID NO:97, nucleic acids encoding the heavy chain variable region of SEQ ID NO:98 and nucleic acids encoding the light chain variable region of SEQ ID NO:99, nucleic acids encoding the heavy chain variable region of SEQ ID NO:100 and nucleic acids encoding the light chain variable region of SEQ ID NO:101, nucleic acids encoding the heavy chain variable region of SEQ ID NO:102 and nucleic acids encoding the light chain variable region of SEQ ID NO:103, or nucleic acids encoding the heavy chain variable region of SEQ ID NO:104 and nucleic acids encoding the light chain variable region of SEQ ID NO:105. For example, the nucleic acid encoding the heavy chain variable region of SEQ ID NO:96 can be represented by SEQ ID NO:106, and the nucleic acid encoding the light chain variable region of SEQ ID NO:97 can be represented by SEQ ID NO:107. The nucleic acid encoding the heavy chain variable region of SEQ ID NO:98 can be represented by SEQ ID NO:108, and the nucleic acid encoding the light chain variable region of SEQ ID NO:99 can be represented by SEQ ID NO:109. The nucleic acid encoding the heavy chain variable region of SEQ ID NO:100 can be represented by SEQ ID NO:110, and the nucleic acid encoding the light chain variable region of SEQ ID NO:101 can be represented by SEQ ID NO:111. The nucleic acid encoding the heavy chain variable region of SEQ ID NO:102 can be represented by SEQ ID NO:112, and the nucleic acid encoding the light chain variable region of SEQ ID NO:103 can be represented by SEQ ID NO:113. The nucleic acid encoding the heavy chain variable region of SEQ ID NO:104 can be represented by SEQ ID NO:114, and the nucleic acid encoding the light chain variable region of SEQ ID NO:105 can be represented by SEQ ID NO: 115.

Further, provided are nucleic acids encoding the heavy chain variable region comprising a nucleotide sequence having at least 80%, at least 85%, at least 90%, at least 93%, at least 95%, at least 96%, at least 97%, at least 98%, at least 99%, or 100% identity to SEQ ID NO:106, 108, 110, 112, or 114 and nucleic acids encoding the light chain variable region comprising a nucleotide sequence having at least 80%, at least 85%, at least 90%, at least 93%, at least 95%, at least 96%, at least 97%, at least 98%, at least 99%, or 100% identity to SEQ ID NO:107, 109, 111, 113, or 115.

Also disclosed are compositions for preventing or treating cancer, the composition comprising the antibody or the antigen binding fragment thereof disclosed herein. In some embodiments, the composition can further comprise an immune checkpoint blockade or a chemotherapeutic agent.

Also disclosed are methods of treating cancer in a subject in need thereof, comprising administering the monoclonal antibody or antigen binding fragment thereof disclosed herein to the subject. In some embodiments, the cancer is a CD74 overexpressing cancer. In some embodiments, the cancer is breast cancer, triple-negative breast cancer (TBNC), pancreatic colorectal cancer, ovarian cancer, gastric cancer, bladder cancer, leukemia, prostate cancer, malignant melanoma, cancer, esophageal cancer, stomach cancer, head and neck cancer, lung cancer, or kidney cancer.

Also disclosed herein are uses of the monoclonal antibodies and antigen binding fragments thereof disclosed herein for the treatment of cancer in subjects in need thereof. Also disclosed herein are the monoclonal antibodies and antigen binding fragments thereof disclosed herein for use in the treatment of cancer in subjects in need thereof. Also disclosed herein are the use of the monoclonal antibodies and antigen binding fragments thereof disclosed herein for the manufacture of medicaments for treatment of cancer in subjects in need thereof.

BRIEF DESCRIPTION OF THE DRAWINGS

The above and other aspects, features, and advantages of certain embodiments of the disclosure will be more apparent from the following description taken in conjunction with the accompanying drawings, in which:

FIGS. 4A-4D show graphs showing a comparison of water-soluble CD73-binding abilities of APBA2-01 and APBA2-02 antibodies, wherein FIGS. 4A to 4D represent ELISA results of human, monkey, rat, and mouse CD73, respectively;

DETAILED DESCRIPTION OF THE INVENTION

Figure 1:
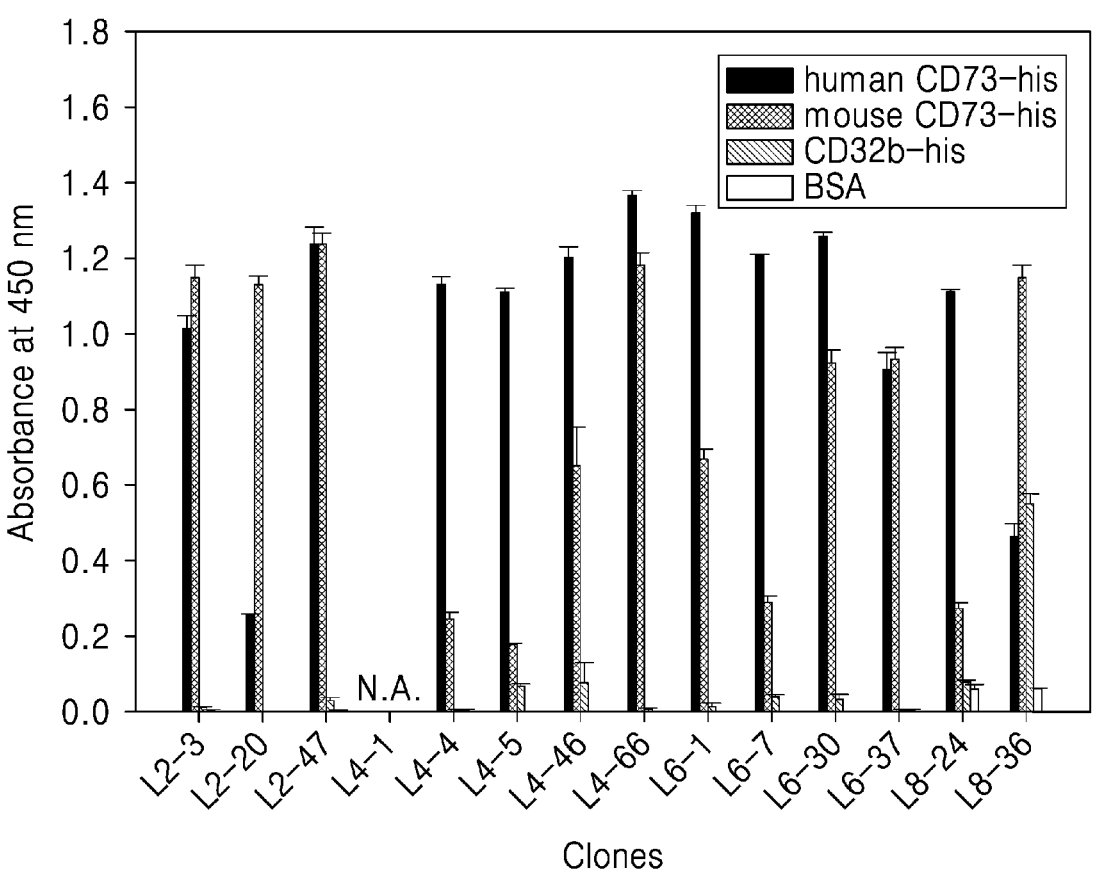
FIG. 1 is a graph showing CD73-binding ability of anti-CD73 antibodies which were selected through biopanning, wherein CD73 binding of phage antibodies was examined by measuring absorbance at a wavelength of 450 nm, and the standard deviation of data is indicated by error bars.

Disclosed herein are monoclonal antibodies or an antigen binding fragments thereof that bind to Cluster of Differentiation 73 (CD73).

Also disclosed herein are nucleic acids encoding the monoclonal antibodies or antigen binding fragments thereof, expression vectors comprising the nucleic acids, and cells transformed with the expression vectors.

Also disclosed herein are compositions for preventing or treating cancer, the compositions comprising the monoclonal antibodies or antigen binding fragments thereof.

Additional aspects will be set forth in part in the description which follows and, in part, will be apparent from the description, or can be learned by practice of the presented embodiments of the disclosure.

Disclosed herein are monoclonal antibodies or antigen binding fragments thereof comprising a heavy chain variable region comprising CDRH1 comprising an amino acid sequence of SEQ ID NO:1, 4, 7, 10, 14, or 17, CDRH2 comprising an amino acid sequence of SEQ ID NO:2, 5, 8, 11, 15, or 18, and CDRH3 comprising an amino acid sequence of SEQ ID NO:3, 6, 9, 12, 13, 16, or 19; and a light chain variable region comprising CDRL1 comprising an amino acid sequence of SEQ ID NO:20, 23, 26, or 29, CDRL2 comprising an amino acid sequence of SEQ ID NO:21, 24, 27, or 30, and CDRL3 comprising an amino acid sequence of SEQ ID NO:22, 25, 28, or 31.

In some embodiments, the monoclonal antibody or antigen binding fragment thereof can include a heavy chain variable region comprising CDRH1 comprising an amino acid sequence of SEQ ID NO:1, CDRH2 comprising an amino acid sequence of SEQ ID NO:2, and CDRH3 comprising an amino acid sequence of SEQ ID NO:3; and a light chain variable region comprising CDRL1 comprising an amino acid sequence of SEQ ID NO:20, CDRL2 comprising an amino acid sequence of SEQ ID NO:21, and CDRL3 comprising an amino acid sequence of SEQ ID NO:22; a heavy chain variable region comprising CDRH1 comprising an amino acid sequence of SEQ ID NO:4, CDRH2 comprising an amino acid sequence of SEQ ID NO:5, and CDRH3 comprising an amino acid sequence of SEQ ID NO:6; and a light chain variable region comprising CDRL1 comprising an amino acid sequence of SEQ ID NO:23, CDRL2 comprising an amino acid sequence of SEQ ID NO:24, and CDRL3 comprising an amino acid sequence of SEQ ID NO:25; a heavy chain variable region comprising CDRH1 comprising an amino acid sequence of SEQ ID NO:7, CDRH2 comprising an amino acid sequence of SEQ ID NO:8, and CDRH3 comprising an amino acid sequence of SEQ ID NO:9; and a light chain variable region comprising CDRL1 comprising an amino acid sequence of SEQ ID NO:26, CDRL2 comprising an amino acid sequence of SEQ ID NO:27, and CDRL3 comprising an amino acid sequence of SEQ ID NO:28; a heavy chain variable region comprising CDRH1 comprising an amino acid sequence of SEQ ID NO:10, CDRH2 comprising an amino acid sequence of SEQ ID NO:11, and CDRH3 comprising an amino acid sequence of SEQ ID NO:12 or 13; and a light chain variable region comprising CDRL1 comprising an amino acid sequence of SEQ ID NO:20, CDRL2 comprising an amino acid sequence of SEQ ID NO:21, and CDRL3 comprising an amino acid sequence of SEQ ID NO:22; a heavy chain variable region comprising CDRH1 comprising an amino acid sequence of SEQ ID NO:14, CDRH2 comprising an amino acid sequence of SEQ ID NO:15, and CDRH3 comprising an amino acid sequence of SEQ ID NO:16; and a light chain variable region comprising CDRL1 comprising an amino acid sequence of SEQ ID NO:20, CDRL2 comprising an amino acid sequence of SEQ ID NO:21, and CDRL3 comprising an amino acid sequence of SEQ ID NO:22; or a heavy chain variable region comprising CDRH1 comprising an amino acid sequence of SEQ ID NO:17, CDRH2 comprising an amino acid sequence of SEQ ID NO:18, and CDRH3 comprising an amino acid sequence of SEQ ID NO:19; and a light chain variable region comprising CDRL1 comprising an amino acid sequence of SEQ ID NO:29, CDRL2 comprising an amino acid sequence of SEQ ID NO:30, and CDRL3 comprising an amino acid sequence of SEQ ID NO:31.

In some embodiments, the antibodies or the antigen binding fragments thereof can comprise a heavy chain variable region comprising an amino acid sequence having at least 80%, at least 85%, at least 90%, at least 93%, at least 95%, at least 96%, at least 97%, at least 98%, at least 99%, or 100% identity to SEQ ID NO:32, 33, 34, 35, 36, 37, or 38; and a light chain variable region comprising an amino acid sequence having at least 80%, at least 85%, at least 90%, at least 93%, at least 95%, at least 96%, at least 97%, at least 98%, at least 99%, or 100% identity SEQ ID NO:39, 40, 41, or 42. In some embodiments, the antibodies or antigen binding fragments thereof can comprise a heavy chain variable region comprising an amino acid sequence of SEQ ID NO:32, 33, 34, 35, 36, 37, or 38; and a light chain variable region comprising an amino acid sequence of SEQ ID NO:39, 40, 41, or 42.

Also provided are monoclonal antibodies or antigen binding fragments thereof comprising a heavy chain variable region comprising CDRH1 comprising an amino acid sequence of SEQ ID NO:66, 69, 72, 75, or 78, CDRH2 comprising an amino acid sequence of SEQ ID NO:67, 70, 73, 76, or 79, and CDRH3 comprising an amino acid sequence of SEQ ID NO:68, 71, 74, 77, or 80; and a light chain variable region comprising CDRL1 comprising an amino acid sequence of SEQ ID NO:81, 84, 87, 90, or 93, CDRL2 comprising an amino acid sequence of SEQ ID NO:82, 85, 88, 91 or 94, and CDRL3 comprising an amino acid sequence of SEQ ID NO:83, 86, 89, 90, or 95.

In some embodiments, the antibody or antigen binding fragment thereof can include a heavy chain variable region comprising CDRH1 comprising an amino acid sequence of SEQ ID NO:66, CDRH2 comprising an amino acid sequence of SEQ ID NO:67, and CDRH3 comprising an amino acid sequence of SEQ ID NO:68; and a light chain variable region comprising CDRL1 comprising an amino acid sequence of SEQ ID NO:81, CDRL2 comprising an amino acid sequence of SEQ ID NO:82, and CDRL3 comprising an amino acid sequence of SEQ ID NO:83; a heavy chain variable region comprising CDRH1 comprising an amino acid sequence of SEQ ID NO:69, CDRH2 comprising an amino acid sequence of SEQ ID NO:70, and CDRH3 comprising an amino acid sequence of SEQ ID NO:71; and a light chain variable region comprising CDRL1 comprising an amino acid sequence of SEQ ID NO:84, CDRL2 comprising an amino acid sequence of SEQ ID NO:85, and CDRL3 comprising an amino acid sequence of SEQ ID NO:86; a heavy chain variable region comprising CDRH1 comprising an amino acid sequence of SEQ ID NO:72, CDRH2 comprising an amino acid sequence of SEQ ID NO:73, and CDRH3 comprising an amino acid sequence of SEQ ID NO:74; and a light chain variable region comprising CDRL1 comprising an amino acid sequence of SEQ ID NO:87, CDRL2 comprising an amino acid sequence of SEQ ID NO:88, and CDRL3 comprising an amino acid sequence of SEQ ID NO:89; a heavy chain variable region comprising CDRH1 comprising an amino acid sequence of SEQ ID NO:75, CDRH2 comprising an amino acid sequence of SEQ ID NO:76, and CDRH3 comprising an amino acid sequence of SEQ ID NO:77; and a light chain variable region comprising CDRL1 comprising an amino acid sequence of SEQ ID NO:90, CDRL2 comprising an amino acid sequence of SEQ ID NO:91, and CDRL3 comprising an amino acid sequence of SEQ ID NO:92; or a heavy chain variable region comprising CDRH1 comprising an amino acid sequence of SEQ ID NO:78, CDRH2 comprising an amino acid sequence of SEQ ID NO:79, and CDRH3 comprising an amino acid sequence of SEQ ID NO:80; and a light chain variable region comprising CDRL1 comprising an amino acid sequence of SEQ ID NO:93, CDRL2 comprising an amino acid sequence of SEQ ID NO:94, and CDRL3 comprising an amino acid sequence of SEQ ID NO:95.

Further, a heavy chain constant region and alight chain constant region of the antibody can be an antibody constant region of IgG, IgM, IgE, IgA, IgD, or a combination thereof.

The constant region can be derived from, for example, a constant region of IgG1 antibody.

In some embodiments, the antibody or antigen binding fragment thereof can have species cross-reactivity in individuals. The individual or subject can include vertebrates, and can include mammals, amphibians, reptiles, birds, etc., and the species can include, for example, humans (Homo sapiens), monkeys, rats, mice, etc. For example, the anti-CD73 antibody can inhibit transition of CD73 to its active structure or inhibits the enzymatic activity of CD73 by competitively binding with an inhibitor that binds to CD73. The anti-CD73 antibody can exhibit endocytic activity by binding to an epitope similar to that of a positive control MEDI9447 or CPI-006. Therefore, the antibody or antigen binding fragment thereof can have species cross-reactivity while specifically binding to CD73.

As used herein, the term "epitope" refers to a protein determinant to which an antibody is able to specifically bind. Epitopes usually consist of chemically active surface groupings of molecules, for example, amino acids or sugar side chains, and usually have specific three dimensional structural characteristics, as well as specific charge characteristics. Conformational and non-conformational epitopes are distinguished in that the binding to the former but not the latter is lost in the presence of denaturing solvents. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques. In some embodiments, the epitope of an antibody is determined using alanine scanning mutagenesis studies.

As used herein, the term "antibody" refers to a glycoprotein that inactivates antigens, such as viruses, bacteria, etc., and induces extracellular stimulation against microorganisms invading the body, and specifically, it refers to an immunoglobulin. The antibodies disclosed herein can include monoclonal antibodies, multispecific antibodies, human antibodies, humanized antibodies, chimeric antibodies, single-chain Fvs (scFv), single-chain antibodies, Fab fragments, F(ab') fragments, disulfide-linked Fvs (sdFv), and anti-idiotypic (anti-Id) antibodies, epitope-binding fragments of the antibodies, etc. Specifically, the antibody can be a monoclonal antibody and a fully human antibody or a human-mouse chimeric antibody. The monoclonal antibody refers to an antibody obtained from a population of substantially homogeneous antibodies, i.e., the individual antibodies including the population are identical except for possible naturally occurring mutations that can be present in minor amounts. Monoclonal antibodies are highly specific, and directed against a single antigenic epitope. The present disclosure relates to an anti-CD73 antibody, and therefore, unless otherwise indicated, the term 'antibody' as used herein without modification can refer to an anti-CD73 monoclonal antibody thatbinds to the epitope of CD73. An intact antibody form specifically binding to CD73 as well as an antigen binding fragment of the antibody molecule is included in the scope of the present disclosure. The intact antibody has a structure with two full-length light chains and two full-length heavy chains, wherein each light chain is connected with the heavy chain via a disulfide bond. A heavy chain constant region has gamma (γ), mu (μ), alpha (α), delta (δ) and epsilon (ε) types, which is sub-classified into gamma1 (γ1), gamma2 (γ2), gamma3 (γ3), gamma4 (γ4), alpha1 (α1), and alpha2 (α2). A light chain constant region has kappa (κ) and lambda (λ) types.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIAcore® or KinExA.

As used herein, the terms "immunospecifically binds," "immunospecifically recognizes," "specifically binds," and "specifically recognizes" are analogous terms in the context of antibodies and refer to molecules that bind to an antigen (e.g., epitope, immune complex, or binding partner of an antigen-binding site) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), or other assays known in the art. In some embodiments, molecules that immunospecifically bind to an antigen bind to the antigen with a $K_A$ that is at least 2 logs, 2.5 logs, 3 logs, 4 logs or greater than the $K_A$ when the molecules bind to another antigen.

In other embodiments, molecules that immunospecifically bind to an antigen do not cross react with other proteins under similar binding conditions. In some embodiments, molecules that immunospecifically bind to an antigen do not cross react with other proteins. In some embodiments, provided herein are monoclonal antibodies and antigen binding fragments thereof that bind to a specified antigen such as CD73 with higher affinity than to another unrelated antigen. In certain embodiments, provided herein are monoclonal antibodies and antigen binding fragments thereof that bind to a specified antigen such as CD73 with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In some embodiments, the extent of binding of are monoclonal antibodies and antigen binding fragments thereof described herein to an unrelated, protein is less than 10%, 15%, or 20% of the binding of the antibody to the specified antigen as measured by, e.g., a radioimmunoassay.

In some embodiments, provided herein are are monoclonal antibodies and antigen binding fragments thereof that bind to human CD73 with higher affinity than to another species of the antigen. In certain embodiments, provided herein are are monoclonal antibodies and antigen binding fragments thereof that bind to human CD73 with a 5%, 10%, 15%, 20%, 25%, 30%, 35%, 40%, 45%, 50%, 55%, 60%, 65%, 70% or higher affinity than to another species as measured by, e.g., a radioimmunoassay, surface plasmon resonance, or kinetic exclusion assay.

In some embodiments, the antibody has an Fv form (e.g., scFv), or an intact antibody form (IgG). In addition, the heavy chain constant region can be selected from isotypes including gamma (γ), mu (μ), alpha (α), delta (δ), and epsilon (ε) types. For example, the constant region is gamma1 (IgG1), gamma3 (IgG3), or gamma 4 (IgG4). The light chain constant region can be a kappa or lambda type.

As used herein, the term "heavy chain (HC or CH)" refers to a full-length heavy chain including a variable region domain VH including an amino acid sequence having a variable region (VR) sequence sufficient to impart specificity to an antigen and three constant region domains, CH1, CH2 and CH3, and a fragment thereof. In addition, the term "light chain (LC or CL)" refers to a full-length light chain including a variable region domain VL including an amino acid sequence having a variable region sequence sufficient to impart specificity to an antigen and a constant region domain CL, and a fragment thereof.

The "humanized" forms of non-human (e.g., murine) antibodies are chimeric antibodies which include minimal sequence derived from non-human immunoglobulin. For the most part, humanized antibodies are human immunoglobulins (recipient antibodies) in which hypervariable region residues of the recipient are replaced by hypervariable region residues from a non-human species (donor antibody) such as mouse, rat, rabbit or nonhuman primate having the desired specificity, affinity, and capacity.

The "human antibody" is a molecule derived from human immunoglobulin, and means that all of the amino acid sequences constituting the antibody including a complementarity determining region and a structural region are composed of human immunoglobulin. In some embodiments, the present disclosure relates to a fully human antibody capable of minimizing unintended immune responses.

The "chimeric antibody" includes a "chimeric" antibody (immunoglobulin) as well as a fragment of such antibody exhibiting the desired biological activity, in which a heavy chain and/or light chain is partly identical or homologous to the corresponding sequence in an antibody derived from a particular species or belonging to a particular antibody class or subclass, while the remaining chain(s) is/are identical or homologous to corresponding sequences in an antibody derived from another species or belonging to another antibody class or subclass.

The "antibody variable region" refers to the light and heavy chain regions of an antibody molecule including the amino acid sequences of a complementarity determining region (CDR, CDRH, or CDRL, i.e., CDRH1, CDRH2, and CDRH3) and a framework region (FR). VH refers to a variable region of heavy chain. VL refers to a variable region of light chain.

The "complementarity determining region" (CDR, CDRH, or CDRL, i.e., CDRL1, CDRL2, and CDRL3) refers to the amino acid residue of the antibody variable region, which is necessary for antigen binding. Each variable region generally has three CDR regions identified as CDR1, CDR2, and CDR3.

As used herein, the term "framework region" (FR) refers to a variable region residue other than a CDR residue. Each variable region generally has four FRs identified as FR1, FR2, FR3, and FR4.

As used herein, the term "antigen binding fragment" refers to a fragment of an antibody having antigen binding ability, including Fab, F(ab'), F(ab')2, Fv, etc. The "Fv" fragment is an antibody fragment including a complete antibody recognition and binding site. This region consists of a dimer, in which one heavy chain variable region and one light chain variable region are tightly covalently associated, for example, scFv. The "Fab" fragment includes the variable and constant regions of the light chain and the variable and first constant regions of the heavy chain (CH1). The F(ab')2 antibody fragment generally includes a pair of Fab fragments that are covalently linked near their carboxy ends by a hinge cysteine therebetween. The "single chain Fv" or "scFv" antibody fragment includes VH and VL domains of an antibody, wherein these domains are present in a single polypeptide chain. The Fv polypeptide further includes a polypeptide linker between the VH and VL domains which enables the scFv to form the desired structure for antigen binding.

Fv is a minimal antibody segment only having a heavy chain variable region and a light chain variable region, and a recombinant technique producing an Fv fragment is disclosed in WO88/10649, WO88/106630, WO88/07085, WO88/07086, and WO88/09344. In two-chain Fv, a heavy chain variable region and a light chain variable region are connected by a non-covalent bond, and in single-chain Fv (scFv), a heavy chain variable region and a light chain variable region are generally connected by a covalent bond via a peptide linker, or directly connected to the C-terminal, thereby forming a structure such as a dimer like two-chain Fv. Such an antibody fragment can be obtained using a protein hydrolase (for example, Fab can be obtained by digesting an entire antibody with papain, and a F(ab')2 fragment can be obtained by digesting the antibody with pepsin), and the antibody fragment can also be prepared through a genetic recombinant technique.

As used herein, the term "phage display" refers to a technique that displays a fusion protein by fusing a mutant polypeptide and at least a part of a coat protein on the surface of a phage, for example, a fibrous phage particle. The phage display is useful for targeting a large library of randomized protein variants to quickly and efficiently classify sequences that bind to target antigens with high affinity. Displaying peptides and protein libraries on phage has been used to screen millions of polypeptides to identify polypeptides with specific binding properties.

The phage display technique has provided a powerful tool for generating and screening novel proteins that bind to specific ligands (e.g., antigens). By using the phage display technique, a large library of protein variants can be generated, and sequences binding to target antigens with high affinity can be rapidly classified. A nucleic acid encoding a mutant polypeptide is fused with a nucleic acid sequence encoding a viral coat protein, e.g., a gene III protein or a gene VIII protein. A monovalent phage display system has been developed, in which a nucleic acid sequence encoding a protein or polypeptide is fused with a nucleic acid sequence encoding a part of the gene III protein. In the monovalent phage display system, the gene fusion is expressed at a low level, and the wild-type gene III protein is also expressed, thereby maintaining infectivity of particles.

Demonstrating expression of peptides on the fibrous phage surface and expression of functional antibody fragments in the peripheral cytoplasm of *E. coli* is important in developing antibody phage display libraries. Libraries of antibodies or antigen-binding polypeptides have been prepared in a number of ways, for example, by altering a single gene by inserting a random DNA sequence or by cloning a related genic line. The library can be screened for expression of antibodies or antigen binding proteins with the desired characteristics.

The phage display technique has several advantages over common hybridomas and recombinant methods for producing antibodies with the desired characteristics. This technique allows generation of a large antibody library having various sequences in a short time without the use of animals. The production of hybridomas or humanized antibodies can take several months to prepare. Further, the phage antibody library can produce antibodies against antigens that are toxic or have low antigenicity since no immunity is required. The phage antibody library can also be used to generate and identify novel therapeutic antibodies.

A technology can be used in which human antibodies are generated from human germline sequences or virgin B-cell Ig repertoires immunized or non-immunized using a phage display library. Various lymphatic tissues can be used to prepare virgin or non-immune antigen-binding libraries.

Techniques for identifying and separating high affinity antibodies from a phage display library are important for separating new therapeutic antibodies. The separation of high affinity antibodies from the library can depend on the size of the library, production efficiency in bacterial cells, and library diversity. The size of the library is reduced by inefficient production due to improper folding of an antibody or antigen binding protein and the presence of the stop codon. Expression in bacterial cells can be inhibited when an antibody or antigen binding domain is not properly folded. The expression can be improved by alternately mutating residues on the surface of a variable/constant interface or selected CDR residues. A sequence of the framework region is one element to provide appropriate folding when antibody phage libraries are generated in bacterial cells.

It is important to generate various libraries of an antibody or antigen binding proteins in high affinity antibody separation. The CDR3 region has been found to often participate in antigen binding. The CDR3 region on a heavy chain considerably varies in terms of size, sequence, and structural steric conformation so that various libraries can be prepared using the CDR3 region.

Further, diversity can be generated by randomizing the CDR regions of the variable heavy and light chains using all 20 amino acids at each position. The use of all 20 amino acids results in an increased variability of variant antibody sequences and an increased chance of identifying new antibodies.

The antibody or antibody fragment of the present disclosure can include, within the scope of specifically recognizing CD73, the sequence of the anti-CD73 antibody described herein as well as biological equivalents thereof. For example, the amino acid sequence of the antibody can be additionally modified to further improve the binding affinity and/or other biological properties of the antibody. Such modifications include, for example, deletion, insertion, and/or substitution of the amino acid sequence residues of the antibody. Such amino acid variations are made based on the relative similarity of amino acid side chain substituents, for example, hydrophobicity, hydrophilicity, charge, size, etc. By analysis of the size, shape, and type of amino acid side chain substituents, it is recognized that each of arginine, lysine, and histidine is a positively charged residue; alanine, glycine, and serine have similar sizes; and phenylalanine, tryptophan, and tyrosine have similar shapes. Based on these considerations, it is thus found that arginine, lysine, and histidine; alanine, glycine, and serine; and phenylalanine, tryptophan and tyrosine, respectively, are biologically functional equivalents.

In introduction of mutations, the hydropathic index of amino acids can be considered. Each amino acid is assigned a hydrophobic index according to its hydrophobicity and charge: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The hydrophobic amino acid index is very important in imparting the interactive biological function of proteins. It is well known that substitution with an amino acid having a similar hydrophobic index can retain similar biological activities. When a mutation is introduced with reference to a hydrophobic index, the substitution is made between amino acids showing a hydrophobic index difference specifically within ±2, more specifically within ±1, even more specifically within ±0.5.

Meanwhile, it is also well known that the substitution between amino acids with similar hydrophilicity values leads to proteins with equivalent biological activity. As disclosed in U.S. Pat. No. 4,554,101, the following hydrophilicity values are assigned to each amino acid residue: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). Amino acid substitution in proteins that do not totally alter the activity of the molecule is known in the art (H. Neurath, R.L.Hill, The Proteins, Academic Press, New York, 1979). The substitution occurs the most commonly between amino acid residues, e.g., Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly.

In some embodiments, the position of one or more CDRs along the VH (e.g., CDR1, CDR2, or CDR3) and/or VL (e.g., CDR1, CDR2, or CDR3) region of an antibody described herein can vary by one, two, three, four, five, or six amino acid positions so long as immunospecific binding to an antigen is maintained (e.g., substantially maintained, for example, at least 50%, at least 60%, at least 70%, at least 80%, at least 90%, at least 95%). For example, the position defining a CDR of an antibody described herein can vary by shifting the N-terminal and/or C-terminal boundary of the CDR by one, two, three, four, five, or six amino acids, relative to the CDR position of a monoclonal antibody or antigen binding fragment thereof described herein, so long as immunospecific binding to the antigen(s) is maintained (e.g., substantially maintained, for example, at least 50%, at least 60%, at least 70%, at least 80%, at least 90%, at least 95%). In other embodiments, the length of one or more CDRs along the VH (e.g., CDR1, CDR2, or CDR3) and/or VL (e.g., CDR1, CDR2, or CDR3) region of an antibody described herein can vary (e.g., be shorter or longer) by one, two, three, four, five, or more amino acids, so long as immunospecific binding to the antigen(s) is maintained (e.g., substantially maintained, for example, at least 50%, at least 60%, at least 70%, at least 80%, at least 90%, at least 95%).

In some embodiments, a CDRL1, CDRL2, CDRL3, CDRH1, CDRH2, and/or CDRH3 described herein can be one, two, three, four, five or more amino acids shorter than one or more of the CDRs described herein so long as immunospecific binding to the antigen(s) is maintained (e.g., substantially maintained, for example, at least 50%, at least 60%, at least 70%, at least 80%, at least 90%, at least 95%). In other embodiments, a CDRL1, CDRL2, CDRL3, CDRH1, CDRH2, and/or CDRH3 described herein can be one, two, three, four, five or more amino acids longer than one or more of the CDRs described herein so long as immunospecific binding to the antigen(s) is maintained (e.g., substantially maintained, for example, at least 50%, at least 60%, at least 70%, at least 80%, at least 90%, at least 95%). In other embodiments, the amino terminus of a CDRL1, CDRL2, CDRL3, CDRH1, CDRH2, and/or CDRH3 described herein can be extended by one, two, three, four, five or more amino acids compared to one or more of the CDRs described herein so long as immunospecific binding to the antigen(s) is maintained (e.g., substantially maintained, for example, at least 50%, at least 60%, at least 70%, at least 80%, at least 90%, at least 95%). In other embodiments, the carboxy terminus of a CDRL1, CDRL2, CDRL3, CDRH1, CDRH2, and/or CDRH3 described herein can be extended by one, two, three, four, five or more amino acids compared to one or more of the CDRs described herein so long as immunospecific binding to the antigen(s) is maintained (e.g., substantially maintained, for example, at least 50%, at least 60%, at least 70%, at least 80%, at least 90%, at least 95%). In other embodiments, the amino terminus of a CDRL1, CDRL2, CDRL3, CDRH1, CDRH2, and/or CDRH3 described herein can be shortened by one, two, three, four, five or more amino acids compared to one or more of the CDRs described herein so long as immunospecific binding to the antigen(s) is maintained (e.g., substantially maintained, for example, at least 50%, at least 60%, at least 70%, at least 80%, at least 90%, at least 95%). In some embodiments, the carboxy terminus of a CDRL1, CDRL2, CDRL3, CDRH1, CDRH2, and/or CDRH3 described herein can be shortened by one, two, three, four, five or more amino acids compared to one or more of the CDRs described herein so long as immunospecific binding to the antigen(s) is maintained (e.g., substantially maintained, for example, at least 50%, at least 60%, at least 70%, at least 80%, at least 90%, at least 95%). Any method known in the art can be used to ascertain whether immunospecific binding to the antigen(s) is maintained, for example, the binding assays and conditions described in the "Examples" section herein.

The determination of percent identity between two sequences (e.g., amino acid sequences or nucleic acid sequences) can also be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877. Such an algorithm is incorporated into the NBLAST and XBLAST programs of Altschul S F et al., (1990) J Mol Biol 215: 403. BLAST nucleotide searches can be performed with the NBLAST nucleotide program parameters set, e.g., for score=100, wordlength=12 to obtain nucleotide sequences homologous to nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the world-wide web, ncbi.nlm.nih.gov). Another specific, nonlimiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

Other aspects provide nucleic acids encoding the antibodies or antigen binding fragments thereof, an expression vectors comprising the nucleic acids, and cells transformed with the expression vectors.

Provided herein are nucleic acids encoding the heavy chain variable region comprising an amino acid sequence having at least 80%, at least 85%, at least 90%, at least 93%, at least 95%, at least 96%, at least 97%, at least 98%, at least 99%, or 100% identity to SEQ ID NO:32, 33, 344, 35, 36, 37, or 38 and nucleic acids encoding the light chain variable region comprising an amino acid sequence having at least 80%, at least 85%, at least 90%, at least 93%, at least 95%, at least 96%, at least 97%, at least 98%, at least 99%, or 100% identity to SEQ ID NO:39, 40, 41, or 42. Also provided herein are nucleic acids encoding the heavy chain variable region of SEQ ID NO:32, 33, 344, 35, 36, 37, or 38 and nucleic acids encoding the light chain variable region of SEQ ID NO:39, 40, 41, or 42.

In some embodiments, provided are nucleic acids encoding the heavy chain variable region of SEQ ID NO:32 and nucleic acids encoding the light chain variable region of SEQ ID NO:39, or nucleic acids encoding the heavy chain variable region of SEQ ID NO:33 and nucleic acids encoding the light chain variable region of SEQ ID NO:40. For example, the nucleic acid encoding the heavy chain variable region of SEQ ID NO:32 can be represented by SEQ ID NO:43, and the nucleic acid encoding the light chain variable region of SEQ ID NO:39 can be represented by SEQ ID NO:44. In some embodiments, provided are nucleic acids encoding the heavy chain variable region of SEQ ID NO:32 or SEQ ID NO:33, and nucleic acids encoding the light chain variable region of SEQ ID NO:39 or SEQ ID NO:40. Further, the nucleic acid encoding the heavy chain variable region of SEQ ID NO:33 can be represented by SEQ ID NO:45, and the nucleic acid encoding the light chain variable region of SEQ ID NO:40 can be represented by SEQ ID NO:46.

Further, provided are nucleic acids encoding the heavy chain variable region comprising an amino acid sequence having at least 80%, at least 85%, at least 90%, at least 93%, at least 95%, at least 96%, at least 97%, at least 98%, at least 99%, or 100% identity to SEQ ID NO:96, 98, 100, 102, or 104 and nucleic acids encoding the light chain variable region comprising an amino acid sequence having at least 80%, at least 85%, at least 90%, at least 93%, at least 95%, at least 96%, at least 97%, at least 98%, at least 99%, or 100% identity to SEQ ID NO:97, 99, 101, 103, or 105. Further, provided are nucleic acids encoding the heavy chain variable region of SEQ ID NO:96, 98, 100, 102, or 104 and nucleic acids encoding the light chain variable region of SEQ ID NO:97, 99, 101, 103, or 105.

In some embodiments, provided are nucleic acids encoding the heavy chain variable region of SEQ ID NO:96 and nucleic acids encoding the light chain variable region of SEQ ID NO:97, nucleic acids encoding the heavy chain variable region of SEQ ID NO:98 and nucleic acids encoding the light chain variable region of SEQ ID NO:99, nucleic acids encoding the heavy chain variable region of SEQ ID NO:100 and nucleic acids encoding the light chain variable region of SEQ ID NO:101, nucleic acids encoding the heavy chain variable region of SEQ ID NO:102 and nucleic acids encoding the light chain variable region of SEQ ID NO:103, or nucleic acids encoding the heavy chain variable region of SEQ ID NO:104 and nucleic acids encoding the light chain variable region of SEQ ID NO:105. For example, the nucleic acid encoding the heavy chain variable region of SEQ ID NO:96 can be represented by SEQ ID NO:106, and the nucleic acid encoding the light chain variable region of SEQ ID NO:97 can be represented by SEQ ID NO:107. The nucleic acid encoding the heavy chain variable region of SEQ ID NO:98 can be represented by SEQ ID NO:108, and the nucleic acid encoding the light chain variable region of SEQ ID NO:99 can be represented by SEQ ID NO:109. The nucleic acid encoding the heavy chain variable region of SEQ ID NO:100 can be represented by SEQ ID NO:110, and the nucleic acid encoding the light chain variable region of SEQ ID NO:101 can be represented by SEQ ID NO:111. The nucleic acid encoding the heavy chain variable region of SEQ ID NO:102 can be represented by SEQ ID NO:112, and the nucleic acid encoding the light chain variable region of SEQ ID NO:103 can be represented by SEQ ID NO:113. The nucleic acid encoding the heavy chain variable region of SEQ ID NO:104 can be represented by SEQ ID NO:114, and the nucleic acid encoding the light chain variable region of SEQ ID NO:105 can be represented by SEQ ID NO:115.

Further, provided are nucleic acids encoding the heavy chain variable region comprising a nucleotide sequence having at least 80%, at least 85%, at least 90%, at least 93%, at least 95%, at least 96%, at least 97%, at least 98%, at least 99%, or 100% identity to SEQ ID NO:106, 108, 110, 112, or 114 and nucleic acids encoding the light chain variable region comprising a nucleotide sequence having at least 80%, at least 85%, at least 90%, at least 93%, at least 95%, at least 96%, at least 97%, at least 98%, at least 99%, or 100% identity to SEQ ID NO:107, 109, 111, 113, or 115.

The monoclonal antibodies or antigen binding fragments thereof can be recombinantly produced by isolating the nucleic acid encoding the antibody or antigen binding fragment thereof of the present disclosure. The nucleic acid is isolated and inserted into a replicable vector for further cloning (amplification of DNA) or further expression. In some embodiments, one or more of the nucleic acids disclosed herein can be inserted into one vector or each nucleic acids disclosed herein can be inserted into separate vectors. Based on this, in other aspects, the present disclosures relates to vectors comprising the nucleic acids disclosed herein.

As used herein, the term "nucleic acid" encompasses both DNA (gDNA and cDNA) and RNA molecules, and a nucleotide, which is a basic constituent unit of the nucleic acid, includes naturally derived nucleotides as well as analogues wherein sugar or base moieties are modified. The sequences of the nucleic acids encoding the heavy and light chain variable regions of the present disclosure can be modified. Such modification includes addition, deletion, or non-conservative or conservative substitution of nucleotides.

The DNA encoding the antibody can be easily separated or synthesized using common procedures (e.g., using an oligonucleotide probe capable of specifically binding to DNA encoding heavy and light chains of the antibody). A variety of vectors are available. Vector components generally include, but are not limited to, one or more of the following components: signal sequences, replication origins, one or more marker genes, enhancer elements, promoters, and transcription termination sequences.

As used herein, the term "vector" refers to a means for expressing target genes in host cells, and includes plasmid vectors; cosmid vectors; viral vectors such as bacteriophage vectors, adenovirus vectors, retroviral vectors, adeno-associated viral vectors, etc. The nucleic acids encoding the antibody in the vector is operably linked to a promoter.

The term "operably linked" means a functional linkage between a nucleotide expression regulatory sequence (e.g., promoter, signal sequence, or array of transcription regulator binding site) and another nucleotide sequence, and is regulated by transcription and/or translation of the nucleotide sequence.

When a prokaryotic cell is used as a host, the vector generally includes a potent promoter capable of conducting transcription (e.g., tac promoter, lac promoter, lacUV5 promoter, lpp promoter, pL$\lambda$ promoter, pR$\lambda$promoter, rac5 promoter, amp promoter, recA promoter, SP6 promoter, trp promoter, T7 promoter, etc.), a ribosome binding site for initiation of translation, and a transcription/translation termination sequence. In addition, for example, when a eukaryotic cell is used as a host, the vector includes a promoter (e.g., a metallothionein promoter, a $\beta$-actin promoter, a human hemoglobin promoter and a human muscle creatine promoter) derived from the genome of mammalian cells, or a promoter derived from an animal virus (e.g., adenovirus late promoter, vaccinia virus 7.5K promoter, SV40 promoter, cytomegalovirus (CMV) promoter, HSV tk promoter, mouse mammary tumor virus (MMTV) promoter, HIV LTR promoter, Moloney virus promoter, Epstein Barr virus (EBV) promoter, and Rous sarcoma virus (RSV) promoter, and generally has a polyadenylation sequence as a transcription termination sequence. Optionally, the vector can be fused with another sequence in order to facilitate purification of the antibody expressed therefrom. The sequence to be fused includes, for example, glutathione S-transferase (Pharmacia, USA), maltose-binding protein (NEB, USA), FLAG (IBI, USA), 6×His (hexahistidine; Qiagen, USA), etc. The vector includes antibiotic-resistant genes commonly used in the art as selectable markers, and examples thereof include genes resistant to ampicillin, gentamycin, carbenicillin, chloramphenicol, streptomycin, kanamycin, geneticin, neomycin, and tetracycline.

In still other aspects, the present disclosure provides cells transformed with the above-mentioned vector. The cells used to produce the antibodies or antigen binding fragments thereof disclosed herein can be prokaryote, yeast, or higher eukaryotic cells, but are not limited thereto. Prokaryotic host cells such as *Escherichia coli*, the genus *Bacillus* such as, *Bacillus subtilis* and *Bacillus thuringiensis, Streptomyces, Pseudomonas* (e.g., *Pseudomonas putida*), *Proteus mirabilis*, and *Staphylococcus* (e.g., *Staphylococcus carnosus*) can be used. However, interest in animal cells is the greatest, and examples of useful host cell lines include COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC 12, K562, PER.C6, SP2/0, NS-0, U20S, or HT1080, but are not limited thereto.

The present disclosure also provides methods of preparing the antibodies or antigen binding fragments thereof, the methods comprising (a) culturing the cells comprising the expression vectors; and (b) collecting the antibodies or antigen binding fragments thereof from the cultured cells. The cells can be cultured in various media. Any commercially available medium can be used as a culture medium without limitation. All other essential supplements wellknown to those skilled in the art can be included at appropriate concentrations. Culture conditions, for example, temperature and pH already have been used with host cells selected for expression, which will be apparent to those skilled in the art. The collecting of the antibody or antigen binding fragment thereof can be carried out, for example, by centrifugation or ultrafiltration to remove impurities and by purification of the resulting product using, for example, affinity chromatography. Other additional purification techniques, e.g., anion or cation exchange chromatography, hydrophobic interaction chromatography, and hydroxyapatite chromatography can be used.

Still other aspects provide compositions for preventing, improving, or treating cancer, the compositions comprising the antibodies or antigen binding fragments thereof. The compositions can be a pharmaceutical compositions or health functional foods. In some embodiments, the compositions can further include an immune checkpoint blockade or a chemotherapeutic agent. The immune checkpoint blockade can be, for example, an anti-CTLA-4 antibody, an anti-PD-1 antibody, an anti-PD-L1 antibody, etc., and the chemotherapeutic agent can be, for example, chemotherapy drugs, tyrosine kinase inhibitors, etc. In some embodiments, the composition can be administered in combination with a radiotherapeutic agent. The composition according to one aspect can have increased anticancer activity in various cancers expressing CD73, and thus can be used as a therapeutic agent for cancers.

For example, the composition can be a pharmaceutical composition for preventing or treating cancers, the composition comprising (a) a pharmaceutically effective amount of the antibody against CD73 or the antigen binding fragment thereof, and (b) a pharmaceutically acceptable carrier. Further, the present disclosure relates to a method of preventing or treating cancers in a subject in need thereof, the method comprising administering to the subject, an effective amount of the antibody against CD73 or the antigen binding fragment thereof according to the present disclosure.

In the compositions, the monoclonal antibodies or antigen binding fragments thereof as disclosed herein are used as active ingredients, and thus common descriptions between the two will be omitted.

As demonstrated in the following exemplary embodiments, the antibodies or antigen binding fragments thereof of the present disclosure bind to CD73 with high affinity to suppress migration of CD73-overexpressing cancer cells, and thus can be used in preventing or treating cancers. "Preventing" means any action that inhibits or delays progress of a cancer by administering the composition. "Treating" means suppression of development of a cancer, alleviation of a cancer, or elimination of a cancer.

A "CD73-overexpressing cancer" refers to a cancer having CD73 on the cancer cell surface at a significantly higher level, as compared with non-cancerous cells of the same tissue type. See, e.g., Hay, C. M. et al., OncoImmunol. 5:e1208875, 10 pages (2016), and Gao, Z-w. et al., BioMed Res. Intl. 2014:460654, 9 pages (2014). The cancer to which the composition is applied is a CD73-overexpressing cancer, for example, breast cancer, colon cancer, glioblastoma, cerebrospinal tumor, head and neck cancer, lung cancer, thymoma, esophageal cancer, liver cancer, pancreatic cancer, biliary tract cancer, kidney cancer, bladder cancer, prostate cancer, testicular cancer, germ cell tumor, ovarian cancer, cervical cancer, endometrial cancer, lymphoma, acute leukemia, chronic leukemia, multiple myeloma, sarcoma, malignant melanoma, skin cancer, etc. In some embodiments, the cancer is breast cancer, triple-negative breast cancer (TBNC), pancreatic colorectal cancer, ovarian cancer, gastric cancer, bladder cancer, leukemia, prostate cancer, malignant melanoma, cancer, esophageal cancer, stomach cancer, head and neck cancer, lung cancer, or kidney cancer.

Still other aspects provide compositions for suppressing metastasis or invasion of cancer cells, the composition comprising the antibody against CD73 or the antigen binding fragment thereof. Further, the present disclosure provides a method of suppressing metastasis or invasion of cancer cells in a subject in need thereof, the method comprising administering to the subject the monoclonal antibody against CD73 or the antigen binding fragment thereof.

Pharmaceutically acceptable carriers can be included in the compositions of the present disclosure, such as but not limited to lactose, dextrose, sucrose, sorbitol, mannitol, starch, acacia rubber, calcium phosphate, alginate, gelatin, calcium silicate, microcrystalline cellulose, polyvinylpyrrolidone, water, syrup, methylcellulose, methylhydroxybenzoate, propyl-hydroxybenzoate, talc, magnesium stearate, mineral oil, etc., but is not limited thereto. The compositions of the present disclosure can further include a lubricant, a wetting agent, a sweetener, a flavoring agent, an emulsifying agent, a suspending agent, a preservative, etc., in addition to the components.

The pharmaceutical compositions of the present disclosure can be administered orally or parenterally. Parenteral administration can be carried out by intravenous injection, subcutaneous injection, intramuscular injection, intraperitoneal injection, endothelial administration, topical administration, intranasal administration, intrapulmonary administration, rectal administration, etc. In some embodiments, the compositions can be administered in the form of intravenous injection. Because a protein or peptide is digested when administered orally, a composition for oral administration should be formulated to coat or protect an active drug agent against degradation in stomach. Also, the pharmaceutical compositions can be administered by any device which can transport active substances to target cells.

The appropriate dosage of the compositions according to the present disclosure can vary depending on factors such as the formulation method, the administration method, a patient's age, body weight, sex, pathological condition, food, administration time, administration route, excretion rate, and reaction sensitivity. Thus, a commonly skilled physician can easily determine and prescribe a dosage that is effective for the desired treatment or prevention. For example, the daily dosage of the pharmaceutical composition of the present disclosure can be 0.0001 mg/kg to 100 mg/kg, 0.001 mg/kg to 50 mg/kg, 0.01 mg/kg to 25 mg/kg, 0.1 mg/kg to 10 mg/kg, 1 mg/kg to 5 mg/kg of body weight of the subject, or any ranges therein. As used herein, the term "pharmaceutically effective amount" refers to an amount sufficient to prevent or treat a cancer.

The pharmaceutical compositions of the present disclosure can be formulated using a pharmaceutically acceptable carrier and/or an excipient according to a method which can be easily carried out by those having ordinary skill in the art to which the present disclosure pertains so as to be provided in a unit dosage form or enclosed into a multi-dose container. Here, the formulations can be in the form of solutions, suspensions, or emulsions in oil or aqueous media, or in the form of extracts, grains, suppositories, powders, granules, tablets or capsules, and can additionally include dispersing or stabilizing agents.

The compositions of the present disclosure can be administered as an individual therapeutic agent or in combination with another therapeutic agent, and can be administered sequentially or simultaneously with an existing therapeutic agent.

In the health functional food for preventing or improving a cancer according to the present disclosure, when the antibody or antigen binding fragment thereof is used as an additive of the health functional food, it can be added as it is or together with other foods or food additives, and can be appropriately used according to a common method. A mixing amount of active ingredients can be appropriately determined according to the purposes of use, such as prevention, health, or treatment.

The preparations of the health functional food can include grains, granules, pills, tablets, capsules, as well as any of general foods or beverages.

The kind of the food is not particularly limited, and examples of foods to which the above substance can be added can include meats, sausages, bread, chocolates, candies, snacks, confectionery, pizzas, ramen, other noodles, gums, dairy products including ice cream, various soups, beverages, teas, drinks, alcoholic beverages and vitamin complexes, and can include all foods in the common sense.

In general, in preparation of foods or beverages, the antibody or antigen binding fragment thereof can be added in an amount of 15 parts by weight or less, specifically, 10 parts by weight or less, with respect to 100 parts by weight of raw materials. However, when ingested for a long period of time for health and hygiene purposes or for health control purposes, the amount can be below the above range. Further, the composition has no problem in terms of safety, because a fraction from a natural product is used. Thus, it can also be used in an amount in the above range or more.

Among the health functional foods according to the present disclosure, beverages can include various flavoring agents or natural carbohydrates as an additional component, as in ordinary beverages. The above-mentioned natural carbohydrate can be a monosaccharide such as glucose and fructose; a disaccharide such as maltose and sucrose; a polysaccharide such as dextrin and cyclodextrin; or sugar alcohol such as xylitol, sorbitol, and erythritol, etc. As the sweetening agent, a natural sweetening agent such as thaumatin and a stevia extract; a synthetic sweetening agent such as saccharin and aspartame, etc. can be used. A proportion of the natural carbohydrate can be about 0.01 g to about 0.04 g, and specifically, about 0.02 g to about 0.03 g, per 100 mL of the beverage according to the present disclosure.

In addition to the above-mentioned ingredients, the health functional food for preventing or improving a cancer according to the present disclosure can include various nutrients, vitamins, electrolytes, flavoring agents, colorants, pectic acid and salts thereof, alginic acid and salts thereof, organic acids, protective colloids, thickeners, pH adjusting agents, stabilizers, preservatives, glycerin, alcohol, carbonating agents used in carbonated beverages. In addition, the composition for improving cancer according to the present disclosure can include fruit flesh for preparing a natural fruit juice, a fruit juice beverage, or a vegetable beverage. These ingredients can be used alone or in a mixture. Proportions of such additives are not limited, but generally selected in a range of 0.01 part by weight to 0.1 part by weight with respect to 100 parts by weight of the health functional food of the present disclosure.

Still other aspects provide a composition for diagnosing a cancer, the composition comprising the antibody or antigen binding fragment thereof, and kits for diagnosing a cancer, the kits comprising the composition. The present disclosure also relates to a method of diagnosing a cancer by treating with the antibody against CD73 or the antigen binding fragment thereof according to the present disclosure.

The cancer can be diagnosed by measuring an expression level of CD73 in a sample through the antibody against CD73 according to the present disclosure. The expression level can be measured according to a common immunoassay, and can be measured by radioimmunoassay, radioimmunoprecipitation, immunoprecipitation, immunohistochemical staining, enzyme-linked immunosorbent assay (ELISA), capture-ELISA, inhibition or competition assay, sandwich assay, flow cytometry, immunofluorescent staining or immunoaffinity purification using the antibody against CD73, but is not limited thereto. Cancer can be diagnosed by analyzing final signal intensity resulting from the above-described immunoassay process. In other words, when the marker protein of the present disclosure is highly expressed in a biological sample, and thus the signal is stronger in the biological sample than in a normal biological sample (e.g., normal stomach tissue, blood, plasma or serum), the biological sample is diagnosed as cancer.

Still other aspects provide kits for diagnosing a cancer, the kits comprising the composition for diagnosing the cancer. The kits can include the antibody against CD73 according to the present disclosure, and can diagnose the cancer by analyzing signals resulting from a reaction between a sample and the antibody. In this regard, the signal can include an enzyme conjugated to the antibody, for example, alkaline phosphatase, β-galactosidase, horseradish peroxidase, luciferase, and cytochrome P450, but is not limited thereto. When alkaline phosphatase is used as the enzyme, color development reaction substrates such as bromochloroindolyl phosphate (BCIP), nitro blue tetrazolium (NBT), naphthol-AS-B1-phosphate, and enhanced chemifluorescence (ECF) can be used as a substrate. When horseradish peroxidase is used, substrates such as chloronaphthol, aminoethylcarbazole, diaminobenzidine, D-luciferin, lucigenin (bis-N-methylacridnium nitrate), resorufin benzyl ether, luminal, Amplex Red reagent (10-acetyl-3,7-dihydroxyphenoxazine), p-phenylenediamine-HCl and pyrocatechol (HYR), tetramethylbenzidine (TMB), 2,2'-azine-di[3-ethyl-benzthiazoline sulfonate](ABTS), o-phenylenediamine (OPD) and naphthol/pyronin, glucose oxidase, nitroblue tetrazolium (t-NBT) and m-phenazine methosulfate (PMS) can be used, but is not limited thereto.

In addition, the kits can include a label that generates a detectable signal. Examples of the label can include, but are not limited to, chemicals (e.g., biotin), enzymes (alkaline phosphatase, β-galctosidase, horseradish peroxidase and cytochrome P450), radioactive substances (e.g., C14, I125, P32, and S35), fluorescent substances (e.g., fluorescein), light-emitting substances, chemiluminescent substances, and fluorescence resonance energy transfer (FRET). The measurement of activity of the enzyme used for diagnosing a cancer or the measurement of the signal can be performed according to various methods known in the art. Through the measurement, CD73 expression can be analyzed qualitatively or quantitatively.

Reference will now be made in detail to embodiments, examples of which are illustrated in the accompanying drawings, wherein like reference numerals refer to like elements throughout. In this regard, the present embodiments can have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

EXAMPLES

Hereinafter, exemplary embodiments are provided for better understanding of the present disclosure. However, the following exemplary embodiments are provided only for understanding the present disclosure more easily, but the content of the present disclosure is limited to the following exemplary embodiments.

Preparation Example 1. Selection of Anti-CD73 Antibodies by Biopanning 1-1. Selection of Phage Antibody Specifically Binding to CD73

To select antibody clones specifically binding to human and mouse CD73 proteins, biopanning was performed using a HuDVFab-8L phage antibody library. First, a recombinant human CD73 protein (Sino Biological, China) and a recombinant mouse CD73 protein (Sino Biological) were reacted with Dynabeads M-280 Tosylactivated beads at 4° C. for 48 hours, respectively. Beads bound to each CD73 protein were treated with a blocking buffer [phosphate-buffered saline (PBS) containing 3% skim milk and 0.1% tween-20] containing HuDVFab-8L (HuDVFab-L1~L6, L8, L12) recombinant antibody (Fab displayed on a phage coat protein pIII) library and allowed to react at 4° C. for 16 hours. Thereafter, recombinant phages non-specifically binding to CD73 protein were removed using KingFisher mL instrument. Phages specifically binding to CD73 protein were eluted by treatment with 0.2 M glycine (pH 2.2) buffer, and then neutralized by treatment with 1 M tris-HCl (pH 9.0) buffer. TG1 cells (Amersham Pharmacia Biotech, Sweden) into which a light chain gene of the antibody library was introduced were treated with the neutralized phages, and infected at 37° C. for 1 hour. The phage-infected TG1 cells were spread on an LB/ACT solid medium (LB medium containing 50 μg/ml ampicillin, 10 μg/ml carbenicillin, and 10 μg/ml tetracycline), and incubated at 27° C. for 16 hours, and then non-infected TG1 cells were removed. 10 ml of liquid medium was added to the plate containing the cultured colonies, which were then suspended and diluted at a density of $4.8 \times 10^8$ cells/ml. Ex-phage was added to infect TG1 cells at 37° C. for 1 hour. Then, the infected TG1 cells were precipitated using a centrifuge, and the supernatant was discarded. TG1 cells were resuspended in 5 ml of 2×YT/ACTKA medium (2×YT medium containing 50 μg/ml ampicillin, 10 μg/ml carbenicillin, 10 μg/ml tetracycline, 50 μg/ml kanamycin, 0.001% arabinose), and incubated at 27° C. for 6 hours. Thereafter, the supernatant containing the phages was obtained using a centrifuge and reacted with Dynabeads M-280 Tosylactivated beads bound with CD73 protein at 4° C. for about 20 hours. Then, three cycles of the biopanning were performed to select phage antibodies specifically binding to CD73. As a result, CD73-binding polyclonal antibodies including L2, L4, L6, and L8 light chains were selected from the HuDVFab-8L phage antibody libraries.

1-2. Selection of Monoclonal Phage Antibody Specifically Binding to CD73

Among the polyclonal antibodies selected in 1-2, monoclonal antibodies specifically binding to CD73 and having different heavy chain CDR (HCDR) sequences were selected by performing phage enzyme-linked immunosorbent assay (phage ELISA). The recombinant human CD73 protein and the recombinant mouse CD73 protein were diluted with a coating buffer (0.1 M NaHCO₃, pH 9.6) at a concentration of 2 μg/ml, and then each 50 μL thereof was dispensed in a 96-well Maxisorp ELISA plate (Nunc, Denmark), and allowed to react at 4° C. for 16 hours to coat the plate with CD73 protein. Non-coated protein and buffer were completely removed, and 200 μL of a blocking buffer was dispensed to each well, and allowed to react at 37° C. for 1 hour. 1 hour later, the buffer was completely removed, and 200 μL of 0.1% tween-20-containing PBS (PBS-T) buffer was added to each well, and this washing procedure was repeated three times. The phage-containing supernatant was diluted 1/10 with the blocking buffer, and 50 μL thereof was dispensed to each well and allowed to react at 37° C. for 1 hr. Thereafter, washing was performed in the same manner as above, followed by treatment with goat anti-M13 horseradish peroxidase (HRP) antibody (GE Healthcare, Chicago, Illinois) at 37° C. for 1 hr. The plate was washed in the same manner as above, and then 50 μL of TMB (3,3',5,5' (BD Biosciences, Franklin Lakes, New Jersey) substrate was dispensed to each well of the plate. Thereafter, absorbance was measured at a wavelength of 450 nm using a Model 680 Microplate Reader (Bio-Rad Laboratories, Hercules, California) to select 14 kinds of CD73-specific monoclonal phage antibodies.

FIG. 1 is a graph showing CD73-binding abilities of anti-CD73 antibodies which were selected through biopanning. As shown in FIG. 1, all phage antibodies, except for L2-20, bound to human CD73. Further, L2-47, L4-66, L6-1, L6-30, and L6-37 phage antibodies bound to mouse CD73 with binding ability corresponding to 50% or more of the binding ability to human CD73. L8-34 phage antibody non-specifically bound to CD32b protein, not to CD73. Among 14 kinds of the antibodies having different HCDR sequences, 12 kinds of the anti-CD73 phage antibodies, except for L2-20 having weak binding ability to human CD73 and L8-34 showing non-specific binding, were used in subsequent experiments.

Figure 2A:
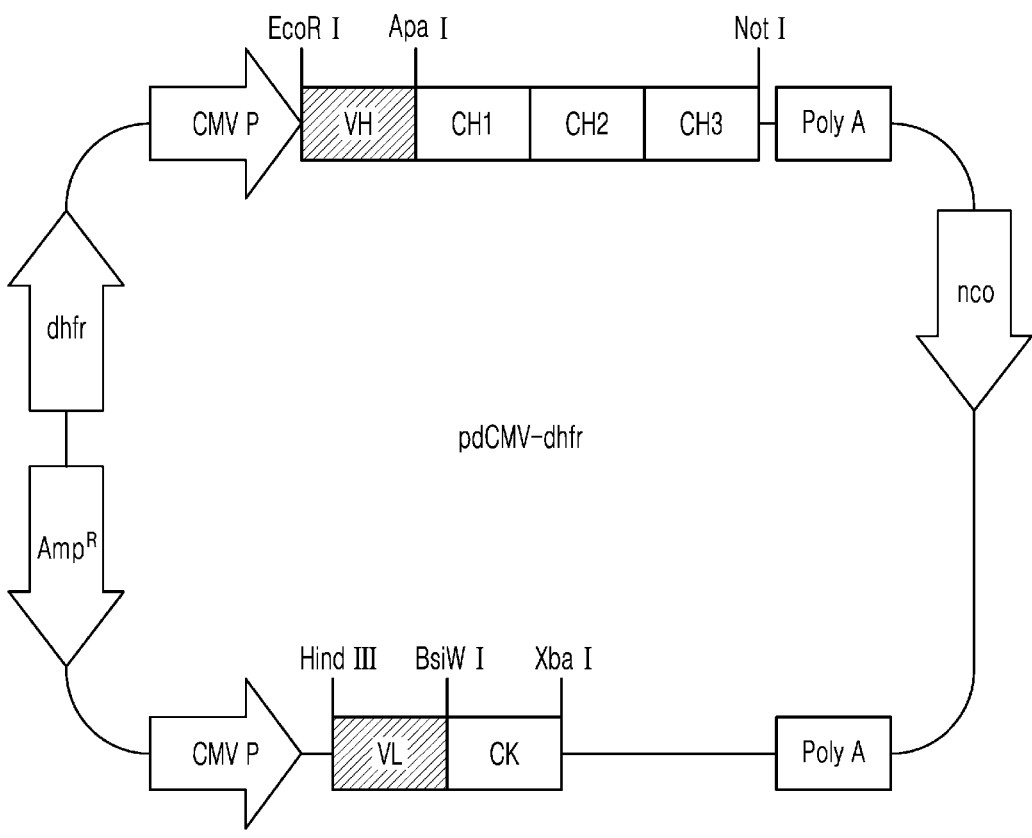
FIG. 2A shows a human IgG1 expression vector prepared by cloning $V_H$ and $V_L$ gene sequences of the anti-CD73 phage antibody into a pdCMV-dhfr vector including $C_H$ and $C_L$ gene sequences.

Preparation Example 2. Production and Selection of Human Anti-CD73 IgG1 Antibody 2-1. Preparation of Anti-CD73 Human IgG1 Isotype Expression Vector Twelve (12) kinds of the anti-CD73 phage antibodies selected in Preparation Example 1 were cloned to prepare human IgG1 antibodies. In detail, $V_L$ (light chain variable region) and $V_H$ (heavy chain variable region) gene sequences of the phage antibodies selected in Preparation Example 1 were cloned into a pdCMV-dhfr expression vector (provided by Professor Hyo Jeong Hong at Kangwon National University) including $C_L$ (light chain constant region) and CH1-CH2-CH3 (constant heavy chain, light chain constant region) gene sequences of human immunoglobulin G1 (IgG1) isotype, thereby preparing an intact IgG1 form (FIG. 2A). Polymerase chain reaction (PCR) was carried out using Pyrobest DNA polymerase (Takara, Japan) and a T100 Thermal Cycler. To clone each light chain sequence of the phage antibodies selected in Preparation Example 1, PCR was carried out using SEQ ID NO:47 and SEQ ID NO:48 of the following Table 1 under conditions of 94° C. for 30 sec, 58° C. for 30 sec, and 72° C. for 20 sec to amplify each light chain leader sequence. Each gene of $V_L$ sequences was amplified from $V_L$ genes of the phage antibodies selected in Preparation Example 1 by carrying out PCR using SEQ ID NO:49 and SEQ ID NO:50. The two kinds of the amplified PCR products were fused by assembly PCR under conditions of 94° C. for 30 sec, 58° C. for 30 sec, and 72° C. for 60 sec. Thereafter, the PCR product and the pdCMV-dhfr vector were treated with HindIII and BsiWI (Takara) restriction enzymes at 37° C. and 55° C., respectively, and reacted with each other. The leader sequence-$V_L$ gene fragment and the pdCMV-dhfr vector treated with the two kinds of restriction enzymes were ligated using T4 DNA Ligase and transformed into CaCl₂-treated competent cells by heat shock. Next, to clone the heavy chain sequences of the phage antibodies selected in Preparation Example 1, heavy chain leader sequences including EcoRI sequence were amplified by PCR using SEQ ID NO:51 and SEQ ID NO:52. Each gene of $V_H$ sequences including ApaI sequence was amplified by PCR using SEQ ID NO:53 and SEQ ID NO:54. The two kinds of the amplified PCR products were fused (leader sequence-$V_H$) by assembly PCR, and treated with EcoRI and ApaI restriction enzymes. The leader sequence-$V_H$ gene fragment treated with the restriction enzymes were cloned into the pdCMV-dhfr vector, into which light chain ($V_L$—$C_L$) gene and CH1-CH2-CH3 gene were inserted, in the same manner as above to prepare a human IgG1 expression vector.

Meanwhile, heavy chain and light chain genes (WO 2018/013611, WO 2016/075099) of CPI-006 (Corvus Pharmaceuticals, Burlingame, CA) and MEDI9447 (MedImmune, Gaithersburg, MD) used as positive controls were synthesized by Cosmogenetech co, Ltd., and cloned into the pdCMV-dhfr vector in the same manner as above using HindIII (Takara) and XbaI (Takara) as light chain restriction enzymes and EcoRI (Takara) and NotI (Takara) as heavy chain restriction enzymes.

TABLE 1

| Construct | SEQ ID NO: | Oligonucleotide sequence (5'-3') |
|---|---|---|
| Human IgG1 | 47 | gatcaacaagcttgccaccatggagacccacagccag |
| (Light chain) | 48 | cccctccacccgctcagccacag |
| | 49 | ctgagcggggtggaggggggacatccagatgacccagtctccatcttccctgtct |
| | 50 | ccaccgtacgtttgatttccagcttggtcccttggccgaaggt |
| Human IgG1 | 51 | gatcaacgaattcgccaccatggagtggtcctgggtc |
| (Heavy chain) | 52 | ggaaagcactccggtggtcacgctgag |
| | 53 | gcgtgaccaccggagtgctttcccaggtgcagctggtgcagtctgg |
| | 54 | cagtgggcccttggtggaggctgaggagacggtgaccagggtgccttg |

2-2. Production and Purification of Anti-CD73 Human IgG1 Isotype Antibody

To produce the selected 12 kinds of anti-CD73 human IgG1 antibodies, the pdCMV-dhfr vector cloned in 2-1 were transfected to ExpiCHO-S™ (Gibco) cells. In detail, ExpiCHO-S™ cells were incubated using an ExpiCHO-S™ expression medium (Gibco, ThermoFisher scientific) in a shaking incubator under conditions of 37° C., 140 rpm, humidity of 80%, and 5% $CO_2$. The vector into which the selected 12 kinds of antibody genes were inserted were transfected to ExpiCHO-S™ cells which were subcultured at least three times, using an ExpiFectamine CHO Transfecton kit and OptiPRO™ SFM (1×) (Gibco). Thereafter, the cells were incubated for 20 hours in a shaking incubator under the same conditions as above. The incubated cells were treated with ExpiFectamine™ CHO feed and an enhancer, and incubated for 7 days under the same conditions as above. The culture medium was recovered and centrifuged at 4,000 rpm and 4° C. for 15 minutes to obtain the supernatant containing the protein sample. The supernatant was filtered through a 0.2 μm filter paper to remove impurities. Thereafter, the antibody sample produced from CHO cells was purified by affinity chromatography. In detail, CaptureSelect IgG-CH1 Affinity Matrix resin was reacted with the culture medium, from which impurities had been removed, at 4° C. for 6 hours to bind the antibody sample in the culture medium to the resin. The reacted resin was washed with 10 column volumes (CVs) of TBS buffer (pH 7.4), and 100 mM citrate buffer (pH 3.0) was applied to elute the antibody sample, which was neutralized to be slightly acidic (pH 6.0 to pH 6.5) by adding 1 M Tris-HCl buffer (pH 9.0). The neutralized buffer was filtered through a 0.2 μm filter paper to remove impurities, and proteins were quantitatively analyzed at a UV wavelength of 280 nm.

2-3. Size Analysis of Anti-CD73 Human IgG1 Isotype Antibody Proteins

The sizes of the antibody proteins produced and purified in 2-2 were analyzed by SDS-PAGE. First, the antibody proteins were diluted with a 2-mercaptoethanol-containing Pierce™ LDS sample buffer and a non-reducing buffer (4×; Thermo Fisher Scientific), and then heated for 5 minutes. Thereafter, each 1 μg of the protein samples was loaded onto each well with a 4% to 15% Mini-PROTEAN® TGX™ Precast Protein Gel gradient (Bio-Rad), and electrophoresed using PowerPac™ Basic Power Supply at 140 V for 40 minutes. The electrophoresed gel was reacted with a Brilliant Blue R 250 protein staining solution (ELPISBIO, Korea) for 60 minutes, and then treated with a destaining buffer [30% methanol, 10% acetic acid] to observe protein bands.

Figure 2B:
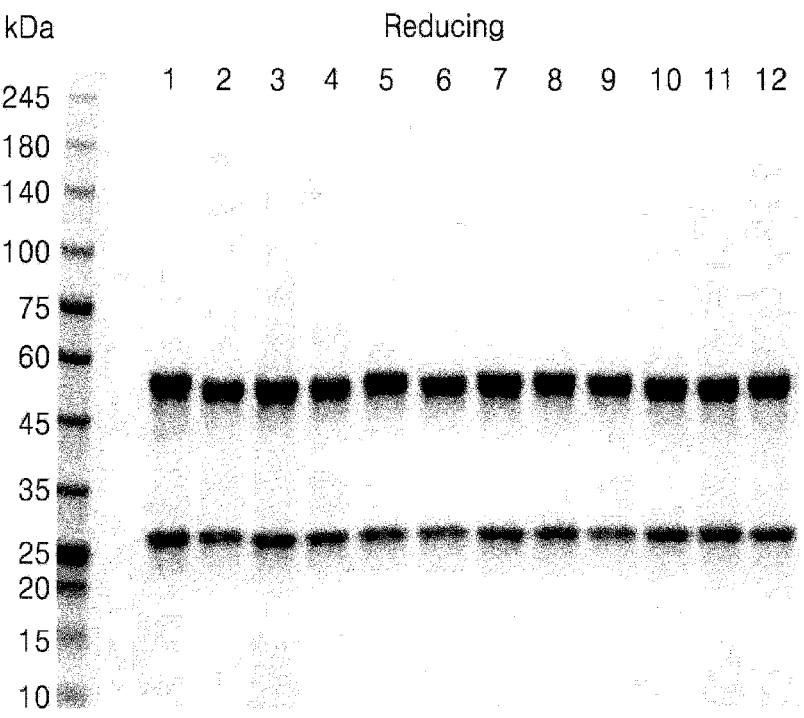
FIG. 2B shows SDS-PAGE results of human IgG1 antibodies, wherein Lane 1 to Lane 12 represent L2-3, L2-47, L4-1, L4-4, L4-5, L4-46, L4-66, L6-1, L6-7, L6-30, L6-37, and L8-24, respectively.

FIG. 2B shows SDS-PAGE results of human IgG1 antibodies. As shown in FIG. 2B, heavy chain and light chain of the purified 12 kinds of antibodies had a size of 50 kDa and 25 kDa, respectively and all of the protein bands were observed at positions corresponding to the theoretical sizes.

2-3. Examination of CD73-Binding Ability of Anti-CD73 Human IgG1 Isotype Antibody ELISA experiments were performed to compare CD73-binding ability between 12 kinds of the human anti-CD73 IgG1 antibodies produced and purified in 2-2. The recombinant human CD73 protein was diluted with a carbonate coating buffer at a concentration of 1 μg/ml, and then 100 μL thereof was dispensed to each well of a 96-well Maxisorp ELISA plate, and allowed to coat at 4° C. for 16 hours. Non-coated proteins and buffer were completely removed, and 300 μL of a PBS buffer (pH 7.4) containing 3% BSA and 0.1% tween-20 was dispensed to each well, and then allowed to react at room temperature for 2 hours for blocking. 2 hours later, the remaining buffer was removed, and 300 μL of PBS-T buffer was dispensed to each well, and washing was performed by repeating the removal process three times. The anti-CD73 IgG1 antibody was serially diluted using PBS buffer at a concentration of 100 nM, and added and reacted at 37° C. for 1 hour. After washing, donkey anti-human IgG Fc HRP antibody (Jackson ImmunoResearch, West Grove, Baltimore Pike) was added and reacted at 37° C. for 1 hour. The same washing procedure as the above method was performed, and 100 μL of TMB substrate was dispensed to each well, and allowed to react for 7 minutes. Absorbance at a wavelength of 450 nm was measured using a Model 680 Microplate Reader. Absorbance was also measured for a negative control (Rituximab) and a positive control (CPI-006, MEDI9447) samples in the same manner as above.

Figure 3A:
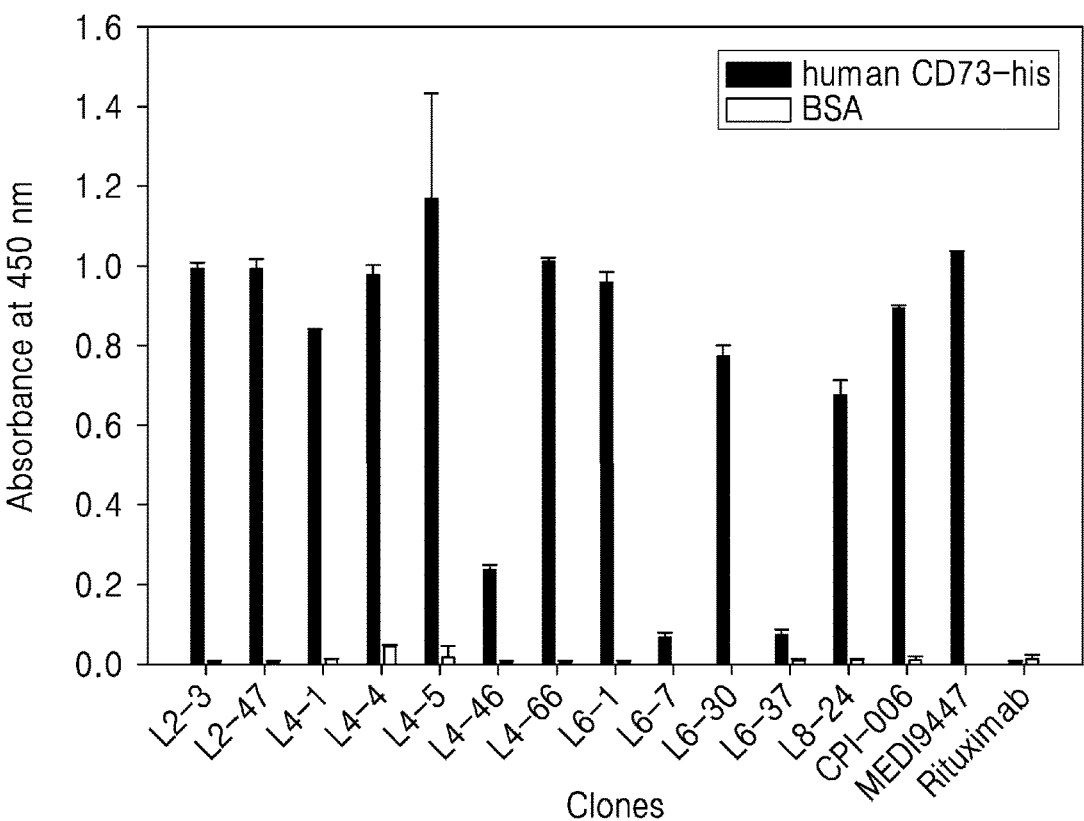
FIG. 3A shows results of performing ELISA to analyze CD73 binding of 12 kinds of purified human IgG1 isotype antibodies.

FIG. 3A shows a graph showing human CD73-binding ability of the purified 12 kinds of human anti-CD IgG1 antibodies. As shown in FIG. 3A, among the purified 12 kinds of antibodies, 9 kinds thereof and two positive controls remarkably strongly bound to human CD73, as compared with BSA, and the rest 3 kinds of antibodies (L4-46, L6-7, and L6-37) relatively weakly bound thereto. Further, the negative control (rituximab IgG1) antibody did not bind to human CD73.

2-4. Examination of Enzymatic Activity of Membrane CD73 Protein

To compare inhibitory activities of 12 kinds of the human anti-CD73 IgG1 antibodies produced and purified in 2-2 against membrane CD73 enzymatic activity, a malachite green assay was performed for MDA-MB-231 cells expressing membrane CD73 on the cell surface (Korean Cell Line Bank). MDA-MB-231 cells were dispensed at a density of $2.0×10^4$ cells/well in a 96-well plat plate, and incubated in an incubator under conditions of 37° C. and 5% $CO_2$ for 20 hours. After incubation, washing was performed using an assay buffer twice, and 12 kinds of the human anti-CD73 IgG1 antibody samples were diluted with the assay buffer at a concentration of 500 nM, added to each well, and allowed to react at 37° C. for 1 hour. Thereafter, 250 µM of AMP was added to each well, and reacted at 37° C. for 20 minutes. 40 µL of the supernatant excluding cells was dispensed to a new 96-well plate. To measure CD73 enzymatic activity, phosphate included in the supernatant was detected using a Malachite Green Phosphate Detection Kit, and absorbance at a wavelength of 620 nm was measured using an Epoch microplate spectrophotometer. Absorbance was also measured for the negative control (Rituximab) and positive control (CPI-006, MEDI9447) samples in the same manner as above.

Figure 3B:
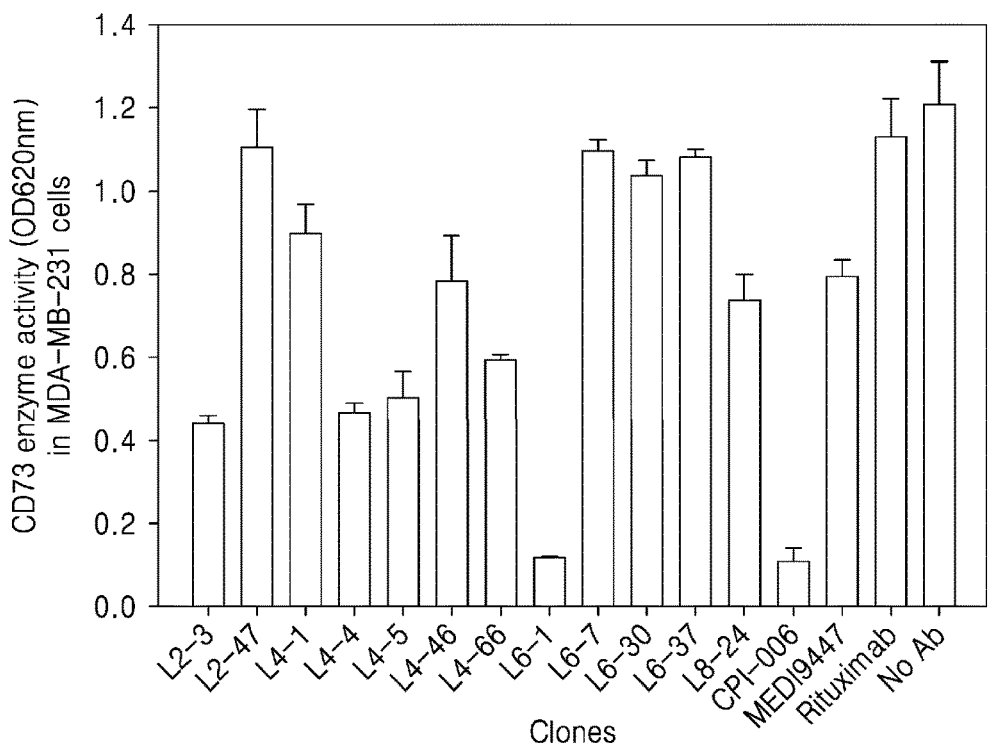
FIG. 3B shows results of performing an in vitro assay of MDA-MB-231 cells to compare 12 kinds of purified human IgG1 isotype antibodies according to inhibition of CD73 enzymatic activity, wherein the CD73 enzymatic activity was determined by measuring phosphate degraded by CD73 using a malachite green reagent.

FIG. 3B shows results of examining whether the purified 12 kinds of human anti-CD73 IgG1 isotype antibodies inhibited CD73 enzymatic activity. As shown in FIG. 3B, among 12 kinds of anti-CD73 human IgG1 antibodies, 5 kinds of antibodies (L2-3, L4-4, L4-5, L4-66, and L6-1) exhibited 50% or more of inhibition against CD73 enzymatic activity, as compared with the negative control, and of them, L6-1 antibody exhibited 90% or more of inhibition against CD73 enzymatic activity, indicating high inhibitory activity similar to that of CPI-006 (91%). The rest 4 kinds of antibodies (L2-3, L4-4, L4-5, and L4-66) exhibited 63%, 61%, 58%, and 50% of inhibition against CD73 enzymatic activity, respectively, indicating inhibitory activity similar to or higher than that of MEDI9447 (34%).

2-5. Examination of CD73 Cross-Binding Ability of Anti-CD73 Human IgG1 Isotype Antibody To compare cross-binding ability to human, monkey, rat, and mouse CD73 proteins (Sino Biological) between 5 kinds of human anti-CD73 IgG1 antibodies (L2-3, L4-4, L4-5, L4-66, L6-1) that exhibited inhibitory activity against CD73 enzymatic activity, similar to or higher than that of the positive control, as in 2-3, ELISA experiments were performed in the same manner as in 2-3.

Preparation Example 3. Preparation of APBA2-01 and APBA2-02 Antibodies 3-1. Preparation of APBA2-01 and APBA2-02 Monoclonal Antibodies A stable cell pool expressing APBA2-01 and APBA2-02 monoclonal IgG antibodies selected in Preparation Example 2-5 was produced. First, light chain and heavy chain genes of APBA2-01 and APBA2-02 monoclonal antibodies were cloned into pD2539 and pD2535nt (Horizon Discovery, United Kingdom) vectors, respectively. $V_L$ and $V_H$ of APBA2-01 and APBA2-02 antibodies and $C_L$ and $C_H$ genes of human IgG isotype were synthesized as codon sequences optimized for Chinese hamster ovary (CHO) cells. The synthesized light chain gene of APBA2-01 antibody was treated with Bbs1 (Thermo Fisher Scientific) and BsrG1 (Thermo Fisher Scientific) restriction enzymes, and ligated with the pD2539 vector treated with the same restriction enzymes. The synthesized V gene of APBA2-01 antibody was amplified by PCR using SEQ TD NO: 51 of Table 1 and SEQ ID NO: 55 of Table 2, and $C_H$ gene of human IgG was amplified by PCR using SEQ TD NO:56 and SEQ TD NO:57 of the following Table 2. The two amplified PCR products were fused with each other by assembly PCR. The fused heavy chain gene and pD2535nt vector were treated with Bbs1 restriction enzyme, and reacted. The synthesized $V_L$ gene of APBA2-02 antibody was amplified by PCR using SEQ ID NO:47 of Table 1 and SEQ ID NO:58 of Table 2, and $C_L$ gene of human IgG was amplified by PCR using SEQ TD NO:59 and SEQ TD NO:60 of the following Table 2. $V_H$ gene of APBA2-02 antibody was amplified by PCR using SEQ TD NO: 51 of Table 1 and SEQ ID NO: 61 of Table 2, and $C_H$ gene of human IgG was amplified by PCR using SEQ ID NO:57 and SEQ ID NO:62 of the following Table 2. The two amplified PCR products were fused by assembly PCR. Thereafter, cloning was performed in the same manner as above.

TABLE 2

| Construct | SEQ ID NO: | Oligonucleotide sequence(5'-3') |
| --- | --- | --- |
| APBA2-01 | 55 | gctagacacggtcaccagggtg |
| (hIgG1 heavy chain) | 56 | caccctggtgaccgtgtctagcgcatcaacaaaaggtccttcagttttcccc |
| | 57 | aggaagacgcttttagaggcggccgctcactttcctggtgaaag |
| APBA2-02 | 58 | ctaggagcggccacggtccgcttgatctccagcttggtgccctg |
| (hIgG1 light chain) | 59 | cggaccgtggccgctcctag |
| | 60 | ccactctagagaagacgcttttagatcaacactc |
| APBA2-02 | 61 | ggagctcacggtcaccagggtgccctg |
| (hIgG1 heavy chain) | 62 | gtgaccgtgagctccgcatcaacaaaaggtccttcagttttcccc |
| APBA2-01 | 63 | caccctggtgaccgtgtctagcgctaagactaccccaccatcagtctatccc |
| (mIgG1 heavy chain) | 64 | atcggcggccgcgaagacgcttttagatca |
| APBA2-01 | 65 | caccctggtgaccgtgtctagcgctaaaactaccgcacctagcgtgtatcct |
| (mIgG2a heavy chain) | | |

Figure 3C:
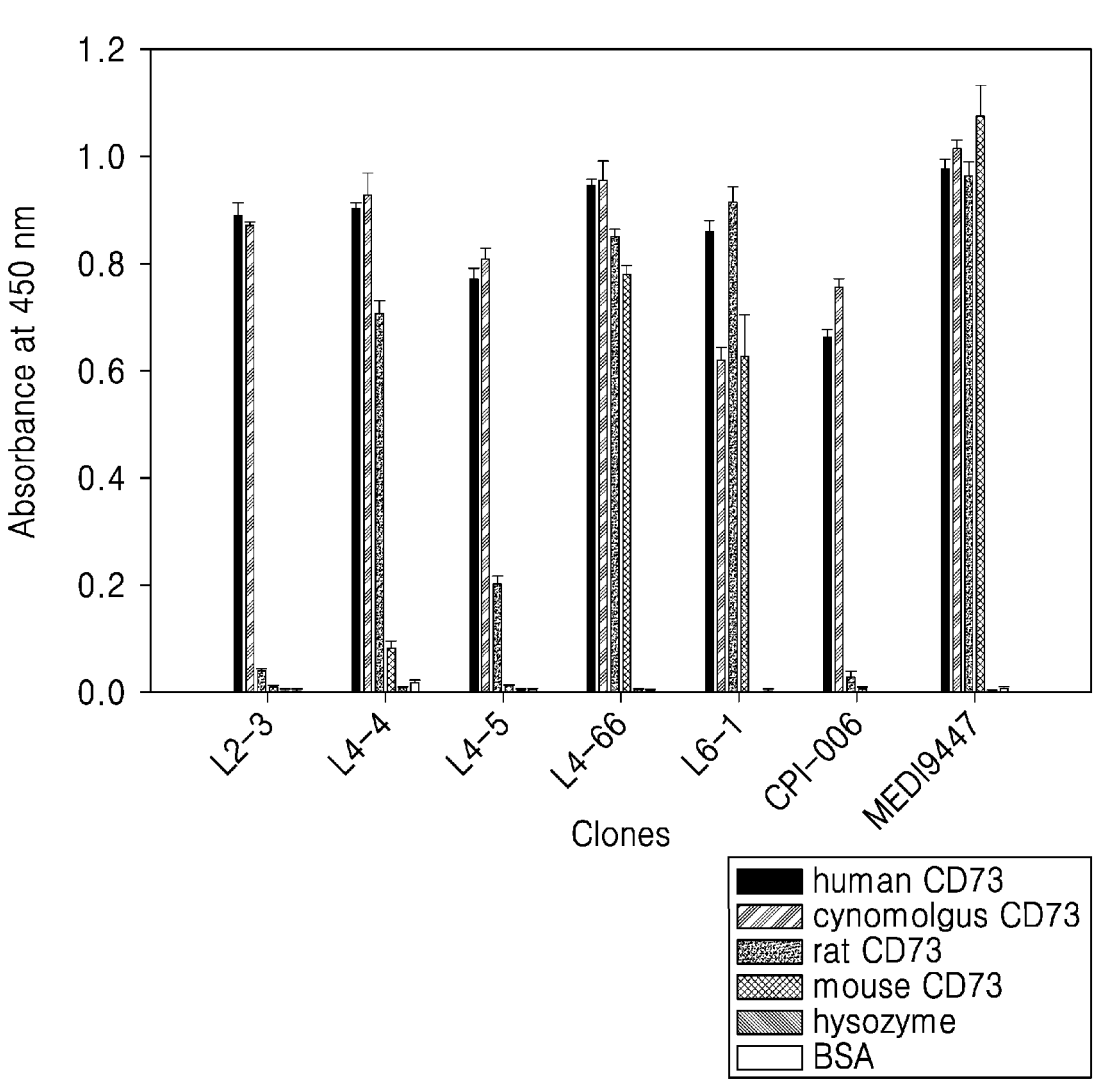
FIG. 3C shows ELISA results of analyzing cross-binding ability to human, monkey, rat, and mouse CD73, wherein CD73 binding of antibodies was examined by measuring absorbance at a wavelength of 450 nm.
Figure 4A:
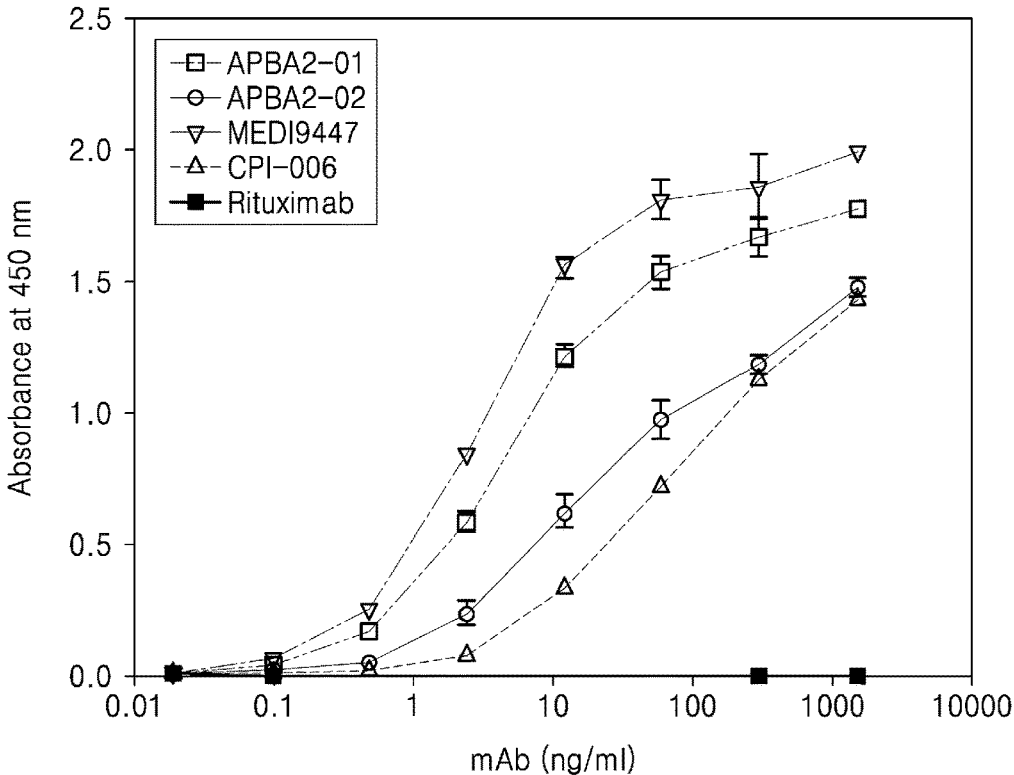
Figure 4B:
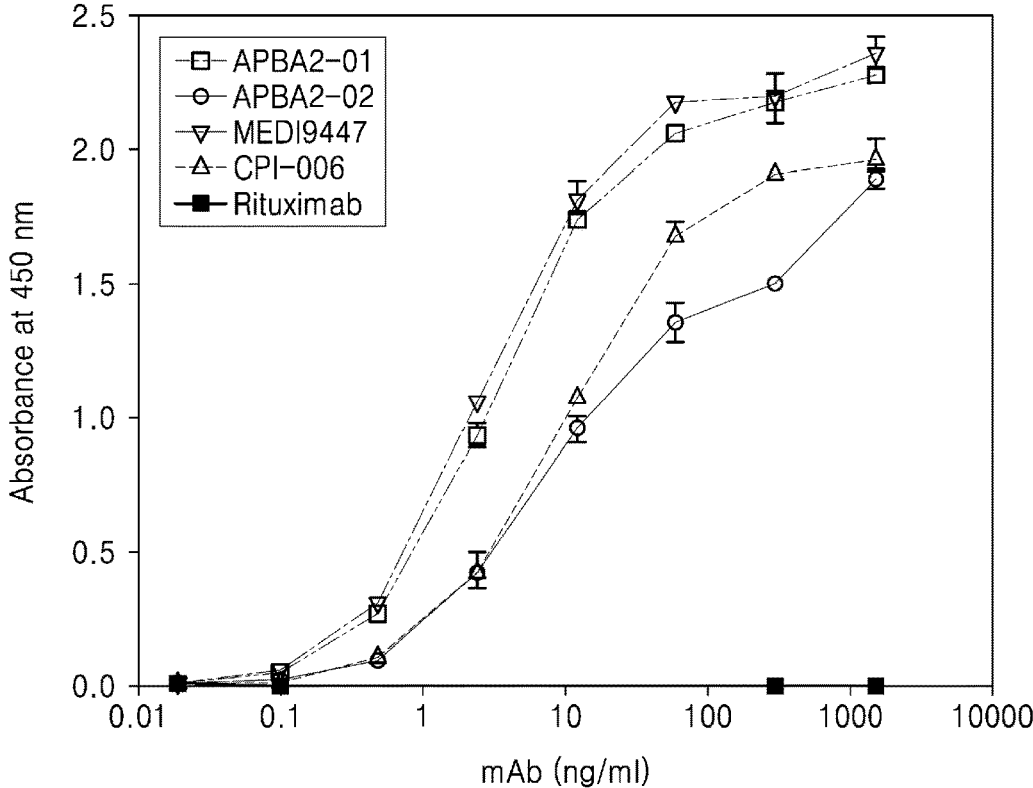
Figure 4C:
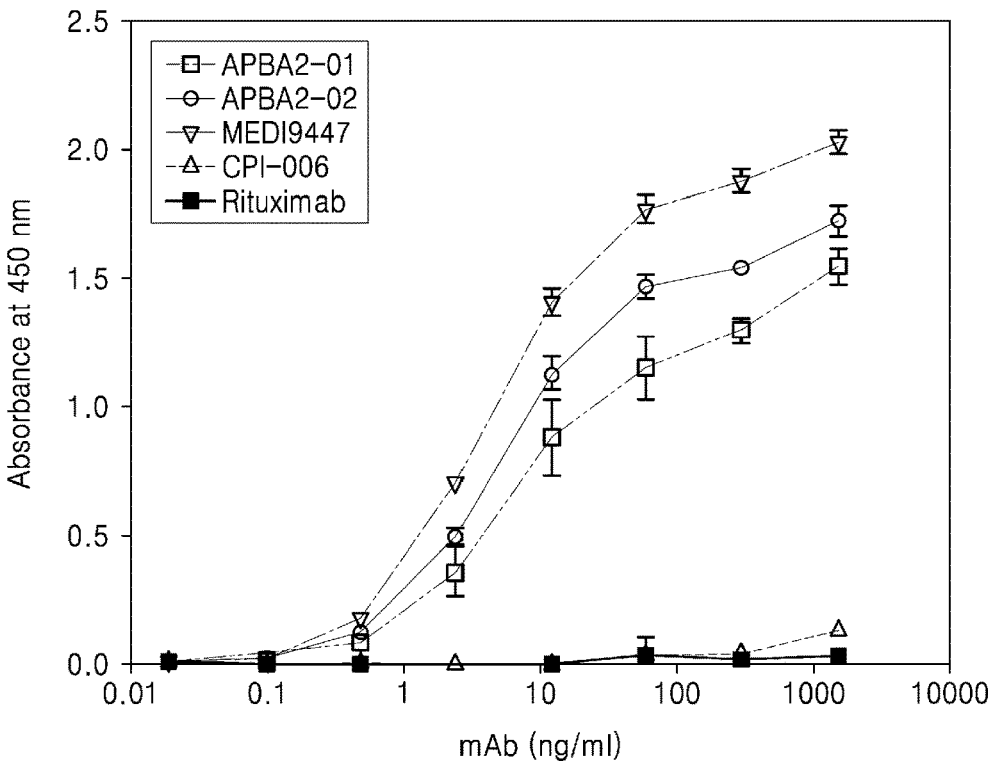
Figure 4D:
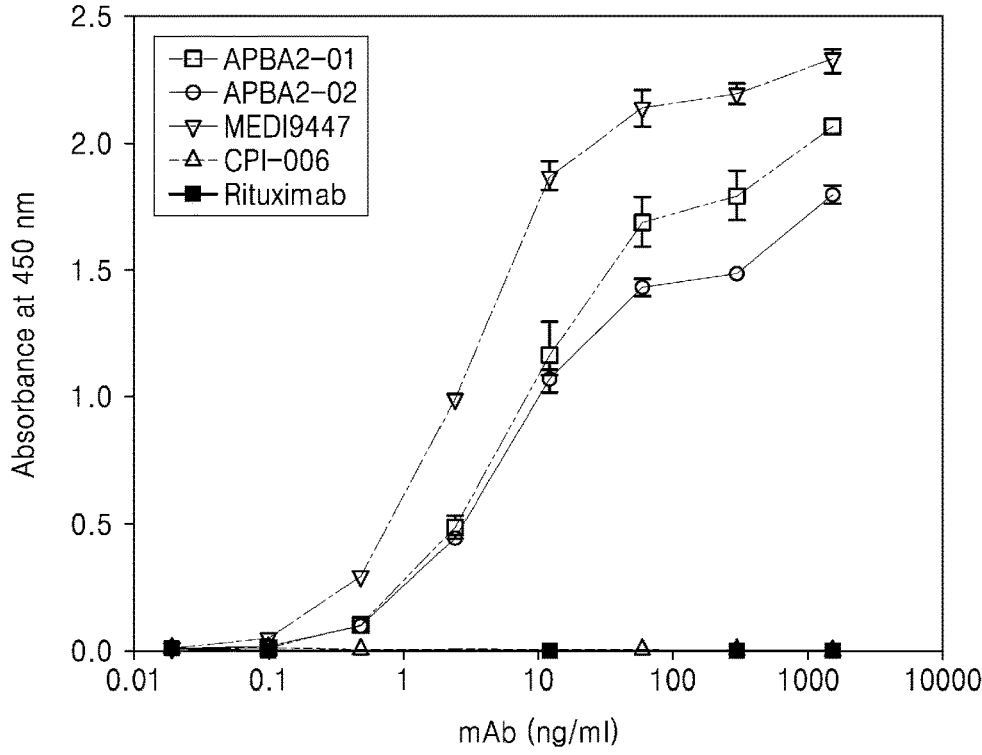

FIG. 3C shows results of analyzing cross-binding ability to human, monkey, rat, and mouse CD73. In FIG. 3C, all of L4-66 and L6-1 antibodies and MEDI9447 antibody were reacted to human, monkey, rat, and mouse CD73, but L2-3 and L4-5 antibodies and CPI-006 antibody were reacted only to human and monkey CD73, and L4-4 antibody was reacted only to human, monkey, and rat CD73. Thus, they showed different binding patterns from each other. Based on these results, two kinds of antibodies (L4-66 and L6-1) showing cross-binding to human and mouse CD73, similar to MEDI9447 antibody, were selected, and designated as APBA2-01 and APBA2-02, respectively.

3-2. Preparation of APBA2-01 and APBA2-02 Chimeric Antibodies

APBA2-01 and APBA2-02 antibodies were prepared as human-mouse IgG1 and IgG2a chimeric antibody sequences having human $V_L$ and $V_H$ gene sequences and $C_L$ sequence and $C_H$ sequence of mouse antibody sequence, respectively. The synthesized human $V_L$-mouse $C_L$ chimeric antibody gene fragments of APBA2-01 and APBA2-02 were cloned into a pD2539 vector in the same manner as in 3-1, respectively. The synthesized $C_H$ genes of mouse IgG1 and IgG2a were amplified by PCR using SEQ ID NO:63, SEQ ID NO:64 and SEQ ID NO:64, SEQ ID NO:65, respectively. Thereafter, the product was fused with $V_H$ gene of APBA2-01 antibody by assembly PCR in the same manner as in 3-1.

$V_H$-mouse IgG1 and mouse IgG2a gene fragments of the fused APBA2-01 antibody gene and the synthesized APBA2-02 antibody were cloned into a pD2535nt vector in the same manner as above.

3-3. Preparation of Stable Pools of APBA2-01 and APBA2-02 Antibody Protein

Stable pools to produce the antibody proteins of Preparation Examples 3-1 and 3-2 were prepared. First, GS null CHO K1 (Horizon Discovery) cells were dispensed in a medium prepared by adding 4 mM L-glutamine (Gibco) to CD fortiCHO (Thermo Fisher Scientific), and incubated in a shaking incubator under conditions of 37° C., 125 rpm, 80% humidity, and 5% $CO_2$. Vectors, into which light chain and heavy chain genes of APBA2-01 and APBA2-02 were inserted, respectively, were co-transfected into the cultured cells at a ratio of 1:3 [pD2539(light chain): pD2535nt(heavy chain)] using a Freestyle™ MAX Reagent (Invitrogen), and a total of 37.6 μg of the plasmid vector was used, followed by incubation for 48 hours under the same conditions as above. Thereafter, the cultured cells were transferred to a 50-ml conical tube (Nunc), and centrifuged, and then the cell pellet was resuspended in a CD fortiCHO medium without L-glutamine, and treated with 50 M methionine sulfoximine (MSX, Sigma-Aldrich, St. Louis, Missouri) to perform primary selection for 48 hours. Thereafter, the cells were treated with 10 μg/ml puromycin (Gibco) to perform secondary selection for 48 hours. Thereafter, the precipitated cells were suspended in a medium without L-glutamine at a density of $0.5 \times 10^6$ cells/ml, and then subjected to an additional selection process by treatment with MSX and puromycin for 3 weeks. In this regard, the medium was periodically replaced so that the cell density was maintained at $2.0 \times 10^6$ cells/ml or less, and the cells were cultured until the cell viability became 90% or more to prepare a stable pool cell stock. Cell density and viability were measured using a COUNTESSII automated cell counter.

3-4. Production and Purification of APBA2-01 and APBA2-02 Chimeric Antibody Proteins APBA2-01 and APBA2-02 human-mouse chimeric antibody proteins were produced from the stable pools prepared in 3-3. First, cells were suspended in a CD fortiCHO medium at a density of $0.2 \times 10^6$ cells/ml, and incubated in a shaking incubator under conditions of 37° C., 125 rpm, 80% humidity, and 5% $CO_2$. After incubation, when the cell density reached $2.0 \times 10^6$ cells/ml, cells were transferred to a shaking incubator under conditions of 32° C., 125 rpm, 80% humidity, and 5% $CO_2$, and antibody samples were produced for 7 days. Thereafter, the supernatant containing the antibody sample was obtained by centrifugation, and filtered through a 0.2 μm filter paper to remove impurities. Then, the antibody sample produced from the CHO cells were purified through three steps of chromatography (affinity chromatography, cation exchange purification, and anion exchange purification). First, affinity chromatography was performed using a MabSelect SuRe LX resin. The resin was washed with 10 CVs of tris-buffered saline (TBS) buffer, and the supernatant containing the antibody sample was applied to the resin at a flow rate of 20 ml/min. 5 CVs of TBS buffer and 5 CVs of 3% D-mannitol-containing TBS buffer were applied at a flow rate of 25 ml/min to remove substances non-specifically bound to the resin. 50 mM citrate (pH 3.5) and 3% D-mannitol buffer were applied at a flow rate of 20 ml/min to elute the antibody sample specifically bound to the resin from the resin. Then, the buffer containing the eluted protein sample was neutralized by treatment with 1 M tris-HCl buffer at pH 8.0, and filtered through a 0.2 μm filter paper to remove impurities. Next, cation exchange purification was performed using Capto adhere ImpRes multi-modal chromatography resin equilibrated with 50 mM tris, 200 mM citrate buffer at pH 7.0. The antibody sample obtained from the affinity chromatography was diluted ¼ with distilled water. Thereafter, the antibody sample was bound to the resin at a flow rate of 5 ml/min, and washed with 5 CVs of 50 mM tris, 200 mM citrate, and 1 M NaCl buffer at pH 7.0. Then, washing was performed using 5 CVs of 50 mM tris and 200 mM citrate at pH 7.0 at a flow rate of 25 ml/min to remove substances non-specifically bound to the resin. Then, 50 mM tris and 200 mM citrate buffer at pH 3.0 was serially applied at 20%-30%-40%-50%-70%-100% to elute the antibody sample specifically bound to the resin. Eluates were collected at each step and filtered through a 0.2 μm filter paper to remove impurities. Lastly, anion exchange purification was performed using a POROS™ 50 HQ Strong Anion Exchange resin. First, 2 M NaCl buffer was applied to the resin at a flow rate of 3 ml/min to wash the resin, and equilibrated by applying 5 CVs of 20 mM sodium phosphate buffer at pH 6.5. To bind the antibody samples obtained by the cation exchange purification to the resin, the sample was subjected to dialysis using 20 mM sodium phosphate buffer at pH 6.0 buffer to adjust pH and the salt concentration. The dialyzed sample was applied to the resin at a flow rate of 5 ml/min, and the buffer containing the collected proteins was filtered through a 0.2 μm filter paper to remove impurities. The proteins were quantified and analyzed.

Example 1. Comparison of CD73 Protein-Binding Ability 1-1. Water-Soluble CD73 Protein-Binding Ability The water-soluble CD73 protein-binding abilities of APBA2-01 and APBA2-02 antibodies produced and purified in Preparation Example 3 were examined by ELISA experiments. The experiments were performed in the same manner as in 2-3, except that the antibodies were added after serial dilution of 1,500 ng/ml to 0.019 ng/ml. The same procedures were also performed for positive controls (MEDI9447 and CPI-006) and a negative control (Rituximab).

FIGS. 4A to 4D shows graphs showing human, monkey, rat, and mouse CD73-binding abilities, respectively, of APBA2-01 and APBA2-02 antibodies. As shown, the binding ability to human CD73 protein (FIG. 4A) was high in this order of MEDI9447>APBA2-01>APBA2-02>CPI-006, and the binding ability to monkey CD73 protein (FIG. 4B) was high in this order of MEDI9447=APBA2-01>CPI-006>APBA2-02. Further, the binding ability to rat CD73 protein (FIG. 4C) was high in this order of MEDI9447>APBA2-02>APBA2-01, and the binding ability to mouse CD73 protein (FIG. 4D) was high in this order of MEDI9447>APBA2-01>APBA2-02. In other words, APBA2-01 showed the second highest binding ability to CD73 proteins (human, monkey, and mouse) after MEDI9447, and APBA2-02 showed relatively low binding ability to CD73, as compared with MEDI9447 and APBA2-01, but showed similar binding ability to that of CPI-006.

1-2. Membrane CD73 Protein-Binding Ability

Whether APBA2-01 and APBA2-02 antibodies produced and purified in Preparation Example 3 had binding ability to membrane CD73 protein was examined by flow cytometry. First, a human CD73-overexpressing breast cancer cell line MDA-MB-231 (Korean Cell Line Bank) and a mouse CD73-overexpressing breast cancer cell line 4T1(ATCC) were dispensed in an RPMI-1640 medium (Thermo Fisher Scientific) supplemented with 10% fetal bovine serum (FBS) (Gibco) and 1% penicillin-streptomycin (Gibco), respectively, followed by incubation in a humidified incubator under conditions of 37° C. and 5% $CO_2$. The number and viability of the cells were measured using a Vi-cell automated cell analyzer. MDA-MB-231 cells and 4T1 cells were dispensed at a density of $2.0 \times 10^5$ cells in a sterile microtube, respectively, and washed with MACS buffer (PBS containing 0.5% BSA and 2 mM EDTA) twice. Thereafter, APBA2-01 and APBA2-02 antibodies were diluted with MACS buffer at a concentration of 40 nM, and MDA-MB-231 and 4T1 cells were treated therewith, respectively and allowed to react at 4° C. for 1 hour. 1 hour later, the cells were washed with MACS buffer three times, and goat anti-human IgG Fc FITC antibody (Invitrogen) was added thereto, and allowed to react at 4° C. for 30 minutes. MDA-MB-231 and 4T1 cells were washed in the same manner as above, and fixed by treatment with 1% formaldehyde, and then flow cytometry was performed using BD FACSVERSE equipment. Positive controls (CPI-006 and MEDI9447) and a negative control (Rituximab) were also analyzed in the same manner as above.

Figure 5A:
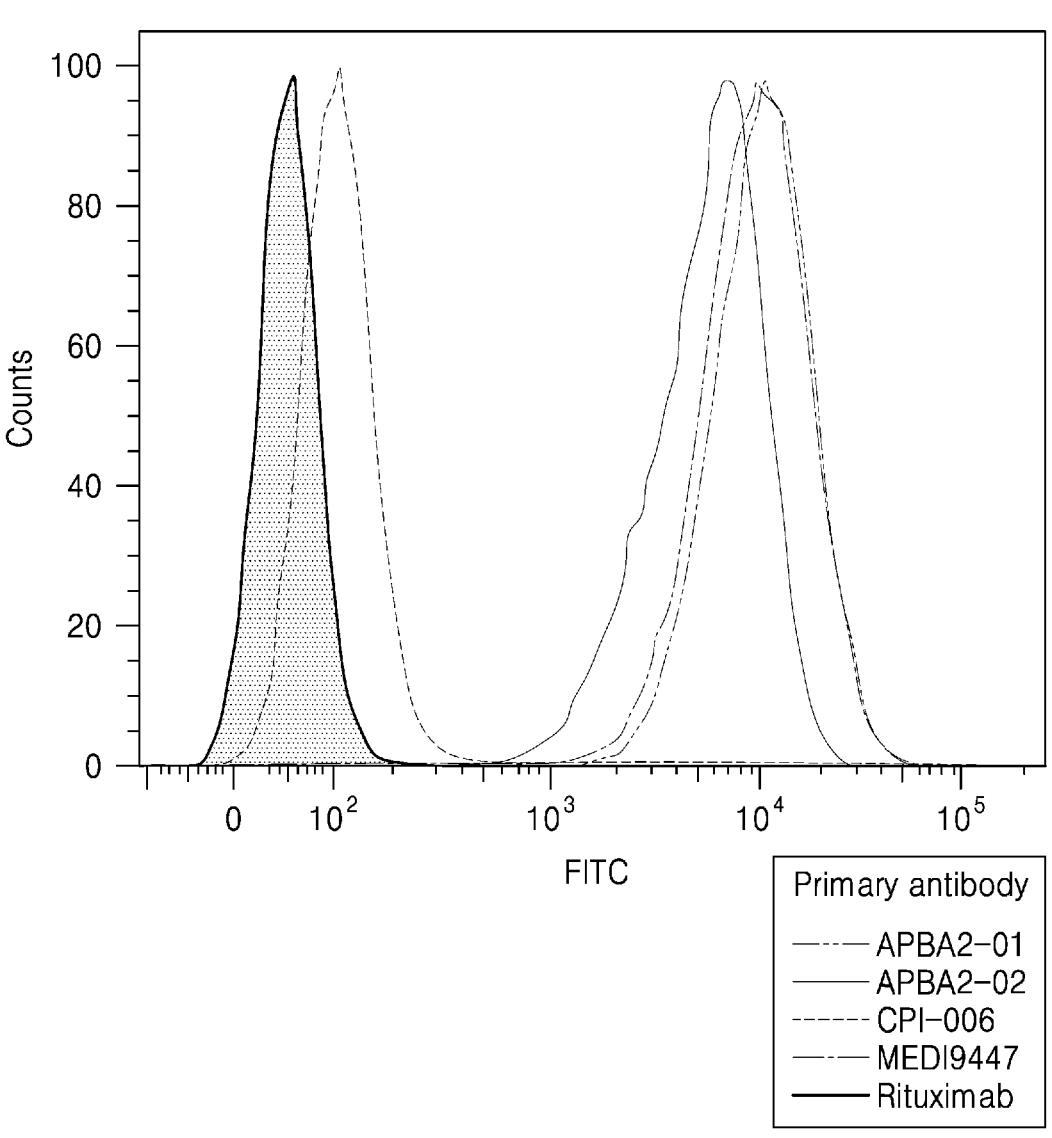
FIG. 5A is a graph of flow cytometry showing a comparison of membrane CD73-binding abilities of APBA2-01 and APBA2-02 antibodies in human CD73-expressing MDA-MB-231 cells.
Figure 5B:
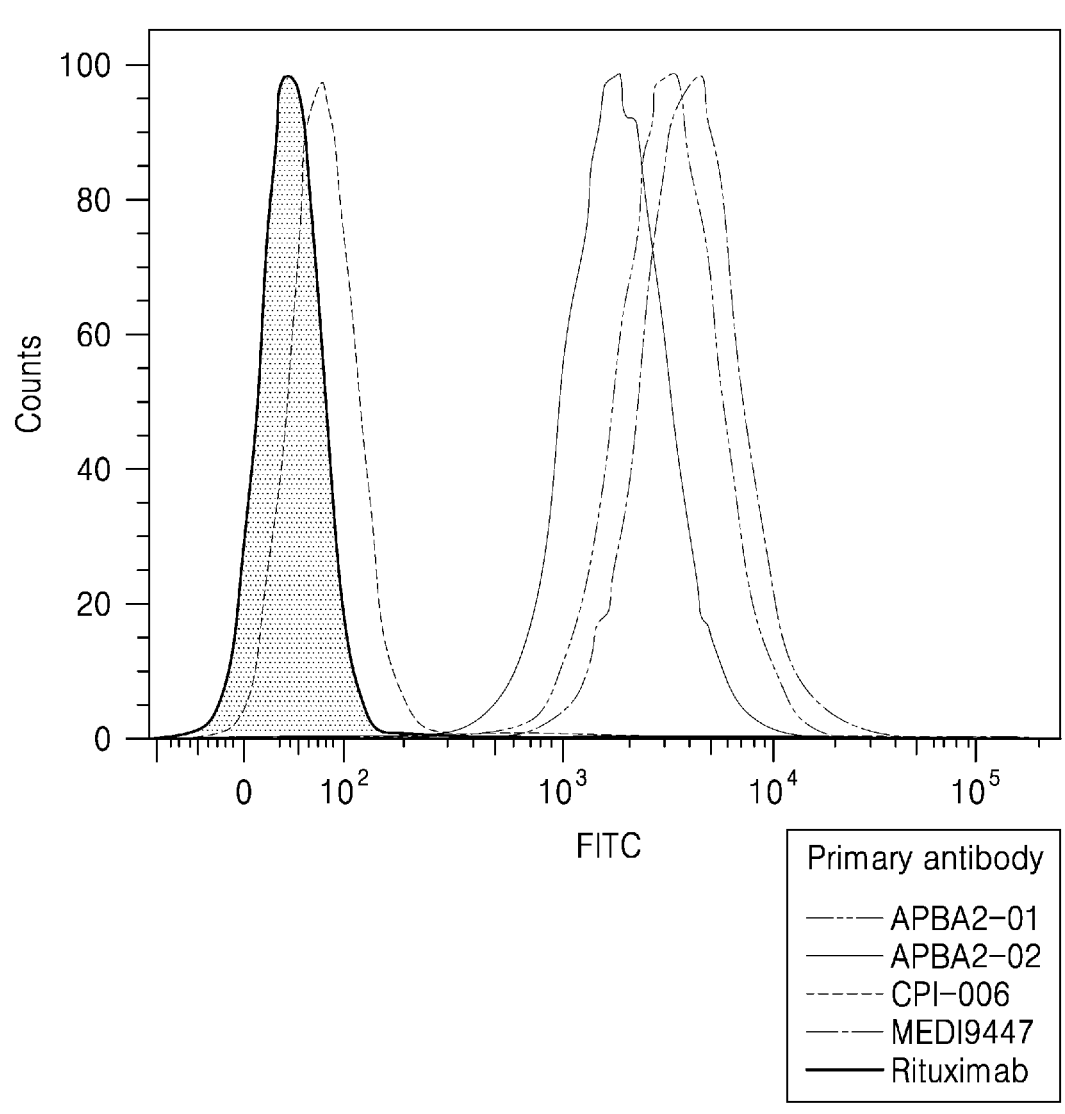
FIG. 5B is a graph of flow cytometry showing a comparison of membrane CD73-binding abilities of APBA2-01 and APBA2-02 antibodies in mouse CD73-expressing 4T1 cells.

FIG. 5A shows a graph showing a comparison of membrane CD73 protein-binding abilities of APBA2-01 and APBA2-02 antibodies in MDA-MB-231 cells, and FIG. 5B shows a graph showing a comparison of their binding abilities in 4T1 cells. As shown in FIGS. 5A and 5B, the antigen binding ability was high in this order of MEDI9447>APBA2-01>APBA2-02>CPI-006 in MDA-MB-231 and 4T1 cells. Further, MEDI9447, and APBA2-01, and APBA2-02 antibodies showed strong binding ability, as compared with the negative control (rituximab). However, the positive control CPI-006 antibody showed weak binding ability, as compared with MEDI9447, and APBA2-01 and APBA2-02 antibodies.

Example 2. Comparative Analysis of Epitopes

CD73 epitopes of APBA2-01 and APBA2-02 antibodies produced and purified in Preparation Example 3 and positive controls (CPI-006 and MEDI9447) were analyzed and compared by Bio-layer interferometry (BLI). First, an anti-human IgG Fc Capture (AHC) chip was hydrated in a sterile distilled water for 15 minutes, and subjected to conditioning by repeatedly reacting with a 0.1% BSA-supplemented PBS buffer at pH 7.4 (0.1% PBA) and a 10 mM glycine buffer at pH 1.7 for 20 seconds three times, respectively. Next, CPI-006 and MEDI9447 antibodies as the positive controls were diluted with 0.1% PBA buffer at a concentration of 200 nM, and loaded on the AHC chip for 600 seconds, respectively. The recombinant human CD73 protein sample diluted with 0.1% PBA buffer at a concentration of 20 nM was reacted and bound thereto for 900 seconds. Lastly, APBA2-01 and APBA2-02 samples were diluted with 0.1% PBA buffer at a concentration of 20 nM, and reacted with CPI-006, to which the recombinant human CD73 protein bound, for 900 seconds. All experimental procedures were performed at 30° C. under shaking of 1,000 rpm, and experimental results were analyzed using a ForteBio Data analysis 8 software.

Figure 6A:
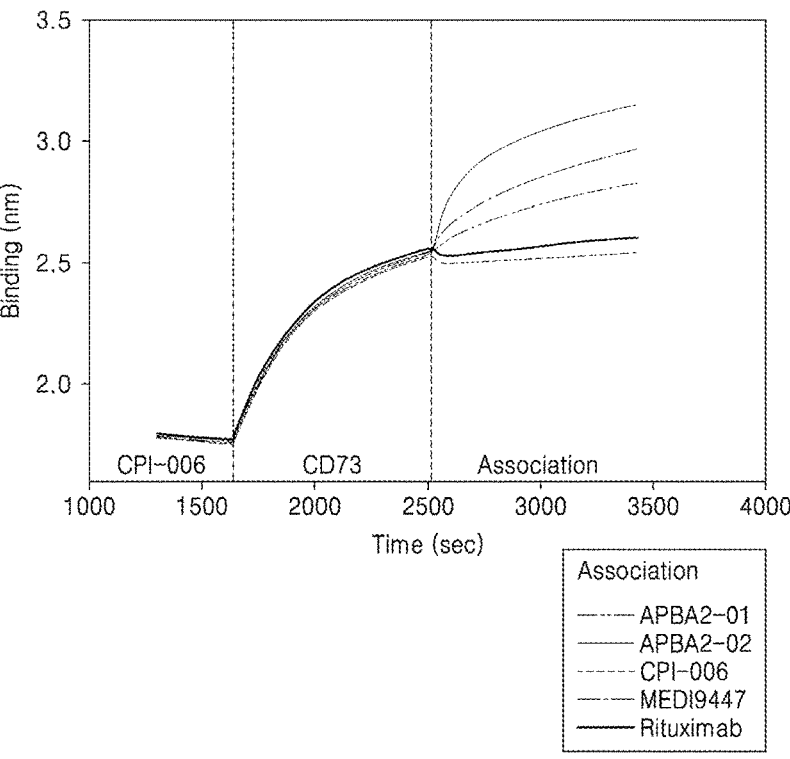
FIG. 6A is a graph showing results of bio-layer interferometry for analyzing competitive binding of APBA2-01 and APBA2-02 antibodies to the epitope of CPI-006.
Figure 6B:
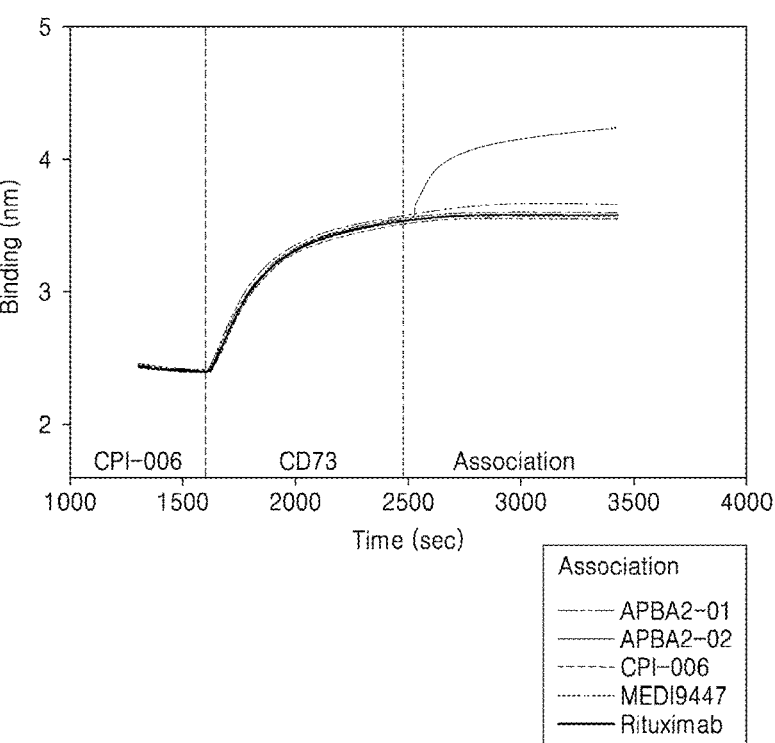
FIG. 6B is a graph showing results of bio-layer interferometry for analyzing competitive binding of APBA2-01 and APBA2-02 antibodies to the epitope of MEDI-9447.

FIG. 6A shows results of analyzing competitive binding of APBA2-01 and APBA2-02 antibodies to the epitope of CPI-006, and FIG. 6B shows results of analyzing competitive binding thereof to the epitope of MEDI-9447. As shown in FIG. 6A, antibodies sharing the epitope with CPI-006 were not observed. Meanwhile, as shown in FIG. 6B, the positive controls (MEDI9447 and CPI-006) and APBA2-01 antibody did not bind to human CD73 protein, but bound to APBA2-02 antibody.

The results imply that APBA2-01 antibody has the possibility of competitively binding to the epitope similar to that of MEDI9447 antibody, since APBA2-01 antibody was unable to bind to human CD73 protein to which MEDI9447 antibody bound. Meanwhile, CPI-006 antibody was unable to bind to human CD73 protein to which MEDI9447 antibody bound, unlike the results of FIG. 6A. In other words, CPI-006 binds to an epitope at the C-terminus of CD73 to which AMP binds, and thus competes with AMP to inhibit CD73 enzymatic activity. In contrast, MEDI9447 binds to the N-terminal domain of CD73 which is a homodimer, and thus prevents transition of CD73 to the active structure to inhibit CD73 enzymatic activity. Therefore, APBA2-01 antibody showing similar activity inhibition pattern to MEDI9447 is expected to prevent transition of CD73 to the active structure, and APBA2-02 antibody showing similar activity inhibition pattern to CPI-006 is expected to competitively inhibit binding of AMP to CD73.

Example 3. Evaluation of In Vitro CD73 Enzymatic Activity-Inhibiting Ability 3-1. Evaluation of Water-Soluble CD73 Activity-Inhibiting Ability To examine whether APBA2-01 and APBA2-02 antibodies produced and purified in Preparation Example 3 inhibit the enzymatic activity of water-soluble CD73 protein, a malachite green assay capable of quantifying phosphate was performed. First, recombinant human CD73 protein was diluted with an assay buffer (25 mM tris, 5 mM $MgCl_2$, pH 7.5) at a concentration of 2 nM, and then APBA2-01 and APBA2-02 antibody samples were serially diluted with the assay buffer from 50 nM to 0.7813 nM, respectively. The diluted CD73 protein and each of the antibody samples were reacted at 37° C. for 1 hour. Thereafter, AMP was added at a final concentration of 400 μM, and reacted at 37° C. for 20 minutes. Thereafter, reaction was allowed for 20 minutes using a Malachite Green Phosphate Detection Kit, and absorbance at 620 nm was measured using an Epoch microplate spectrophotometer. Positive controls (CPI-006 and MEDI9447) and a negative control (human IgG1 isotype) (BIO X Cell, West Lebanon, New Hampshire) were also measured for absorbance in the same manner as above.

Figure 7:
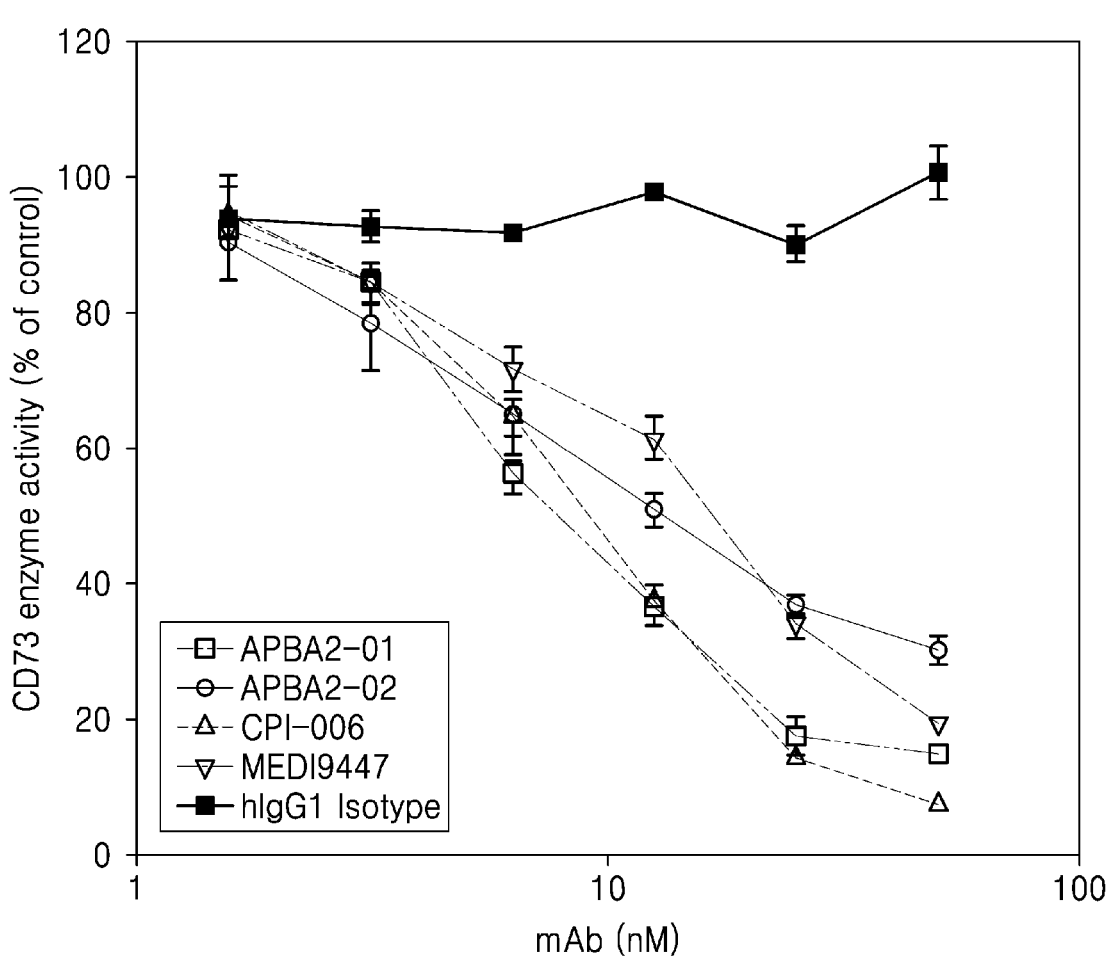
FIG. 7 is a graph showing results of a malachite green assay for comparing inhibition of water-soluble CD73 enzymatic activity by APBA2-01 and APBA2-02 antibodies.

FIG. 7 shows the results of the malachite green assay for evaluating inhibition of water-soluble CD73 enzymatic activity by APBA2-01 and APBA2-02 antibodies. As shown in FIG. 7, water-soluble CD73 enzymatic activity-inhibiting abilities of anti-CD73 antibodies were high in this order of CPI-006>APBA2-01>APBA2-02>MEDI9447.

3-2. Evaluation of Membrane CD73 Activity-Inhibiting Ability

To examine whether APBA2-01 and APBA2-02 antibodies produced in Preparation Example 3 inhibit the enzymatic activity of membrane CD73 protein, phosphate quantification (malachite green assay) and luciferin oxidation measurement (CellTiter-Glo® assay) were performed, respectively.

CD73 enzymatic activity was analyzed by the malachite green assay. First, to measure CD73 enzymatic activity, the assay was performed in the same manner as in Preparation Example 2-4, except that MDA-MB-231 cells and 4T1 cells were dispensed at a density of $2 \times 10^4$ cell/wells and $1.0 \times 10^4$ cell/wells, respectively and APBA2-01 and APBA2-02 antibodies were used after serially dilution from 400 nM to 0.0244 nM. Absorbance was also measured for negative control (Rituximab) and positive control (CPI-006 and MEDI9447) samples in the same manner as above.

Next, CD73 enzymatic activity was analyzed by a Cell-Titer-Glo® assay. First, MDA-MB-231 cells and 4T1 cells were dispensed at a density of $2.0 \times 10^4$ cells/well and $1.0 \times 10^4$ cells/well in a 96-well flat plate (SPL), and incubated in an incubator under conditions of 37° C. and 5% $CO_2$ for 20 hours. After incubation, the supernatant was removed, and cells were washed with an RPMI-1640 medium without FBS. Thereafter, APBA2-01 and APBA2-02 antibody samples were serially diluted with a medium from 500 nM to 0.0305 nM, and each well was treated therewith and allowed to react at 37° C. for 30 minutes. After reaction, AMP was added at a concentration of 400 μM, and allowed to react at 37° C. for 3 hours. Then, the supernatant was reacted with 200 μM of ATP in a new 96-well white plate, and treated with CellTiter-Glo®, and luminescence was measured using Synergy M1 reader equipment according to a standard method provided by the manufacturer. Lumines-cence was also measured for negative control (Rituximab) and positive control (CPI-006 and MEDI9447) samples in the same manner as above.

Figure 8A:
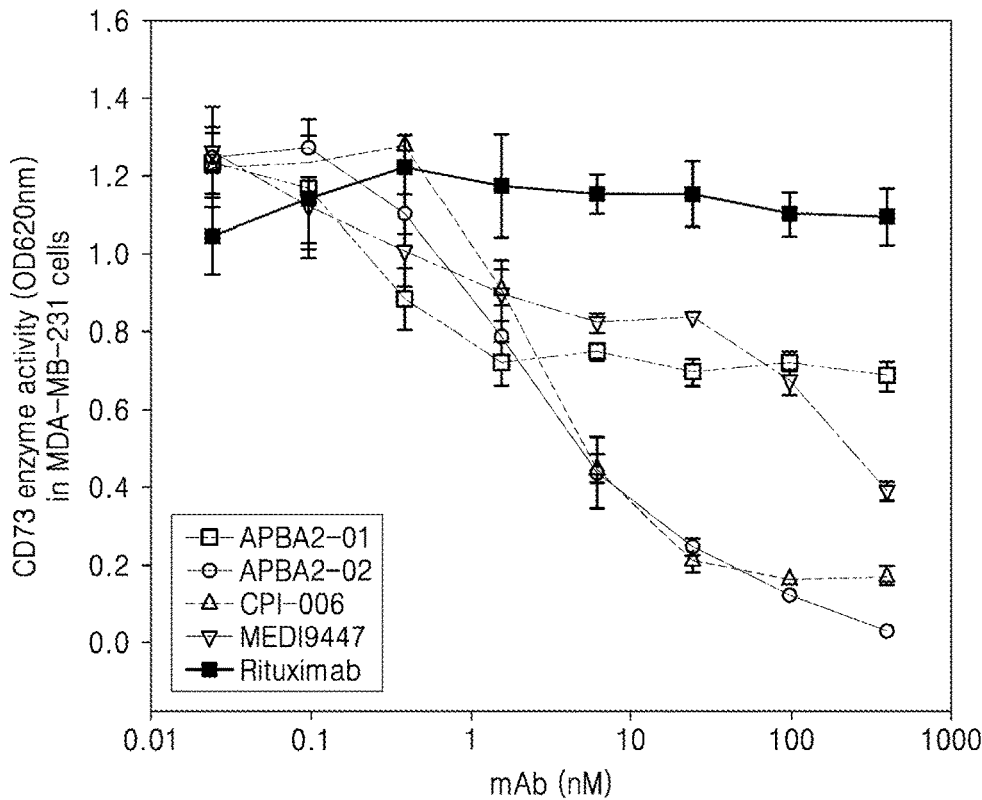
FIG. 8A is a graph showing results of a malachite green assay for comparing inhibition of membrane CD73 enzymatic activity by APBA2-01 and APBA2-02 antibodies in MDA-MB-231 cells.
Figure 8B:
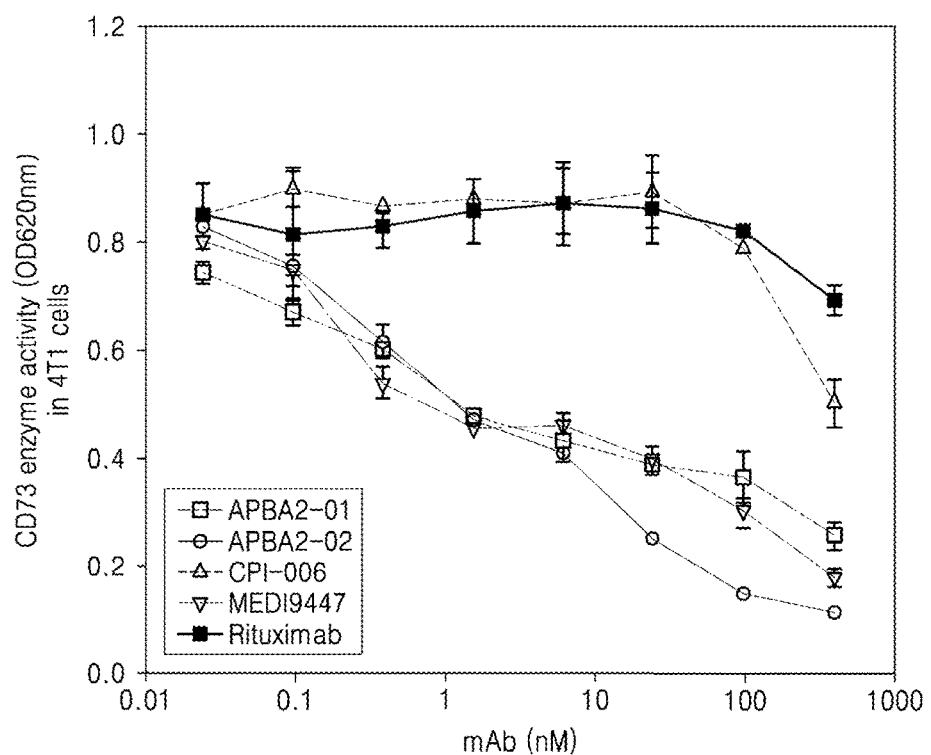
FIG. 8B is a graph showing results of a CellTiter-Glo® assay for comparing inhibition of membrane CD73 enzymatic activity by APBA2-01 and APBA2-02 antibodies in 4T1 cells.
Figure 8C:
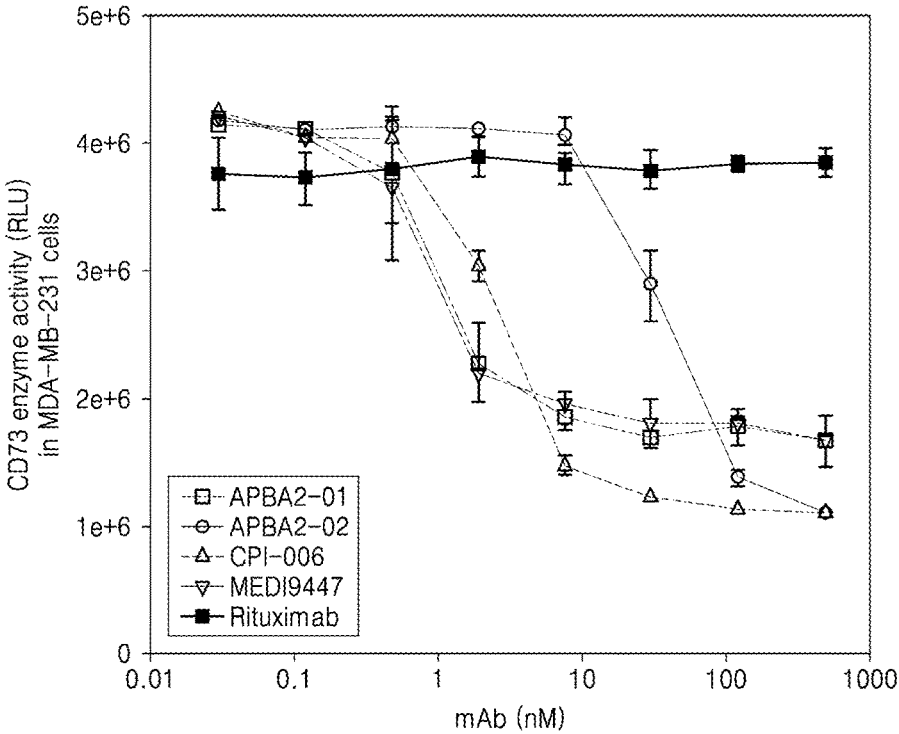
FIG. 8C is a graph showing results of a malachite green assay for comparing inhibition of membrane CD73 enzymatic activity by APBA2-01 and APBA2-02 antibodies in MDA-MB-231 cells, wherein the standard deviation is indicated by error bars and the vertical axis shows relative light units (RLU)

FIG. 8A shows results of a malachite green assay for analyzing inhibition of membrane CD73 enzymatic activity by anti-CD73 antibodies in MDA-MB-231 cells, and FIG. 8C shows results of a CellTiter-Glo® assay thereof. As shown in FIG. 8A, inhibition ability against membrane CD73 activity was high in this order of APBA2-02>CPI-006>MEDI9447>APBA2-01 in MDA-MB-231 cells, and as shown in FIG. 8C, measured in this order of MEDI9447=APBA2-01>CPI-006>APBA2-02.

Figure 8D:
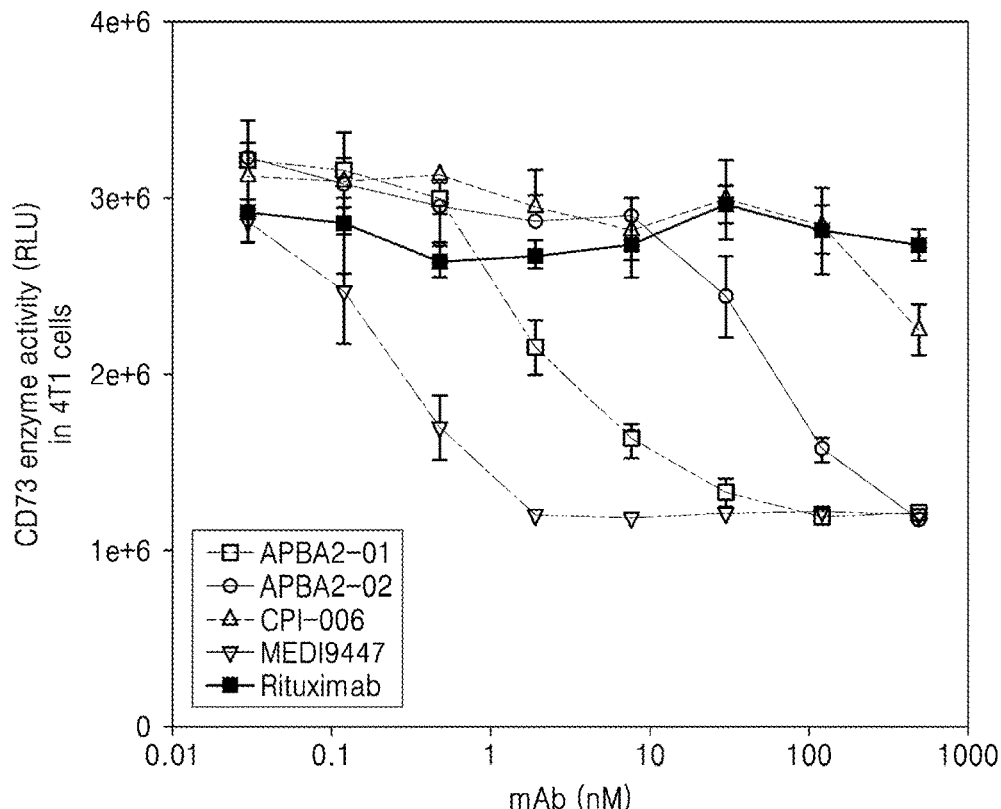
FIG. 8D is a graph showing results of a CellTiter-Glo® assay for comparing inhibition of membrane CD73 enzymatic activity by APBA2-01 and APBA2-02 antibodies in 4T1 cells, wherein the standard deviation is indicated by error bars and the vertical axis shows RLU.

FIG. 8B shows results of a malachite green assay for analyzing inhibition of membrane CD73 enzymatic activity by anti-CD73 antibodies in 4T1 cells, and FIG. 8D shows results of a CellTiter-Glo® assay thereof. As shown in FIG. 8B, the inhibition ability was measured in this order of APBA2-02>MEDI9447>APBA2-01 in 4T1 cells, and as shown in FIG. 8D, the inhibition ability was measured in this order of MEDI9447>APBA2-01>APBA2-02. There were differences in the inhibition ability according to the measurement method.

In other words, APBA2-02 antibody showed the relatively highest inhibition activity in the results of the Malachite green assay (FIGS. 8A and 8B), but showed the lowest inhibition activity in the results of the CellTiter-Glo® assay (FIGS. 8C and 8D). Further, APBA2-01 antibody and MEDI9447 showed only about 50% inhibition of CD73 activity in MDA-MB-231 cells (FIG. 8A), but showed 90% or more inhibition in 4T1 cells (FIG. 8B). Meanwhile, CPI-006 antibody showed no cross-reactivity to mouse CD73, and thus showed no reaction in 4T1 cells (FIGS. 8B and 8D).

Example 4. Internalization of Anti-CD73 Antibody into Membrane CD73-Expressing Cells Whether APBA2-01 and APBA2-02 antibodies produced and purified in Preparation Example 3 were internalized into cells by binding to membrane CD73 on the surface of the cells was examined by immunofluorescence microscopy. First, a sterile cover glass (Paul Marienfeld, Germany) was placed in a 12-well plate (SPL), and MDA-MB-231 cells ($1.0 \times 10^5$) was dispensed to each well, followed by incubation in an incubator at 37° C. and 5% $CO_2$ for 24 hours. Thereafter, the culture medium was removed, and each well was treated with APBA2-01 and APBA2-02 antibodies in the medium at a concentration of 10 μg/ml, respectively, and allowed to react at 37° C. for 20 minutes, 40 minutes, 60 minutes, and 120 minutes. Positive controls were also reacted in the same manner as above. Thereafter, the culture medium, in which the reaction was completed, was removed, respectively. The adherent cells were washed with PBS buffer three times, and fixed at 37° C. for 15 minutes by adding 1 ml of 4% formaldehyde. Washing was performed in the same manner as above, and 1 ml of 0.05% Triton-X 100 was dispensed to each well, and allowed to react at room temperature for 15 minutes to induce formation of holes in the cells. Then, the cells were washed, and blocked at room temperature for 50 minutes by adding 2% PBA buffer thereto. After washing, FITC-conjugated anti-human Fc antibody was added and allowed to react at room temperature for 50 minutes. Washing was performed in the same manner as above, and coverslips on which cells were fixed were placed on slide glasses together with a VECTASHIELD HardSet Antifade mounting medium containing 4',6-diamidino-2-phenylindole (DAPI). Thereafter, the fixed cells were analyzed by super sensitive high resolution confocal laser scanning microscopy.

Figure 9:
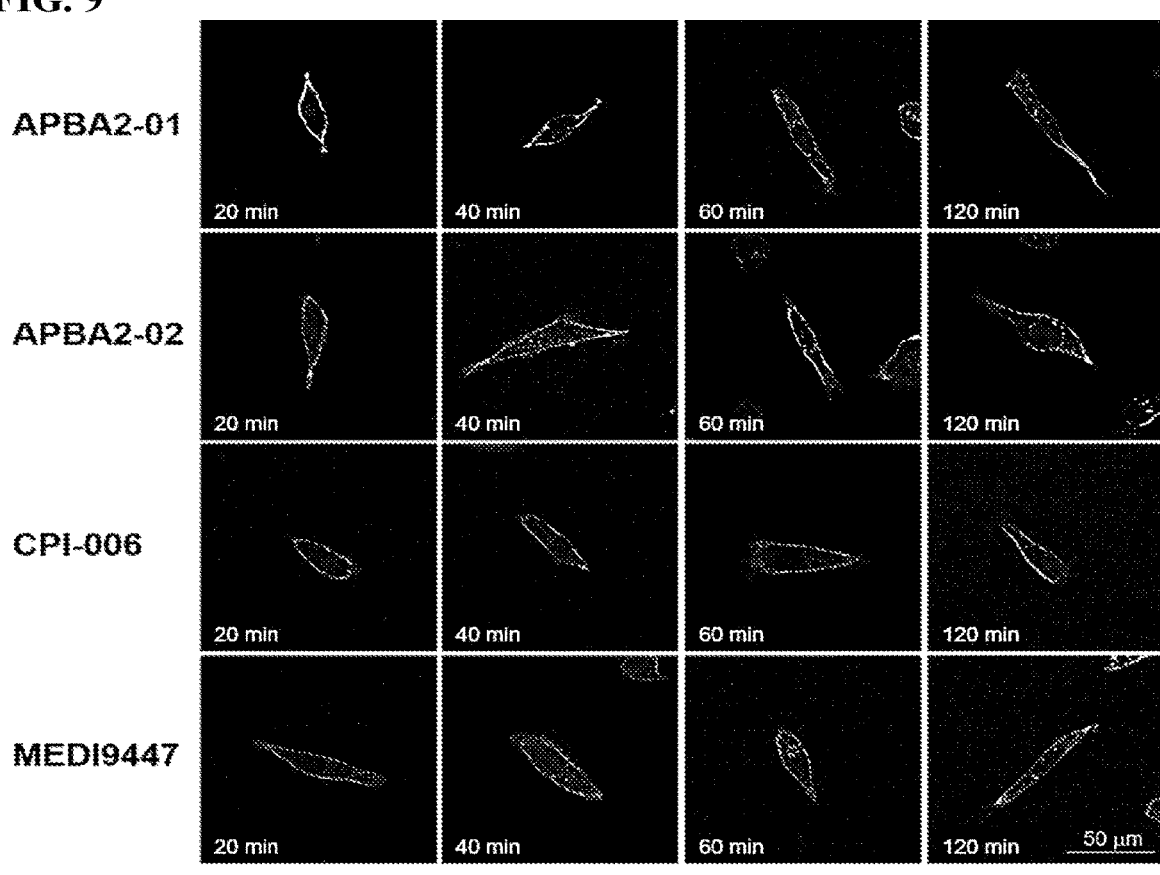
FIG. 9 shows results of scanning microscopy to confirm internalization of APBA2-01 and APBA2-02 antibodies into membrane CD73 cells, wherein CD73 corresponding to an FITC signal was expressed as shown in white and marked with a scale bar.

FIG. 9 shows images showing internalization of APBA2-01 and APBA2-02 antibodies into membrane CD73 cells, examined by super sensitive high resolution confocal laser scanning microscopy (SR-CLSM). As shown in FIG. 9, CD73 signals around the membrane of MDA-MB-231 cells were observed 20 minutes after treatment of MDA-MB-231 cells with APBA2-01 or APBA2-02 antibodies, or MEDI9447, and their internalization into the CD73 cells was observed 40 minutes after the treatment. However, internalization of CPI-006 into the cells was not observed.

Example 5. Evaluation of Efficacy in In Vivo Model

5-1. Examination of Anticancer Effect in Metastatic Breast Cancer Mouse Model Anticancer efficacies of APBA2-01 and APBA2-02 antibodies produced and purified in Preparation Example 3 were examined in metastatic breast cancer mouse models. Lung cancer was induced by administering a breast cancer cell line 4T1 ($5.0 \times 10^5$) to the tail vein of 6-week-old female BALB/c mice. 3 days later, 20 mg/kg of APBA2-01 and APBA2-02 antibodies were intraperitoneally administered (3-day intervals, 4 times), respectively. The same dose of positive control (MEDI9447 hIgG1) and negative control (isotype control IgG) groups were also administered by the same method, respectively. The weights of the mice were measured upon every drug administration. After the experiment was completed, the lung and spleen of each mouse were excised and weights thereof were measured. The excised lungs were stained with a bouin's solution, and the number of colonies were examined. Statistical analysis was performed using the GraphPad Prism Version 5.0 program. Body weight and tumor size were analyzed by one-way ANOVA, and $p < 0.05$ was considered significant.

Figure 10A:
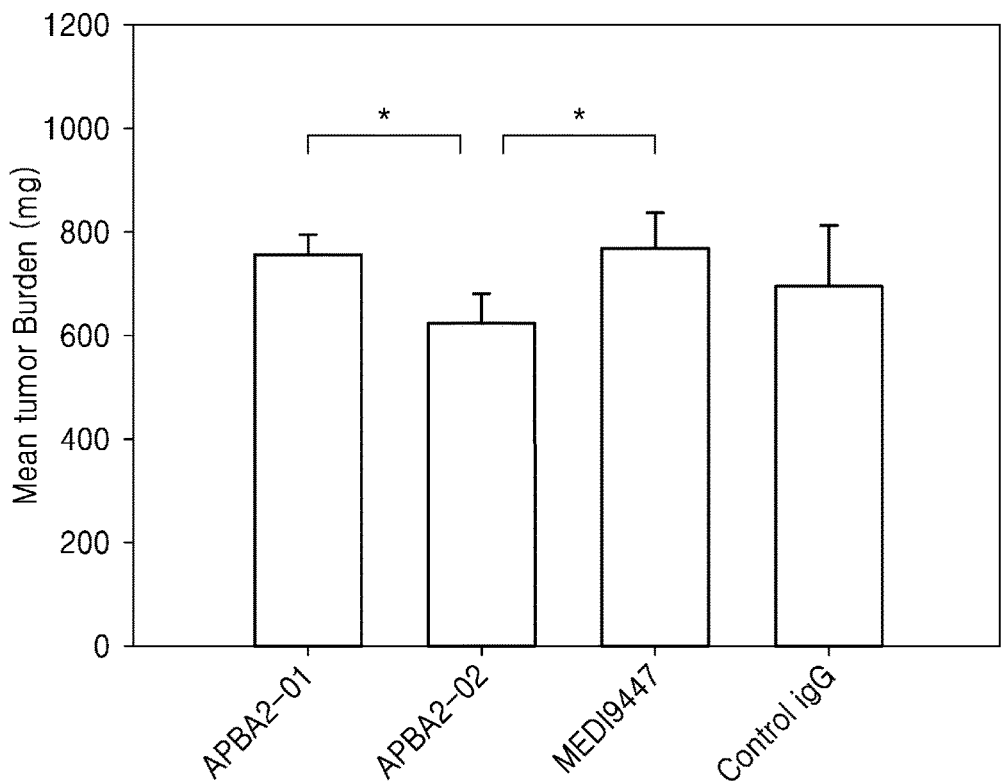
FIG. 10A is a graph showing results of evaluating anti-cancer efficacy of APBA2-01 and APBA2-02 antibodies by measuring mean lung weight in a metastatic breast cancer mouse model, *: $P<0.05$ (one-way ANOVA)

FIG. 10A shows a graph of measuring mean lung weight in the metastatic breast cancer mouse model. As shown in FIG. 10A, the positive control and APBA2-01 antibody showed no changes in the weight of the mouse lung, as compared with the negative control, and APBA2-02 showed 10.85% reduction in the weight of the mouse lung.

Figure 10B:
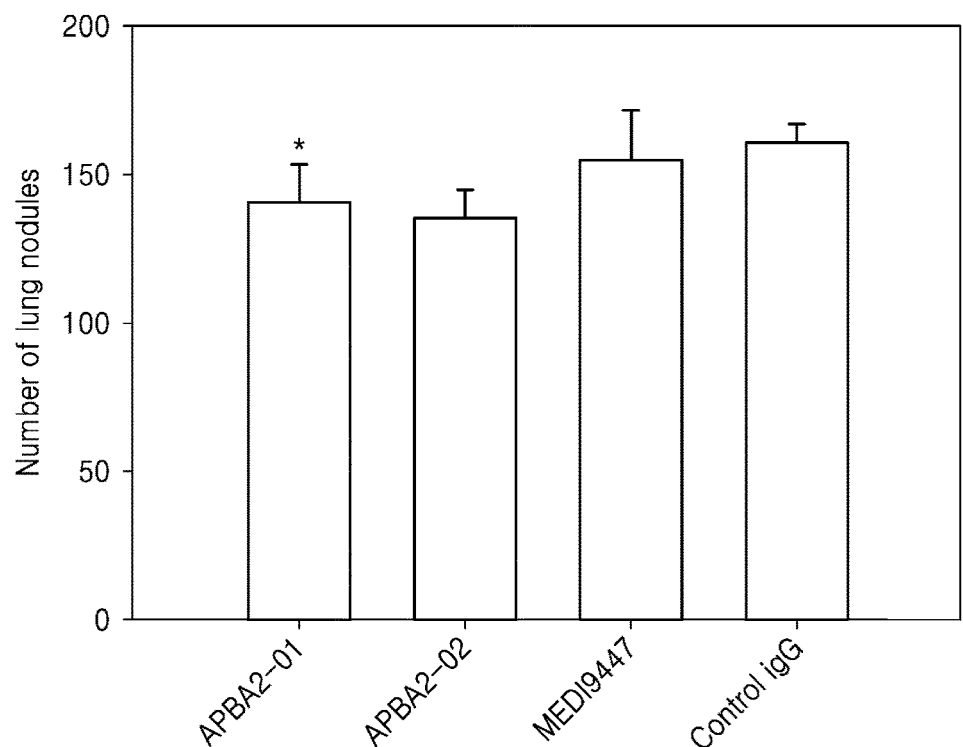
FIG. 10B is a graph showing results of evaluating anti-cancer efficacy of APBA2-01 and APBA2-02 antibodies by measuring the number of metastatic colonies in the lungs of a metastatic breast cancer mouse model, *: $P<0.05$ (one-way ANOVA)

FIG. 10B is a graph of measuring the number of metastatic colonies in the lungs of the metastatic breast cancer mouse models. As shown in FIG. 10B, the positive control, APBA2-01 and APBA2-02-administered groups showed 0.04%, 13%, and 16% reduction in the number of metastatic colonies in the lung, respectively, as compared with the negative control, but there was no statistical significance.

Meanwhile, with regard to the body weights and spleen weights of the mice, no significant changes were observed in APBA2-01, APBA2-01, or positive control-administered groups, as compared with the negative control.

5-2. Examination of Cancer Growth Inhibition in Breast Cancer Mouse Model

Cancer growth-inhibitory effects of APBA2-01 and APBA2-02 antibodies produced and purified in Preparation Example 3 were examined in breast cancer mouse models. A breast cancer cell line 4T1 ($5.0 \times 10^5$) was injected into a mammary fat pad to induce breast cancer. 3 days later, APBA2-01 and APBA2-02 antibodies were mixed with TBS buffer at pH 7.4, respectively, and intraperitoneally administered to mice at a total dose of 20 mg/kg (2-day intervals, 6 times). Positive controls (MEDI9447 mouse IgG1, IgG2a) and negative controls (isotype control mouse IgG1, IgG2a) (Bio X Cell) were also administered at the same dose by the same method. Breast cancer size was measured at 2-day intervals using calipers. Six days after the end of the last antibody administration, the lungs of the mice were excised and cancer cell metastasis was observed.

Figure 11A:
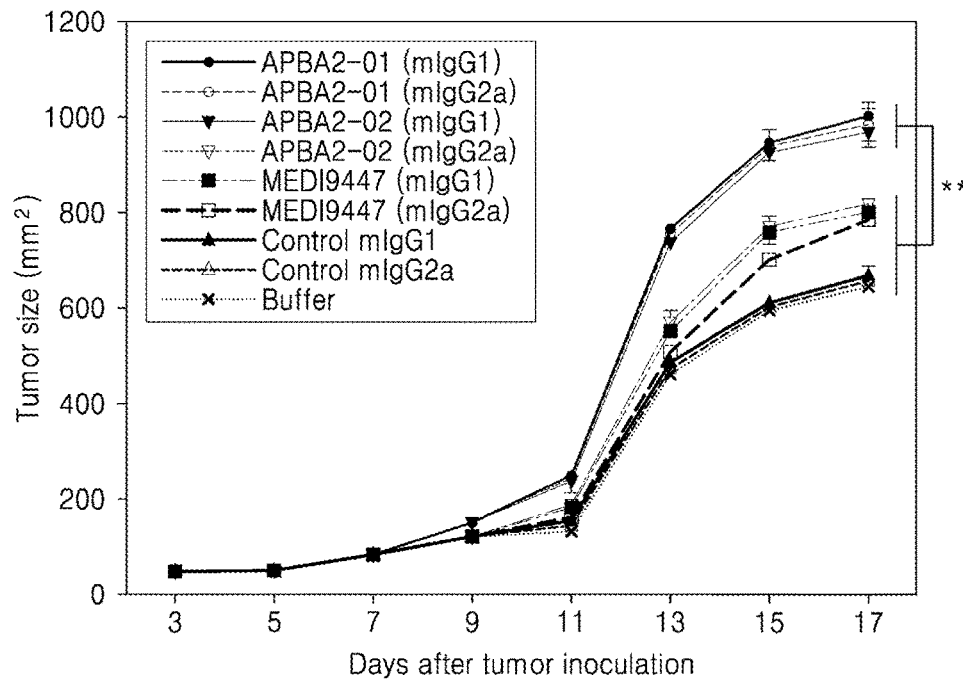
FIG. 11A is a graph showing results of evaluating tumor growth inhibition efficacy of APBA2-01 and APBA2-02 mIgG antibodies by measuring tumor volume in a breast cancer mouse model, *: $P<0.05$, **: $P<0.01$, ns(not significant: $P>0.05$ (two-way ANOVA)
Figure 11B:
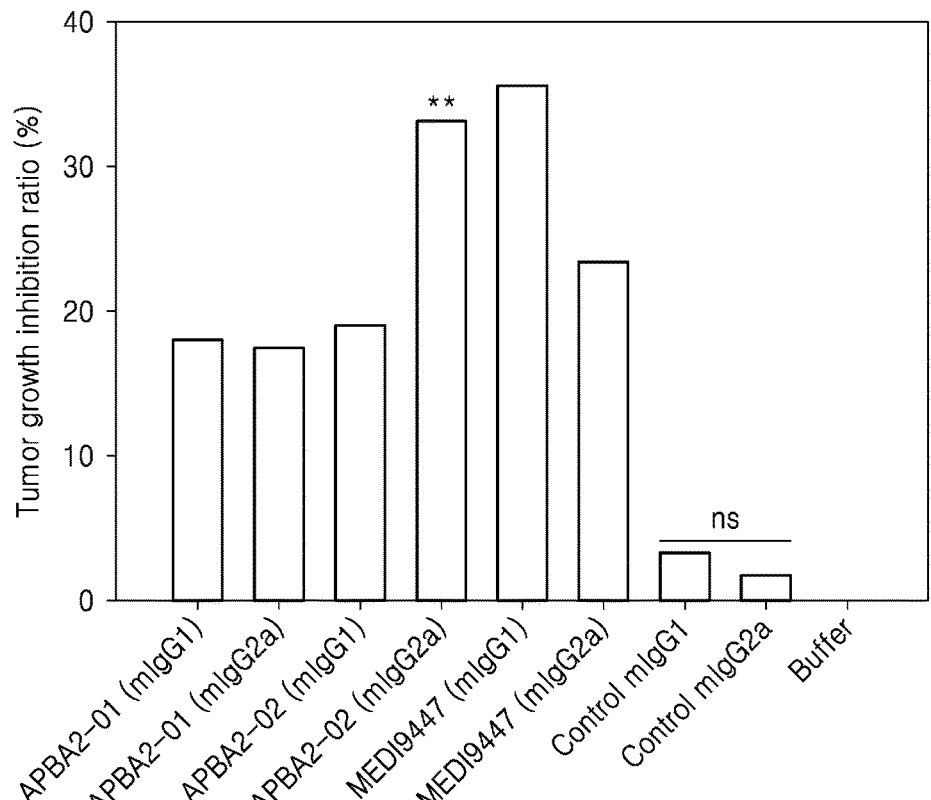
FIG. 11B is a graph showing results of evaluating tumor growth inhibition efficacy of APBA2-01 and APBA2-02 mIgG antibodies by comparing tumor growth inhibitory activity between antibody samples in a breast cancer mouse model.

FIG. 11A shows a graph of examining tumor growth inhibition efficacy of mIgG1 and mIgG2a of APBA2-01 and mIgG1 and mIgG2a of APBA2-01 by measuring tumor volume in the breast cancer mouse model, and FIG. 11B shows a graph of examining tumor growth inhibition efficacy by comparing tumor growth inhibitory activities.

As shown in FIGS. 11A and 111B, APBA2-01 antibody showed about 17% inhibition of breast cancer growth, regardless of the Fc function of the antibody, as compared with the negative control. With regard to APBA2-02 antibody, mIgG2a having Fc function showed 33% inhibition of breast cancer growth, and mIgG1 having no Fc function showed 18% inhibition of breast cancer growth. Meanwhile, with regard to the positive control, mIgG2a having Fc function showed 23% inhibition, and mIgG1 having no Fc function showed 35% inhibition.

Figure 11C:
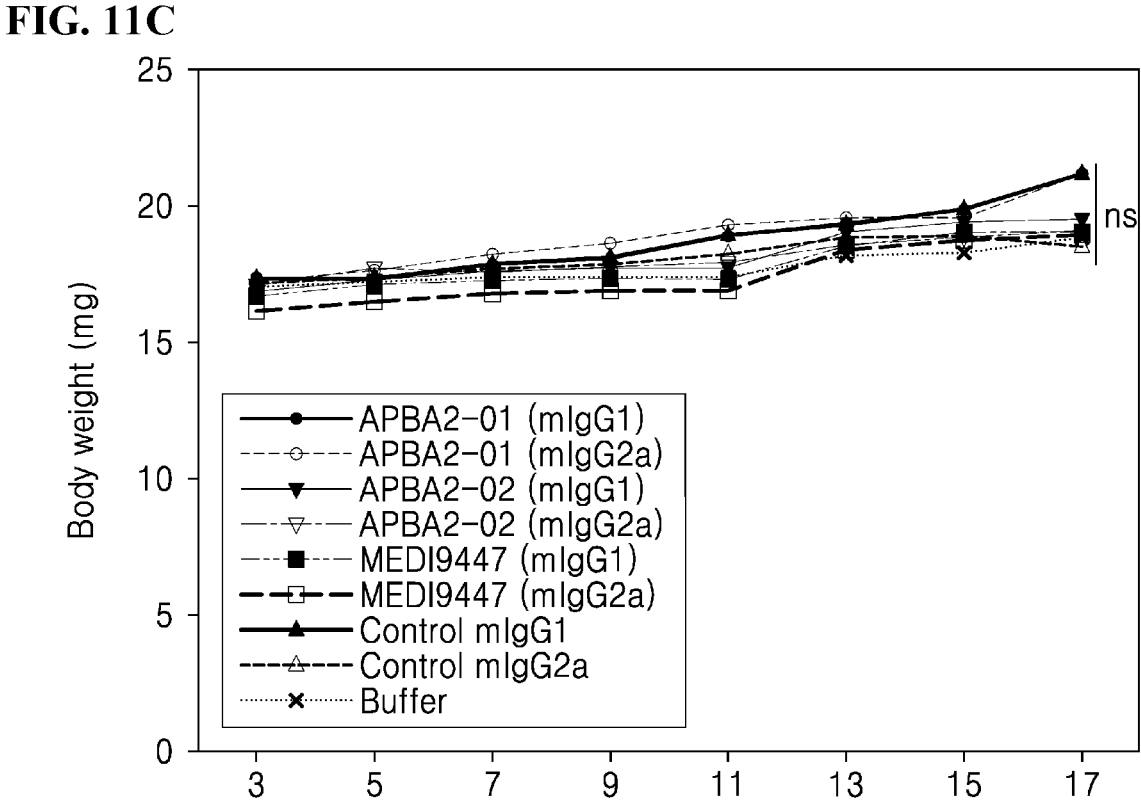
FIG. 11C is a graph showing results of evaluating tumor growth inhibition efficacy of APBA2-01 and APBA2-02 mIgG antibodies by measuring the body weight of a breast cancer mouse model, *: $P<0.05$, **: $P<0.01$, ns(not significant: $P>0.05$ (two-way ANOVA)

FIG. 11C shows a graph showing the body weights of breast cancer mouse models. As shown in FIG. 11C, during the experiment, there were no changes in the body weights of the mice. In addition, there was no lung metastasis of cancer cells.

Example 6. Evaluation of Efficacy in In Vitro Cell Model 6-1. Preparation of Monoclonal Antibody Myxengo (USA) was asked to select antibodies specifically binding to CD73 protein. The naive human scFv library owned by Myxengo was used and biopanning was performed to select candidate antibody clones. The selected clones were expressed as IgG4 antibody and the corresponding culture media were delivered from Myxengo. Each of the received culture media was subjected to affinity chromatography using CaptureSelect IgG-CH1 Affinity Matrix resin to isolate and purify each IgG4 antibody protein, and experiments were performed in the same manner as in Preparation Example 2-2.

6-2. Examination of Enzymatic Activity of Membrane CD73 Protein

The inhibitory activity of seven kinds of human anti-CD73 IgG1 antibodies prepared in Example 6-1 against membrane CD73 enzymatic activity was examined by the same method as in Example 3-2. At this time, CPI-006 and MEDI9947 were used as positive controls.

Figure 12A:
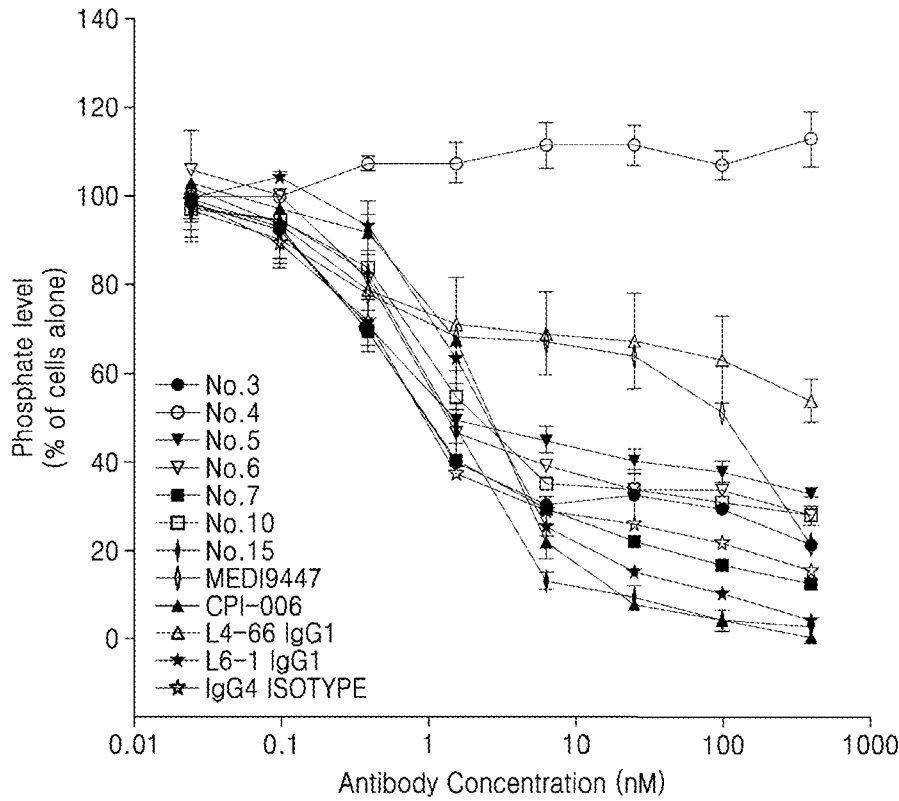
FIG. 12A is a graph showing results of a malachite green assay for comparing inhibition of membrane CD73 enzymatic activity by anti-CD73 antibodies in MDA-MB-231 cells.
Figure 12B:
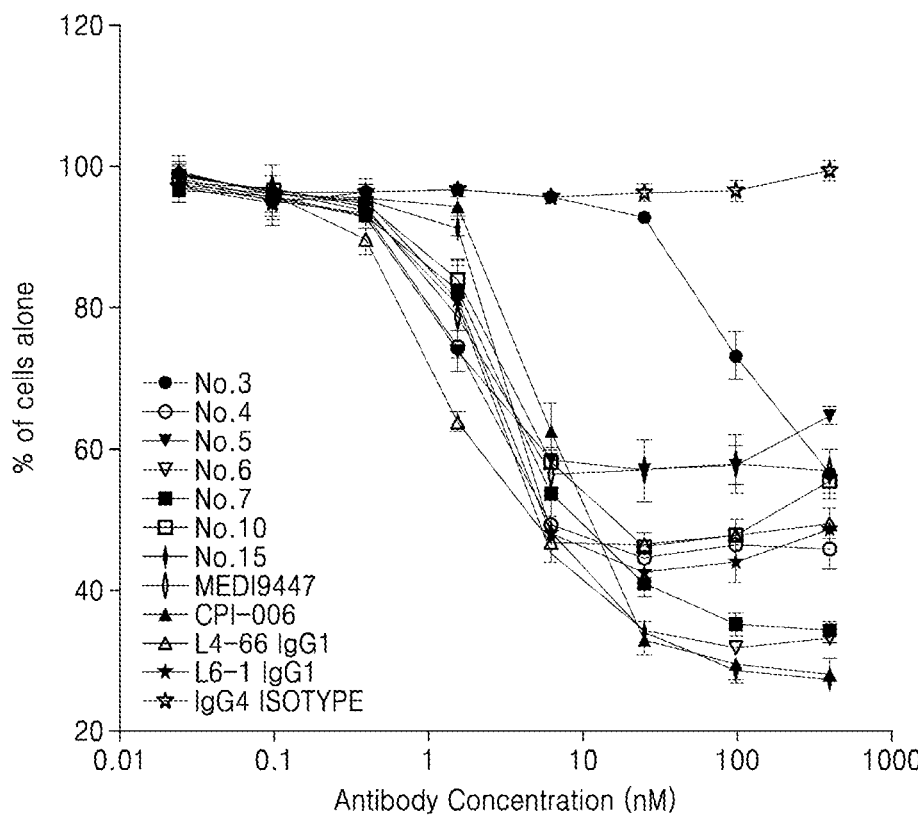
FIG. 12B is a graph showing results of a CellTiter-Glo® assay for comparing inhibition of CD73 enzymatic activity by anti-CD73 antibodies in MDA-MB-231 cells.

FIG. 12A shows results of a malachite green assay for evaluating inhibitory activity of anti-CD73 antibodies against membrane CD73 enzymatic activity in MDA-MB-231 cells, and FIG. 12B shows results of a CellTiter-Glo® assay thereof. As shown in FIGS. 12A and 12B, it was confirmed that among 7 kinds of antibodies, 5 antibodies (No. 3, 4, 6, 7, and 15) had significantly high inhibitory activity against CD73 enzymatic activity, as compared with the negative control.

Example 7. Examination of Binding Ability to Membrane CD73 Protein

To examine species cross-reactivity of anti-CD73 antibodies (Myxengo antibodies 3, 4, 6, 7, and 15) selected in Example 6, mouse cell membrane CD73 expressing cell lines (4T1 (ATCC, CRL-2539) and 4T1. 2 (ATCC, CRL-3406)) were used to perform antibody binding tests. First, 4T1 cells were cultured in an RPMI-1640 medium (Gibco, Cat No. A10491-01) supplemented with 10% fetal bovine serum (FBS)(Gibco, Cat No. 16000-044), and 4T1.2 cells were cultured in an AlphaMEM medium (Minimum Essential Medium; Corning Fisher Sci, 10-022-CV) supplemented with 10% FBS. Thereafter, adherent cells on a culture plate were separated using trypsin-EDTA (Gibco, Cat No. 25200-056), and then $2.0 \times 10^5$ cells thereof was dispensed in a 1.5-ml tube. Thereafter, cells were precipitated using a centrifuge, and then the supernatant was removed. Cells were suspended in 100 μl of the antibody sample which was diluted at a concentration of 100 nM in MACS buffer [DPBS buffer (Gibco) supplemented with 0.5% bovine serum albumin (sigma), 2 mM EDTA (Intron bio)], and allowed to react at 4° C. for 1 hour. Thereafter, 800 μl of MACS buffer was added, and centrifugation was performed to remove the supernatant. 50 μl of secondary antibody goat anti-human IgG Fc FITC (Novex, A18830) diluted at a ratio of 1:500 in MACS buffer was added to suspend the cells. Reaction was allowed at 4° C. for 1 hour, and then 500 μl of MACS buffer was added and centrifugation was performed to remove the supernatant. Thereafter, cells were suspended and fixed with 200 μl of 0.4% paraformaldehyde (T&I, diluted in PBS), and the prepared samples were analyzed using a flow cytometer (BD, FACSVerse).

Figure 13A:
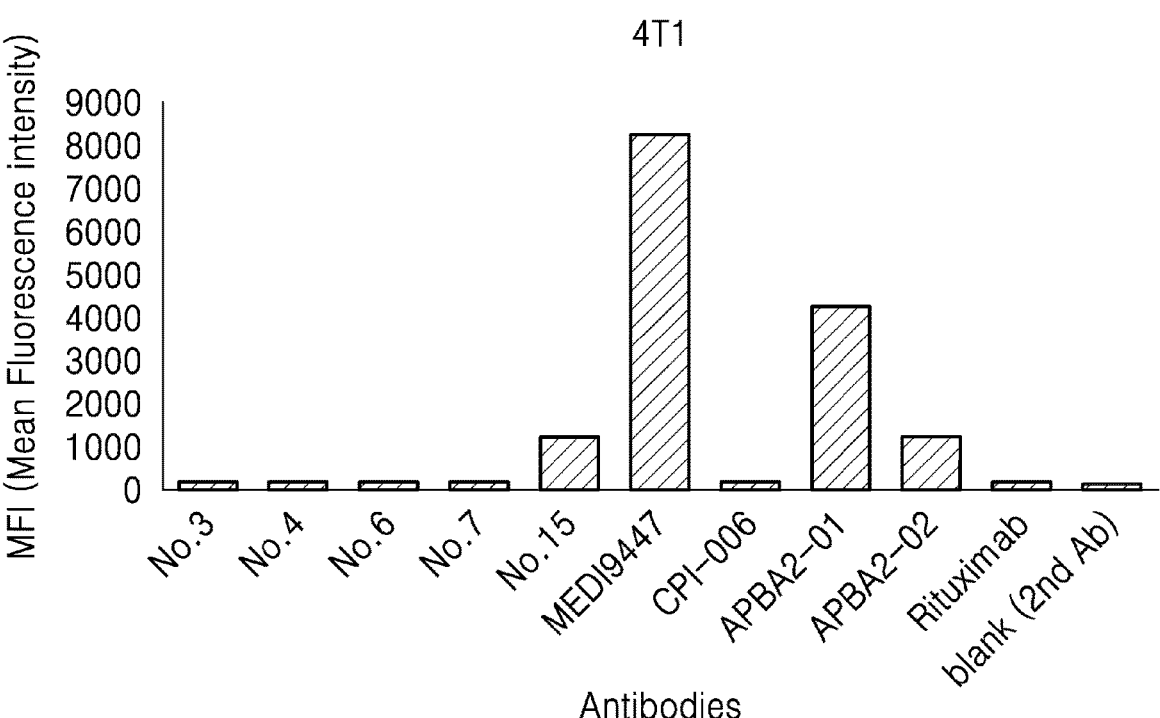
FIG. 13A is a graph showing binding abilities of Myxengo 3, 4, 6, 7, and 15 antibodies to membrane CD73 protein in 4T1 cells.
Figure 13B:
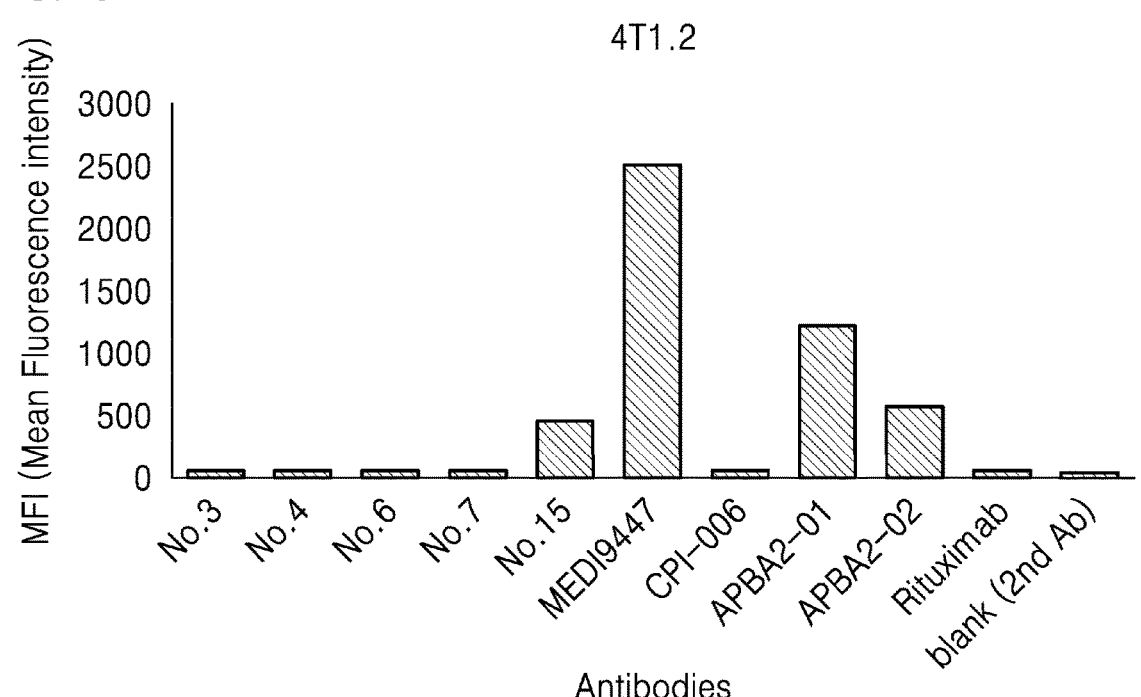
FIG. 13B is a graph showing binding abilities of Myxengo 3, 4, 6, 7, and 15 antibodies to membrane CD73 protein in 4T1.2 cells.

FIG. 13A shows a graph showing the binding ability of Myxengo 3, 4, 6, 7, and 15 antibodies to membrane CD73 protein in 4T1 cells. FIG. 13B shows a graph showing the binding ability of Myxengo 3, 4, 6, 7, and 15 antibodies to membrane CD73 protein in 4T1.2 cells.

As shown in FIGS. 13A and 13B, among five antibodies (No. 3, 4, 6, 7, and 15), one antibody (No. 15) strongly bound to mouse membrane CD73, as compared with the negative control, and showed antigen binding ability at a similar level to that of APBA2-02 antibody. However, four antibodies (No. 3, 4, 6, 7) did not bind to mouse membrane CD73. In other words, Myxengo 15 antibody is expected to have similar properties to APBA2-02, because it exhibited antigen-binding ability at a similar level to that of APBA2-02 antibody. Therefore, Myxengo 15 antibody can specifically bind to CD73 while having species cross-reactivity.

In sum, the monoclonal antibodies or antigen binding fragments thereof as disclosed herein can bind to CD73, reduce enzymatic activity of CD73 protein, and inhibit cancer metastasis or cancer growth, enabling the uses thereof as therapeutic agents for cancer. Further, the antibodies or antigen binding fragments thereof exhibit species cross-reactivity and can be used in preclinical animal tests, and thus it is possible to save time and cost required for testing side effects, toxicity, and/or stability of immunotherapeutic agents.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details can be made therein without departing from the spirit and scope of the disclosure as defined by the following claims.

The breadth and scope of the present invention should not be limited by any of the above-described exemplary embodiments but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

---

What is claimed is:

1. A monoclonal antibody or an antigen binding fragment thereof comprising:

a heavy chain variable region comprising a heavy chain complementarity determining domain 1 (CDRH1) comprising the amino acid sequence of SEQ ID NO: 78, CDRH2 comprising the amino acid sequence of SEQ ID NO:79, and CDRH3 comprising the amino acid sequence of SEQ ID NO:80; and a light chain variable region comprising CDRL1 comprising the amino acid sequence of SEQ ID NO:93, CDRL2 comprising the amino acid sequence of SEQ ID NO:94, and CDRL3 comprising the amino acid sequence of SEQ ID NO:95.

2. The antibody or the antigen binding fragment thereof of claim 1, wherein the antibody is a human antibody or chimeric antibody.

3. A nucleic acid encoding the antibody or the antigen binding fragment thereof of claim 1.

4. An expression vector comprising the nucleic acid of claim 3.

5. A cell transformed with the expression vector of claim 4.

6. A composition comprising the antibody or the antigen binding fragment thereof of claim 1.

7. The composition of claim 6, further comprising an immune checkpoint blockade or a chemotherapeutic agent.

8. A method of treating cancer in a subject in need thereof, comprising administering the antibody or antigen binding fragment thereof of claim 1 to the subject, wherein the cancer is a CD73 overexpressing cancer.

9. The method of claim 8, wherein the cancer is breast cancer, triple-negative breast cancer (TBNC), pancreatic cancer, colorectal cancer, ovarian cancer, gastric cancer, bladder cancer, leukemia, prostate cancer, malignant melanoma, cancer, esophageal cancer, stomach cancer, head and neck cancer, lung cancer, or kidney cancer.

10. The antibody or the antigen binding fragment thereof of claim 1, comprising: a heavy chain variable region comprising the amino acid sequence of SEQ ID NO:104; and a light chain variable region comprising the amino acid sequence of SEQ ID NO:105.

* * * * *